(12) United States Patent
Pannequin et al.

(10) Patent No.: US 9,217,032 B2
(45) Date of Patent: Dec. 22, 2015

(54) METHODS FOR TREATING COLORECTAL CANCER

(75) Inventors: Julie Pannequin, Sète (FR); Leïla Houhou, Montpellier (FR); Bérénice Framery, Montpellier (FR); Nejla Erkilic, Juvignac (FR); Dominique Joubert, Sète (FR); Frédéric Hollande, Les Matelles (FR)

(73) Assignee: LES LABORATOIRES SERVIER, Suresnes (FR)

( * ) Notice: Subject to any disclaimer, the term of this patent is extended or adjusted under 35 U.S.C. 154(b) by 676 days.

(21) Appl. No.: 12/984,532

(22) Filed: Jan. 4, 2011

(65) Prior Publication Data

US 2011/0177063 A1 Jul. 21, 2011

Related U.S. Application Data

(60) Provisional application No. 61/293,612, filed on Jan. 8, 2010, provisional application No. 61/367,855, filed on Jul. 26, 2010.

(51) Int. Cl.

| A61K 39/395 | (2006.01) |
|---|---|
| C07K 16/26 | (2006.01) |
| C07K 5/107 | (2006.01) |
| C07K 16/30 | (2006.01) |
| G01N 33/574 | (2006.01) |
| C07K 16/22 | (2006.01) |
| A61K 39/00 | (2006.01) |

(52) U.S. Cl.
CPC ............ *C07K 16/26* (2013.01); *C07K 5/1016* (2013.01); *C07K 16/3046* (2013.01); *G01N 33/57419* (2013.01); *A61K 39/39558* (2013.01); *A61K 2039/505* (2013.01); *C07K 2317/73* (2013.01); *C07K 2317/76* (2013.01); *G01N 2333/595* (2013.01); *G01N 2800/52* (2013.01)

(58) Field of Classification Search
CPC ........... A61K 39/395; A61K 39/39558; C07K 14/595; C07K 16/22; C07K 16/26
USPC .......... 424/130.1, 141.1, 145.1, 155.1, 156.1, 424/158.1, 172.1, 174.1
See application file for complete search history.

(56) References Cited

U.S. PATENT DOCUMENTS

| 2001/0039017 A1 | 11/2001 | Waldman et al. |
| 2009/0275546 A1 | 11/2009 | Signore et al. |
| 2011/0318380 A1 | 12/2011 | Brix et al. |

FOREIGN PATENT DOCUMENTS

| WO | WO 2004/090547 A2 | 10/2004 |
| WO | WO 2006/032980 A1 | 3/2006 |
| WO | WO 2007/135542 A2 | 11/2007 |
| WO | WO 2008/076454 A1 | 6/2008 |
| WO | WO 2009/099649 A1 | 8/2009 |

OTHER PUBLICATIONS

Rengifo-Cam, W., et al. Current Pharmaceutical Design, 10: 2345-2358, 2004.*
Bismuth, H., et al. Annals of Surgery, 224(4): 509-520, 1996.*
Siddheshwar et al., 2001, "Plasma Levels of Progastrin But Not Amidated Gastrin or Glycine Extended Gastrin Are Elevated in Patients With Colorectal Carcinoma," *Gut*, 48(1):47-52.
Singh et al., 1996, "Gastrin Gene Expression is Required for the Proliferation and Tumorigenicity of Human Colon Cancer Cells," *Cancer Research* 56(18):4111-4115.
Pannequin et al., 2007, "beta-Catenin/Tcf-4 Inhibition After Progastrin Targeting Reduces Growth and Drives Differentiation of Intestinal Tumors," *Gastroenterology* 133(5):1554-1568.
Hollande et al., 2003, "Adherens Junctions and Tight Junctions Are Regulated Via Different Pathways by Progastrin in Epithelial Cells," *J. Cell Science* 116(7):1187-1197.
Singh et al., 2007, "Development of Progastrin (PG) Specific Monoclonal Antibodies (Mabs) and PG Specific Vaccine for Attenuating Growth Factor Effects of Autocrine and Endocrine PG-Like Pepticles on Colon Cancer Cells and Colon Carcinogenesis, respectively," *Proceedings of the American Association for Cancer Research Annual Meeting* (Apr. 2007, vol. 48, p. 845) and *98th Annual Meeting of the American Association for Cancer Research*, Los Angeles, CA (Abstract).
Ciccotosto et al., 1995, "Expression Processing, and Secretion of Gastrin in Patients With Colorectal Carcinoma," *Gastroenterology* 109(4):1142-1153.
Singh et al., 2000, "Mice Overexpressing Progastrin Are Predisposed for Developing Aberrant Colonic Crypt Foci in Response to AOM," *Am. Journal of Physiology* 278(3):G390-G399.
Singh et al., 2000, "Progastrin Expression Predisposes Mice to Colon Carcinomas and Adenomas in Response to a Chemical Carcinogen," *Gastroenterology* 119(1):162-171.
Hecht, 2008, "Current and Emerging Therapies for Metastatic Colorectal Cancer: Applying Research Findings to Clinical Practice," *Am. Journal of Health-System Pharmacy* 65(11):S15-S24 (suppl. 4).
Tamiya et al., 2009, "Safety of Bevacizumab Treatment in Combination With Standard Chemotherapy for Metastatic Colorectal Cancer: A Retrospective Review of 65 Japanese Patients," *Intl. J. Clin. Oncology* 14(6):513-517.
Jean at al., 2008, "Epidermal Growth Factor Receptor Monoclonal Antibodies for the Treatment of Metastatic Colorectal Cancer," *Pharmacotherapy* 28(6):742-754.
Petkova et al, 2006, "Enhanced half-life of genetically engineered human IgG1 antibodies in a humanized FcRn mouse model: potential application in humorally mediated autoimmune disease," *International Immunology* 18(12):1759-1769.
Partial International Search Report from related International Application No. PCT/EP2011/000046 dated Apr. 15, 2011.
International Search Report from related International Application No. PCT/EP2011/000046 dated Aug. 26, 2011.
Singh et al., 1996 "Gastrin Gene Expression Is Required for the Proliferation and Tumorigenicity of Human Colon Cancer Cells," *Cancer Res* 56:4111-4115.
Wicha et al., 2006 "Cancer Stem Cells: An Old Idea—A Paradigm Shift," *Cancer Res* 66(4): 1883-1890.

\* cited by examiner

*Primary Examiner* — Misook Yu
*Assistant Examiner* — Anne Holleran
(74) *Attorney, Agent, or Firm* — Dechert LLP

(57) ABSTRACT

The present disclosure is directed to methods of treating and preventing colorectal cancer metastasis or recurrence of colorectal cancer with compositions comprising anti-progastrin antibodies.

9 Claims, 68 Drawing Sheets

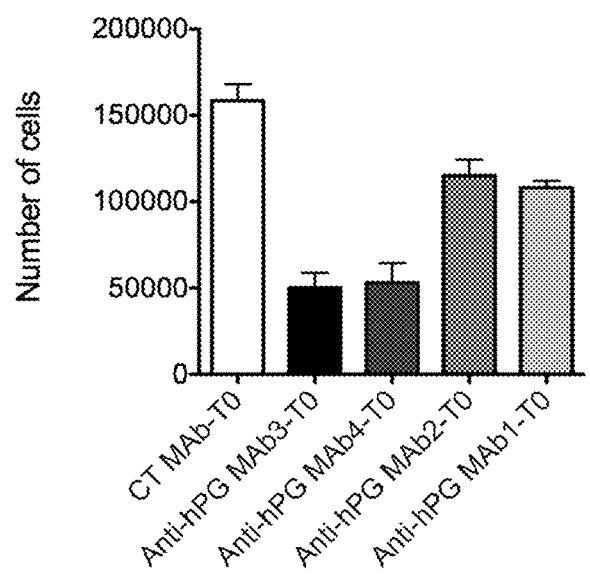

Figure 1:
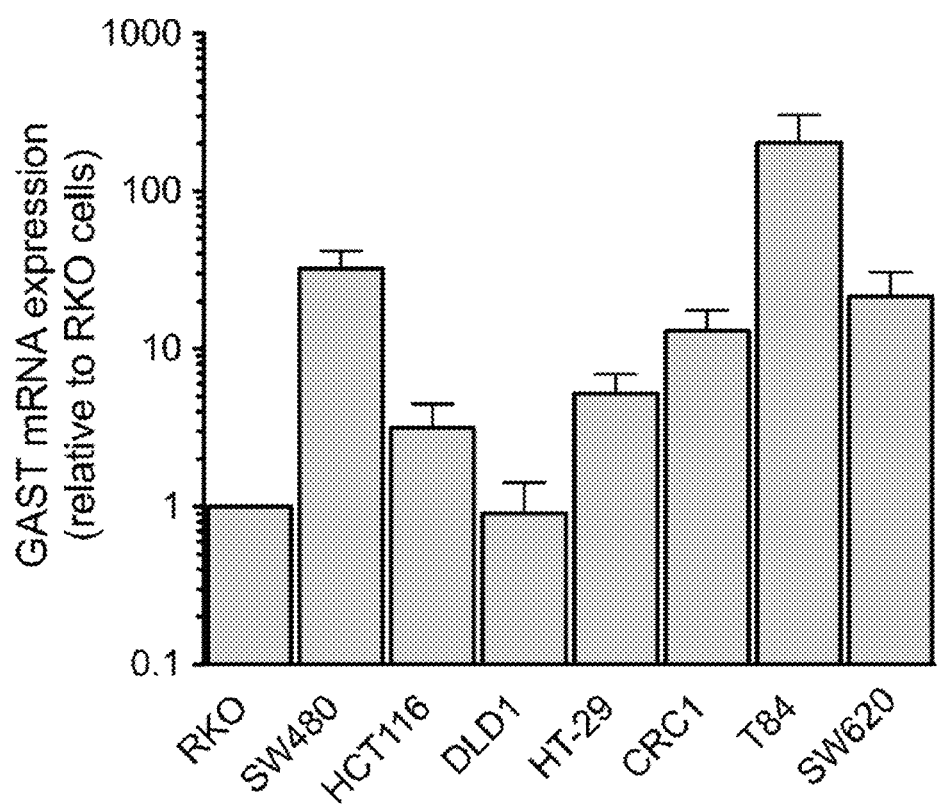

*, p=0.0372, Mann-Whitney test, n= 10 per group

Expression of the progastrin-encoding gene in primary and metastatic CRC cells grown in 2D or 3D

FIG. 30

```
Preprogastrin:  M QRLCVYVLIF ALALAAFSEA SWKPRSQQPD APLGTGANRD LELPWLEQQG
SEQ ID NO:100   -21         -11        -1 +1                11         21
                PASHHRRQLG PQGPPHLVAD PSKKQGPWLE EEEEAYGWMD FGRRSAEDEN
                31         41         51         61         71

Progastrin:                            SWKPRSQQPD APLGTGANRD LELPWLEQQG
SEQ ID NO:101                          +1                   11         21
                PASHHRRQLG PQGPPHLVAD PSKKQGPWLE EEEEAYGWMD FGRRSAEDEN
                31         41         51         61         71

G34:                   QLG PQGPPHLVAD PSKKQGPWLE EEEEAYGWMD F-NH₂
SEQ ID NO:102              41         51         61         71

G34-Gly:               QLG PQGPPHLVAD PSKKQGPWLE EEEEAYGWMD FG
SEQ ID NO:103              41         51         61         71

G17:                                   QGPWLE    EEEEAYGWMD F-NH₂
SEQ ID NO:104                          51        61         71

G17-Gly:                               QGPWLE    EEEEAYGWMD FG
SEQ ID NO:105                          51        61         71

CTFP:                                                                  SAEDEN
SEQ ID NO:106                                                          75
```

FIG. 31A mV$_H$ MAb3

```
gag gtt cag ctc cag cag tct ggg act gtg ctg gca agg cct ggg gct    48
Glu Val Gln Leu Gln Gln Ser Gly Thr Val Leu Ala Arg Pro Gly Ala
1               5                   10                  15 tcc gtg aag atg tcc tgc aag gct tct ggc tac atc ttt acc agc tac    96
Ser Val Lys Met Ser Cys Lys Ala Ser Gly Tyr Ile Phe Thr Ser Tyr
                20                  25                  30 tgg gta cac tgg gtt aaa cag agg cct gga cag ggt cta gaa tgg att   144
Trp Val His Trp Val Lys Gln Arg Pro Gly Gln Gly Leu Glu Trp Ile
            35                  40                  45 ggt ggt ttt tat cct gga aat agt gat tct agg tac aac cag aaa ttc   192
Gly Gly Phe Tyr Pro Gly Asn Ser Asp Ser Arg Tyr Asn Gln Lys Phe
        50                  55                  60 aag ggc aag gcc aca ctg act gca gtc aca tcc gcc agt act gcc tac   240
Lys Gly Lys Ala Thr Leu Thr Ala Val Thr Ser Ala Ser Thr Ala Tyr
65                  70                  75                  80 atg gac ctc agc agc ctg aca aat gag gac tct gcg gtc tat ttc tgt   288
Met Asp Leu Ser Ser Leu Thr Asn Glu Asp Ser Ala Val Tyr Phe Cys
                85                  90                  95 aca aga aga gat agt ccc cag tac tgg ggc caa ggc acc act ctc aca   336
Thr Arg Arg Asp Ser Pro Gln Tyr Trp Gly Gln Gly Thr Thr Leu Thr
                100                 105                 110 gtc tcc tca                                                        345
Val Ser Ser
            115
```

FIG. 31B mV$_L$ MAb3

```
gat gtt ttg atg acc caa act cca ctc tcc ctg cct gtc agt ctt gga    48
Asp Val Leu Met Thr Gln Thr Pro Leu Ser Leu Pro Val Ser Leu Gly
1               5                   10                  15 gat caa gcc tcc atc tct tgc aga tct agt cag agc att gta cat agt    96
Asp Gln Ala Ser Ile Ser Cys Arg Ser Ser Gln Ser Ile Val His Ser
            20                  25                  30 aat gga aac acc tat tta gaa tgg tac ctg cag aaa cca ggc cag tct   144
Asn Gly Asn Thr Tyr Leu Glu Trp Tyr Leu Gln Lys Pro Gly Gln Ser
            35                  40                  45 cca aag ctc ctg atc tac aaa gtt tcc aac cga ttt tct ggg gtc cca   192
Pro Lys Leu Leu Ile Tyr Lys Val Ser Asn Arg Phe Ser Gly Val Pro
        50                  55                  60 gac agg ttc agt ggc agt gga tca ggg aca gat ttc aca ctc aag atc   240
Asp Arg Phe Ser Gly Ser Gly Ser Gly Thr Asp Phe Thr Leu Lys Ile
65                  70                  75                  80 agc aga ctg gag gct gag gat ctg gga gtt tat tac tgc ttt caa ggt   288
Ser Arg Leu Glu Ala Glu Asp Leu Gly Val Tyr Tyr Cys Phe Gln Gly
                85                  90                  95 tca cat gtt ccg ttc acg ttc gga ggg ggg acc aag ctg gaa ata aaa   336
Ser His Val Pro Phe Thr Phe Gly Gly Gly Thr Lys Leu Glu Ile Lys
            100                 105                 110
```

FIG. 31C mV$_H$ MAb4

```
cag gtt cag ttg cag cag tct gga gct gag ctg atg aag cca ggg gcc    48
Gln Val Gln Leu Gln Gln Ser Gly Ala Glu Leu Met Lys Pro Gly Ala
1               5                   10                  15 tca gtg aag ata tcc tgc aag gct act ggc tac aca ttc agt agc tcc    96
Ser Val Lys Ile Ser Cys Lys Ala Thr Gly Tyr Thr Phe Ser Ser Ser
                20                  25                  30 tgg ata gag tgg tta aaa cag agg cct gga cat ggc ctt gag tgg att   144
Trp Ile Glu Trp Leu Lys Gln Arg Pro Gly His Gly Leu Glu Trp Ile
                35                  40                  45 gga gag ttt tta cct gga agt ggt agt aca gac tac aat gag aag ttc   192
Gly Glu Phe Leu Pro Gly Ser Gly Ser Thr Asp Tyr Asn Glu Lys Phe
        50                  55                  60 aag ggc aag gcc aca ttc act gca gac aca tcc tcc gac aca gcc tac   240
Lys Gly Lys Ala Thr Phe Thr Ala Asp Thr Ser Ser Asp Thr Ala Tyr
65                  70                  75                  80 atg cta ctc agc agc ctg aca tct gag gac tct gcc gtc tat tac tgt   288
Met Leu Leu Ser Ser Leu Thr Ser Glu Asp Ser Ala Val Tyr Tyr Cys
                85                  90                  95 gca act gat ggt aat tat gac tgg ttt gct tac tgg ggc caa ggg act   336
Ala Thr Asp Gly Asn Tyr Asp Trp Phe Ala Tyr Trp Gly Gln Gly Thr
                100                 105                 110 ctg gtc act gtc tct gca                                            354
Leu Val Thr Val Ser Ala
            115
```

FIG. 31D mV$_L$ MAb4

```
gat ctt gtg atg acc caa act cca ctc tcc ctg cct gtc agt ctt gga   48
Asp Leu Val Met Thr Gln Thr Pro Leu Ser Leu Pro Val Ser Leu Gly
1               5                   10                  15 gat caa gcc tcc atc tct tgc aga tct agt cag agc ctt gta cac agt   96
Asp Gln Ala Ser Ile Ser Cys Arg Ser Ser Gln Ser Leu Val His Ser
                20                  25                  30 agt gga gtc acc tat tta cat tgg tac ctg cag aag cca ggc cag tct  144
Ser Gly Val Thr Tyr Leu His Trp Tyr Leu Gln Lys Pro Gly Gln Ser
            35                  40                  45 cca aag ctc ctg atc tac aaa gtt tcc aac cga ttt tct ggg gtc cca  192
Pro Lys Leu Leu Ile Tyr Lys Val Ser Asn Arg Phe Ser Gly Val Pro
        50                  55                  60 gac agg ttc agt ggc agt gga tca ggg aca gat ttc aca ctc aag atc  240
Asp Arg Phe Ser Gly Ser Gly Ser Gly Thr Asp Phe Thr Leu Lys Ile
65                  70                  75                  80 agc aga gtg gag gct gag gat ctg gga gtt tat ttc tgc tct caa agt  288
Ser Arg Val Glu Ala Glu Asp Leu Gly Val Tyr Phe Cys Ser Gln Ser
                85                  90                  95 aca cat gtt cct ccc acg ttc ggc tcg ggg aca aag ttg gaa ata aaa  336
Thr His Val Pro Pro Thr Phe Gly Ser Gly Thr Lys Leu Glu Ile Lys
                100                 105                 110
```

FIG. 31E mV$_H$ MAb8

```
gaa gtg cag ctg gtg gag tct ggg gga ggc tta gtg aag cct gga ggg    48
Glu Val Gln Leu Val Glu Ser Gly Gly Gly Leu Val Lys Pro Gly Gly
1               5                   10                  15 tcc ctg aaa ctc tcc tgt gca gcc tct gga ttc act ttc act acc tat    96
Ser Leu Lys Leu Ser Cys Ala Ala Ser Gly Phe Thr Phe Thr Thr Tyr
            20                  25                  30 gcc atg tct tgg gtt cgc cag act ccg gag aag agg ctg gag tgg gtc   144
Ala Met Ser Trp Val Arg Gln Thr Pro Glu Lys Arg Leu Glu Trp Val
            35                  40                  45 gca acc att agt agt ggt ggt act tac acc tac tat cca gac agt gtg   192
Ala Thr Ile Ser Ser Gly Gly Thr Tyr Thr Tyr Tyr Pro Asp Ser Val
        50                  55                  60 aag ggt cga ttc acc atc tcc aga gac aat gcc aag aac gcc cta tac   240
Lys Gly Arg Phe Thr Ile Ser Arg Asp Asn Ala Lys Asn Ala Leu Tyr
65                  70                  75                  80 ctg caa atg agc agt ctg agg tct gag gac acg gcc atg tat tac tgt   288
Leu Gln Met Ser Ser Leu Arg Ser Glu Asp Thr Ala Met Tyr Tyr Cys
                85                  90                  95 gca aca cag ggg aat tac tct ttg gac ttc tgg ggc caa ggc acc tct   336
Ala Thr Gln Gly Asn Tyr Ser Leu Asp Phe Trp Gly Gln Gly Thr Ser
                100                 105                 110 ctc aca gtc tcc tca                                               351
Leu Thr Val Ser Ser
            115
```

FIG. 31F mV$_L$ MAb8

```
gac att gtg atg acg cag gct gca tcc tct aat cca gtc act ctt gga   48
Asp Ile Val Met Thr Gln Ala Ala Ser Ser Asn Pro Val Thr Leu Gly
1               5                   10                  15 aca tcc gct tcc atc tcc tgc agg tct agt aag agt ctc cga cat act   96
Thr Ser Ala Ser Ile Ser Cys Arg Ser Ser Lys Ser Leu Arg His Thr
                20                  25                  30 aaa ggc atc act ttt ttg tat tgg tat ctg cag aag cca ggc cag tct  144
Lys Gly Ile Thr Phe Leu Tyr Trp Tyr Leu Gln Lys Pro Gly Gln Ser
                35                  40                  45 cct cag ctc ctg att tat cag atg tcc aac ctt gcc tca gga gtc cca  192
Pro Gln Leu Leu Ile Tyr Gln Met Ser Asn Leu Ala Ser Gly Val Pro
        50                  55                  60 gac agg ttc agt agc agt ggg tca gga act gat ttc aca ctg aga atc  240
Asp Arg Phe Ser Ser Ser Gly Ser Gly Thr Asp Phe Thr Leu Arg Ile
65                  70                  75                  80 agc aga gtg gag gct gag gat ttg ggt gtt tat tac tgt gct caa aat  288
Ser Arg Val Glu Ala Glu Asp Leu Gly Val Tyr Tyr Cys Ala Gln Asn
                85                  90                  95 cta gaa ctt ccg ctc acg ttc ggt gct ggg acc aag ctg gag ctg aaa  336
Leu Glu Leu Pro Leu Thr Phe Gly Ala Gly Thr Lys Leu Glu Leu Lys
                100                 105                 110
```

FIG. 31G mV$_H$ MAb13

```
gag gtg cag ctg gtg gag tct ggg gga ggc ttg gtg cag cct gga ggg    48
Glu Val Gln Leu Val Glu Ser Gly Gly Gly Leu Val Gln Pro Gly Gly
1               5                   10                  15 tcc ctg aaa ctc tcc tgt gca gcc tct gga ttc att ttc agt agc tat    96
Ser Leu Lys Leu Ser Cys Ala Ala Ser Gly Phe Ile Phe Ser Ser Tyr
            20                  25                  30 ggc atg tct tgg gtt cgc cag tct cca gac agg agg ctg gag ttg gtc   144
Gly Met Ser Trp Val Arg Gln Ser Pro Asp Arg Arg Leu Glu Leu Val
        35                  40                  45 gca agt att aat act ttt ggt gat aga acc tat tat cca gac agt gtg   192
Ala Ser Ile Asn Thr Phe Gly Asp Arg Thr Tyr Tyr Pro Asp Ser Val
    50                  55                  60 aag ggc cga ttc acc atc tcc aga gac aat gcc aag aac acc ctg tac   240
Lys Gly Arg Phe Thr Ile Ser Arg Asp Asn Ala Lys Asn Thr Leu Tyr
65                  70                  75                  80 ctg caa atg acc agt ctg aag tct gag gac aca gcc att tat tac tgt   288
Leu Gln Met Thr Ser Leu Lys Ser Glu Asp Thr Ala Ile Tyr Tyr Cys
                85                  90                  95 gca aga ggg acc gga acc tac tgg ggc caa ggc acc act ctc aca gtc   336
Ala Arg Gly Thr Gly Thr Tyr Trp Gly Gln Gly Thr Thr Leu Thr Val
            100                 105                 110 tcc tca                                                            342
Ser Ser
```

FIG. 31H mV_L MAb13

```
gat gtt gtg ctg acc cag act cca ctc act ttg tcg gtt acc att gga    48
Asp Val Val Leu Thr Gln Thr Pro Leu Thr Leu Ser Val Thr Ile Gly
1               5                   10                  15 caa cca gcc tcc atc tcc tgc aag tca agt cag agc ctc tta gat agt    96
Gln Pro Ala Ser Ile Ser Cys Lys Ser Ser Gln Ser Leu Leu Asp Ser
                20                  25              30 gat gga aag aca tat ttg aat tgg ttg tta cag agg cca ggc cag tct   144
Asp Gly Lys Thr Tyr Leu Asn Trp Leu Leu Gln Arg Pro Gly Gln Ser
            35                  40                  45 cca aag cgc cta atc tat ctg gtg tct aaa ctg gac tct gga gtc cct   192
Pro Lys Arg Leu Ile Tyr Leu Val Ser Lys Leu Asp Ser Gly Val Pro
        50                  55                  60 gac agg ttc act ggc agt gga tca ggg aca gat ttc aca ctg aaa atc   240
Asp Arg Phe Thr Gly Ser Gly Ser Gly Thr Asp Phe Thr Leu Lys Ile
65                  70                  75                  80 agc aga gtg gag gct gag gat ttg gga gtt tat tat tgc tgg caa ggt   288
Ser Arg Val Glu Ala Glu Asp Leu Gly Val Tyr Tyr Cys Trp Gln Gly
                85                  90                  95 aca cat ttt cct cag acg ttc ggt gga ggc acc aag ctg gaa atc aaa   336
Thr His Phe Pro Gln Thr Phe Gly Gly Gly Thr Lys Leu Glu Ile Lys
                100                 105                 110
```

FIG. 31I mV$_H$ MAb16

```
cag gtc caa ctg cag cag tct ggg gct gaa ctg gtg aag cct ggg gct    48
Gln Val Gln Leu Gln Gln Ser Gly Ala Glu Leu Val Lys Pro Gly Ala
1               5                   10                  15 tca gtg aag ttg tcc tgc aag gct tct ggc tac acc ttc acc agc tac    96
Ser Val Lys Leu Ser Cys Lys Ala Ser Gly Tyr Thr Phe Thr Ser Tyr
                20                  25                  30 tat atg tac tgg gtg aag cag agg cct gga caa ggc ctt gag tgg att   144
Tyr Met Tyr Trp Val Lys Gln Arg Pro Gly Gln Gly Leu Glu Trp Ile
        35                  40                  45 gga gag att aat cct agc aat ggt ggt act aac ttc aat gag aag ttc   192
Gly Glu Ile Asn Pro Ser Asn Gly Gly Thr Asn Phe Asn Glu Lys Phe
        50                  55                  60 aag agc aag gcc aca ctg act gta gac aaa tcc tcc agc aca gca tac   240
Lys Ser Lys Ala Thr Leu Thr Val Asp Lys Ser Ser Ser Thr Ala Tyr
65                  70                  75                  80 atg caa ctc agc agc ctg aca tct gag gac tct gcg gtc tat tac tgt   288
Met Gln Leu Ser Ser Leu Thr Ser Glu Asp Ser Ala Val Tyr Tyr Cys
                85                  90                  95 aca aga ggc ggt tac tac ccc ttt gac tac tgg ggc caa ggc acc act   336
Thr Arg Gly Gly Tyr Tyr Pro Phe Asp Tyr Trp Gly Gln Gly Thr Thr
                100                 105                 110 ctc aca gtc tcc tca                                                351
Leu Thr Val Ser Ser
        115
```

FIG. 31J mV$_L$ MAb16

```
gat gtt gtg atg acc cag act cca ctc act ttg tcg gtt acc att ggg    48
Asp Val Val Met Thr Gln Thr Pro Leu Thr Leu Ser Val Thr Ile Gly
1               5                   10                  15 cgc cca gcc tcc atc tct tgc aag tca agt cag agc ctc tta gac agt    96
Arg Pro Ala Ser Ile Ser Cys Lys Ser Ser Gln Ser Leu Leu Asp Ser
            20                  25              30 gat gga aag aca tat ttg tat tgg ttg tta cag agg cca ggc cag tct   144
Asp Gly Lys Thr Tyr Leu Tyr Trp Leu Leu Gln Arg Pro Gly Gln Ser
            35                  40              45 cca aag cgc cta atc tat ctg gtg tct gag ctg gac tct gga gtc cct   192
Pro Lys Arg Leu Ile Tyr Leu Val Ser Glu Leu Asp Ser Gly Val Pro
        50                  55              60 gac agg atc act ggc agt ggg tcg ggg aca gat ttc aca ctg aag atc   240
Asp Arg Ile Thr Gly Ser Gly Ser Gly Thr Asp Phe Thr Leu Lys Ile
65              70                  75                      80 agc aga gtg gag gct gag gat ttg gga gtt tat tat tgc tgg caa gga   288
Ser Arg Val Glu Ala Glu Asp Leu Gly Val Tyr Tyr Cys Trp Gln Gly
                85                  90                  95 aca cat tct ccg tac acg ttc gga ggg ggg acc aag ctg gaa ata aaa   336
Thr His Ser Pro Tyr Thr Phe Gly Gly Gly Thr Lys Leu Glu Ile Lys
            100                 105                 110
```

FIG. 31K mV$_H$ MAb19

```
gat gtg cag ctt cag gag tcg gga cct ggc ctg gtg aaa cct tct cag    48
Asp Val Gln Leu Gln Glu Ser Gly Pro Gly Leu Val Lys Pro Ser Gln
1               5                   10                  15 tct ctg tcc ctc aca tgc act gtc act ggc tac tca atc acc agt gat    96
Ser Leu Ser Leu Thr Cys Thr Val Thr Gly Tyr Ser Ile Thr Ser Asp
                20                  25                  30 tat gcc tgg aat tgg atc cgg cag ttt cca gga aac aaa ctg gag tgg   144
Tyr Ala Trp Asn Trp Ile Arg Gln Phe Pro Gly Asn Lys Leu Glu Trp
            35                  40                  45 atg ggc tac ata agc ttc agt ggt tac act agt tac aac cca tct ctc   192
Met Gly Tyr Ile Ser Phe Ser Gly Tyr Thr Ser Tyr Asn Pro Ser Leu
            50                  55                  60 aaa agt cga atc tct gtc act cgg gac aca tcc agg aac caa ttc ttc   240
Lys Ser Arg Ile Ser Val Thr Arg Asp Thr Ser Arg Asn Gln Phe Phe
65                  70                  75                  80 ctc cag ttg act tct gtg act act gag gac aca gcc aca tat tac tgt   288
Leu Gln Leu Thr Ser Val Thr Thr Glu Asp Thr Ala Thr Tyr Tyr Cys
                85                  90                  95 gca aga gag gtc aac tat ggg gac tcc tac cac ttt gac tac tgg ggc   336
Ala Arg Glu Val Asn Tyr Gly Asp Ser Tyr His Phe Asp Tyr Trp Gly
                100                 105                 110 caa ggc acc att gtc aca gtc tcc tca                               363
Gln Gly Thr Ile Val Thr Val Ser Ser
            115                 120
```

FIG. 31L mV$_L$ MAb19

```
caa ctt gcg ctc act cag tca tct tca gcc tct ttc tcc ctg gga gcc    48
Gln Leu Ala Leu Thr Gln Ser Ser Ser Ala Ser Phe Ser Leu Gly Ala
1               5                   10                  15 tca gca aaa cta acg tgc act ttg agt agt caa cac aga acg tac acc    96
Ser Ala Lys Leu Thr Cys Thr Leu Ser Ser Gln His Arg Thr Tyr Thr
                20                  25                  30 att gaa tgg tat cag caa cag tca ctc aag cct cct aag tat gtg atg   144
Ile Glu Trp Tyr Gln Gln Gln Ser Leu Lys Pro Pro Lys Tyr Val Met
            35                  40                  45 gag gtt aag aaa gat gga agc cac agc aca ggt cat ggg att cct gat   192
Glu Val Lys Lys Asp Gly Ser His Ser Thr Gly His Gly Ile Pro Asp
    50                  55                  60 cgc ttc tct gga tcc agt tct ggt gct gat cgc tac ctc agc att tcc   240
Arg Phe Ser Gly Ser Ser Ser Gly Ala Asp Arg Tyr Leu Ser Ile Ser
65                  70                  75                  80 aac atc cag cct gaa gat gaa gca ata tac atc tgt ggt gtg ggt gat   288
Asn Ile Gln Pro Glu Asp Glu Ala Ile Tyr Ile Cys Gly Val Gly Asp
                85                  90                  95 gca att aag gga caa tct gtg ttt gtt ttc ggc ggt ggc acc aag gtc   336
Ala Ile Lys Gly Gln Ser Val Phe Val Phe Gly Gly Gly Thr Lys Val
                100                 105                 110 act gtc cta                                                        345
Thr Val Leu
        115
```

FIG. 32A hV$_H$ MAb3

Gln Val Gln Leu Val Gln Ser Gly Ala Glu Val Lys Lys Pro Gly Ala
1           5                   10                  15

Ser Val Lys Val Ser Cys Lys Ala Ser Gly Tyr Ile Phe Thr Ser Tyr
            20                  25                  30

Trp Val His Trp Val Arg Gln Ala Pro Gly Gln Arg Leu Glu Trp Met
            35                  40                  45

Gly Gly Phe Tyr Pro Gly Asn Ser Asp Ser Arg Tyr Ser Gln Lys Phe
        50                  55                  60

Gln Gly Arg Val Thr Ile Thr Arg Asp Thr Ser Ala Ser Thr Ala Tyr
65              70                  75                  80

Met Glu Leu Ser Ser Leu Arg Ser Glu Asp Thr Ala Val Tyr Tyr Cys
                85                  90                  95

Thr Arg Arg Asp Ser Pro Gln Tyr Trp Gly Gln Gly Thr Leu Val Thr
                100                 105                 110

Val Ser Ser
        115

FIG. 32B hV$_L$ MAb3

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Val His Ser
            20                  25                  30

Asn Gly Asn Thr Tyr Leu Glu Trp Phe Gln Gln Arg Pro Gly Gln Ser
            35                  40                  45

Pro Arg Arg Leu Ile Tyr Lys Val Ser Asn Arg Phe Ser Gly Val Pro
            50              55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Phe Thr Phe Gly Gly Gly Thr Lys Val Glu Ile Lys
            100                 105                 110
```

FIG. 32C hV$_H$ MAb4

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Ser Ser
            20                  25                  30

Trp Met His Trp Val Arg Gln Ala Pro Gly Gln Gly Leu Glu Trp Met
        35                  40                  45

Gly Ile Phe Leu Pro Gly Ser Gly Ser Thr Asp Tyr Ala Gln Lys Phe
    50                  55                  60

Gln Gly Arg Val Thr Met Thr Arg Asp Thr Ser Thr Ser Thr Val Tyr
65              70                  75                      80

Met Glu Leu Ser Ser Leu Arg Ser Glu Asp Thr Ala Val Tyr Tyr Cys
            85                  90                      95

Ala Thr Asp Gly Asn Tyr Asp Trp Phe Ala Tyr Trp Gly Gln Gly Thr
            100                 105                 110

Leu Val Thr Val Ser Ser
        115

FIG. 32D hV$_L$ MAb4

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Val His Ser
            20                  25                  30

Ser Gly Val Thr Tyr Leu Tyr Trp Tyr Leu Gln Lys Pro Gly Gln Ser
            35                  40                  45

Pro Gln Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Pro Thr Phe Gly Gln Gly Thr Lys Leu Glu Ile Lys
            100                 105                 110

FIG. 32E hV$_H$ MAb8(a)

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Thr Thr Tyr
            20                  25                  30

Ala Met Ser Trp Val Arg Gln Ala Pro Gly Lys Gly Leu Glu Trp Val
        35                  40                  45

Ser Ser Ile Ser Ser Gly Gly Thr Tyr Thr Tyr Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Thr Gln Gly Asn Tyr Ser Leu Asp Phe Trp Gly Gln Gly Thr Thr
            100                 105                 110

Val Thr Val Ser Ser
        115
```

FIG. 32F hV$_L$ MAb8(a)

Asp Ile Val Met Thr Gln Ser Pro Leu Ser Leu Pro Val Thr Pro Gly
1              5                    10                  15

Glu Pro Ala Ser Ile Ser Cys Arg Ser Ser Lys Ser Leu Arg His Thr
              20                  25              30

Lys Gly Ile Thr Phe Leu Tyr Trp Tyr Leu Gln Lys Pro Gly Gln Ser
        35                  40                  45

Pro Gln Leu Leu Ile Tyr Gln Met Ser Asn Arg Ala Ser Gly Val Pro
        50                  55                  60

Asp Arg Phe Ser Gly Ser Gly Ser Gly Thr Asp Phe Thr Leu Lys Ile
65              70                  75                      80

Ser Arg Val Glu Ala Glu Asp Val Gly Val Tyr Tyr Cys Ala Gln Asn
                85                  90                  95

Leu Glu Leu Pro Leu Thr Phe Gly Gly Gly Thr Lys Val Glu Ile Lys
            100                 105                 110

FIG. 32G hV$_H$ MAb8(b)

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Thr Thr Tyr
            20                  25                  30

Ala Met Asn Trp Val Arg Gln Ala Pro Gly Lys Gly Leu Glu Trp Val
        35                  40                  45

Ser Ser Ile Ser Ser Gly Gly Thr Tyr Thr Tyr Tyr Ala Asp Ser Val
        50                  55                  60

Lys Gly Arg Phe Thr Ile Ser Arg Asp Asn Ala Lys Asn Ser Leu Tyr
65              70                  75                  80

Leu Gln Met Asn Ser Leu Arg Ala Glu Asp Thr Ala Val Tyr Tyr Cys
                85                  90                  95

Ala Thr Gln Gly Asn Tyr Ser Leu Asp Phe Trp Gly Gln Gly Thr Thr
            100                 105                 110

Val Thr Val Ser Ser
        115

FIG. 32H hV$_L$ MAb8(b)

Asp Ile Val Met Thr Gln Ser Pro Leu Ser Leu Pro Val Thr Pro Gly
1              5                   10                  15

Glu Pro Ala Ser Ile Ser Cys Arg Ser Ser Lys Ser Leu Arg His Thr
            20                  25                  30

Lys Gly Ile Thr Phe Leu Asp Trp Tyr Leu Gln Lys Pro Gly Gln Ser
            35                  40                  45

Pro Gln Leu Leu Ile Tyr Gln Met Ser Asn Arg Ala Ser Gly Val Pro
        50              55                  60

Asp Arg Phe Ser Gly Ser Gly Ser Gly Thr Asp Phe Thr Leu Lys Ile
65              70                  75                      80

Ser Arg Val Glu Ala Glu Asp Val Gly Val Tyr Tyr Cys Ala Gln Asn
                85                  90                  95

Leu Glu Leu Pro Leu Thr Phe Gly Gly Gly Thr Lys Val Glu Ile Lys
            100                 105                 110

FIG. 32I hV$_H$ MAb8(c)

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Thr Thr Tyr
            20                  25                  30

Ala Met Ser Trp Val Arg Gln Ala Pro Gly Lys Gly Leu Glu Trp Val
        35                  40                  45

Ser Thr Ile Ser Ser Gly Gly Thr Tyr Thr Tyr Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Thr Gln Gly Asn Tyr Ser Leu Asp Phe Trp Gly Gln Gly Thr Thr
                100                 105                 110

Val Thr Val Ser Ser
        115

FIG. 32J hV$_L$ MAb8(c)

Asp Ile Val Met Thr Gln Ser Pro Leu Ser Leu Pro Val Thr Pro Gly
1            5                    10                  15

Glu Pro Ala Ser Ile Ser Cys Arg Ser Ser Lys Ser Leu Arg His Thr
            20                  25                  30

Lys Gly Ile Thr Phe Leu Tyr Trp Tyr Leu Gln Lys Pro Gly Gln Ser
            35                  40                  45

Pro Gln Leu Leu Ile Tyr Gln Met Ser Asn Arg Ala Ser Gly Val Pro
            50              55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Leu Thr Phe Gly Gly Gly Thr Lys Val Glu Ile Lys
            100                 105                 110

FIG. 32K hV_H MAb13(a)

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ile Phe Ser Ser Tyr
            20                  25                  30

Gly Met Ser Trp Val Arg Gln Ala Pro Gly Lys Gly Leu Glu Trp Val
        35                  40                  45

Ala Asn Ile Asn Thr Phe Gly Asp Arg Thr Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Arg Gly Thr Gly Thr Tyr Trp Gly Gln Gly Thr Leu Val Thr Val
            100                 105                 110

Ser Ser

FIG. 32L hV$_L$ MAb13(a)

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu Asp Ser
            20                  25                  30

Asp Gly Lys Thr Tyr Leu Asn Trp Phe Gln Gln Arg Pro Gly Gln Ser
            35                  40                  45

Pro Arg Arg Leu Ile Tyr Leu Val Ser Asn Arg Asp Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Gln Thr Phe Gly Gly Thr Lys Val Glu Ile Lys
            100                 105                 110

FIG. 32M hV_H MAb13(b)

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ile Phe Ser Ser Tyr
            20                  25                  30

Gly Met Ser Trp Val Arg Gln Ala Pro Gly Lys Gly Leu Glu Trp Val
            35                  40                  45

Ala Ser Ile Asn Thr Phe Gly Asp Arg Thr Tyr Tyr Val Asp Ser Val
            50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Arg Gly Thr Gly Thr Tyr Trp Gly Gln Gly Thr Leu Val Thr Val
            100                 105                 110

Ser Ser
```

FIG. 32N hV$_L$ MAb13(b)

Asp Val Val Met Thr Gln Ser Pro Leu Ser Leu Pro Val Thr Leu Gly
1           5                   10                  15

Gln Pro Ala Ser Ile Ser Cys Arg Ser Ser Gln Ser Leu Leu Asp Ser
            20                  25                  30

Asp Gly Lys Thr Tyr Leu Asn Trp Phe Gln Gln Arg Pro Gly Gln Ser
            35                  40                  45

Pro Arg Arg Leu Ile Tyr Leu Val Ser Lys Arg Asp Ser Gly Val Pro
            50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
            85                  90                  95

Thr His Phe Pro Gln Thr Phe Gly Gly Gly Thr Lys Val Glu Ile Lys
            100                 105                 110

FIG. 32O hV$_H$ MAb16(a)

Gln Val Gln Leu Val Gln Ser Gly Ala Glu Val Lys Lys Pro Gly Ala
1           5               10              15

Ser Val Lys Val Ser Cys Lys Ala Ser Gly Tyr Thr Phe Thr Ser Tyr
         20              25              30

Tyr Met Tyr Trp Val Arg Gln Ala Pro Gly Gln Gly Leu Glu Trp Met
     35              40              45

Gly Ile Ile Asn Pro Ser Asn Gly Gly Thr Ser Tyr Ala Gln Lys Phe
    50              55              60

Gln Gly Arg Val Thr Met Thr Arg Asp Thr Ser Thr Ser Thr Val Tyr
65          70              75              80

Met Glu Leu Ser Ser Leu Arg Ser Glu Asp Thr Ala Val Tyr Tyr Cys
             85              90              95

Thr Arg Gly Gly Tyr Tyr Pro Phe Asp Tyr Trp Gly Gln Gly Thr Thr
             100             105             110

Val Thr Val Ser Ser
         115

FIG. 32P hV$_L$ MAb16(a)

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu Asp Ser
            20                  25                  30

Asp Gly Lys Thr Tyr Leu Tyr Trp Phe Gln Gln Arg Pro Gly Gln Ser
        35                  40                  45

Pro Arg Arg Leu Ile Tyr Leu Val Ser Asn Arg Asp Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
            85                  90                  95

Thr His Ser Pro Tyr Thr Phe Gly Gln Gly Thr Lys Leu Glu Ile Lys
            100                 105                 110

FIG. 32Q hV$_H$ MAb16(b)

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Asn Gly Gly Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Thr Arg Gly Gly Tyr Tyr Pro Phe Asp Tyr Trp Gly Gln Gly Thr Thr
                100                 105                 110

Val Thr Val Ser Ser
        115

FIG. 32R hV_L MAb16(b)

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu Asp Ser
            20                  25                  30

Asp Gly Lys Thr Tyr Leu Asn Trp Phe Gln Gln Arg Pro Gly Gln Ser
        35                  40                  45

Pro Arg Arg Leu Ile Tyr Leu Val Ser Asn Arg Asp Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
            85                  90                  95

Thr His Ser Pro Tyr Thr Phe Gly Gln Gly Thr Lys Leu Glu Ile Lys
            100                 105                 110

FIG. 32S hV<sub>H</sub> MAb16(c)

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met Tyr Trp Val Arg Gln Ala Pro Gly Gln Gly Leu Glu Trp Met
        35                  40                  45

Gly Glu Ile Asn Pro Ser Asn Gly Gly Thr Asn Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Thr Arg Gly Gly Tyr Tyr Pro Phe Asp Tyr Trp Gly Gln Gly Thr Thr
            100                 105                 110

Val Thr Val Ser Ser
        115
```

FIG. 32T hV$_L$ MAb16(c)

Asp Val Val Met Thr Gln Ser Pro Leu Ser Leu Pro Val Thr Leu Gly
1           5                   10                  15

Gln Pro Ala Ser Ile Ser Cys Arg Ser Ser Gln Ser Leu Leu Asp Ser
            20                  25                  30

Asp Gly Lys Thr Tyr Leu Tyr Trp Phe Gln Gln Arg Pro Gly Gln Ser
            35                  40                  45

Pro Arg Arg Leu Ile Tyr Leu Val Ser Glu Arg Asp Ser Gly Val Pro
            50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
            85                  90                  95

Thr His Ser Pro Tyr Thr Phe Gly Gln Gly Thr Lys Leu Glu Ile Lys
            100                 105                 110

FIG. 32U hV$_H$ MAb19(a)

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Asp
            20                  25                  30

Tyr Ala Trp Asn Trp Ile Arg Gln His Pro Gly Lys Gly Leu Glu Trp
            35                  40                  45

Ile Gly Tyr Ile Ser Phe Ser Gly Tyr Thr Tyr Tyr Asn Pro Ser Leu
            50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Glu Val Asn Tyr Gly Asp Ser Tyr His Phe Asp Tyr Trp Gly
            100                 105                 110

Gln Gly Thr Leu Val Thr Val Ser Ser
            115                 120

FIG. 32V hV_L MAb19(a)

Gln Leu Val Leu Thr Gln Ser Pro Ser Ala Ser Ala Ser Leu Gly Ala
1              5                  10                 15

Ser Val Lys Leu Thr Cys Thr Leu Ser Ser Gln His Arg Thr Tyr Thr
              20                  25                 30

Ile Glu Trp His Gln Gln Pro Glu Lys Gly Pro Arg Tyr Leu Met
         35                  40                 45

Lys Val Lys Lys Asp Gly Ser His Ser Lys Gly Asp Gly Ile Pro Asp
     50                  55                  60

Arg Phe Ser Gly Ser Ser Ser Gly Ala Glu Arg Tyr Leu Thr Ile Ser
65             70                  75                       80

Ser Leu Gln Ser Glu Asp Glu Ala Asp Tyr Tyr Cys Gly Val Gly Asp
                  85                  90                  95

Ala Ile Lys Gly Gln Ser Val Phe Val Phe Gly Gly Gly Thr Lys Val
              100                 105                 110

Glu Ile Lys
         115

FIG. 32W hV$_H$ MAb19(b)

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Asp
            20                  25                  30

Tyr Ala Trp Ser Trp Ile Arg Gln His Pro Gly Lys Gly Leu Glu Trp
        35                  40                  45

Ile Gly Tyr Ile Ser Phe Ser Gly Tyr Thr Tyr Tyr Asn Pro Ser Leu
        50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Glu Val Asn Tyr Gly Asp Ser Tyr His Phe Asp Tyr Trp Gly
            100                 105                 110

Gln Gly Thr Leu Val Thr Val Ser Ser
            115                 120

FIG. 32X hV<sub>L</sub> MAb19(b)

```
Gln Leu Val Leu Thr Gln Ser Pro Ser Ala Ser Ala Ser Leu Gly Ala
1               5                   10                  15

Ser Val Lys Leu Thr Cys Thr Leu Ser Ser Gln His Arg Thr Tyr Thr
                20                  25                  30

Ile Ala Trp His Gln Gln Pro Glu Lys Gly Pro Arg Tyr Leu Met
            35                  40                  45

Lys Val Lys Lys Asp Gly Ser His Ser Lys Gly Asp Gly Ile Pro Asp
        50                  55                  60

Arg Phe Ser Gly Ser Ser Ser Gly Ala Glu Arg Tyr Leu Thr Ile Ser
65                  70                  75                  80

Ser Leu Gln Ser Glu Asp Glu Ala Asp Tyr Tyr Cys Gly Val Gly Asp
                85                  90                  95

Ala Ile Lys Gly Gln Ser Val Phe Val Phe Gly Gly Gly Thr Lys Val
            100                 105                 110

Glu Ile Lys
        115
```

FIG. 32Y hV$_H$ MAb19(c)

Gln Val Gln Leu Gln Glu Ser Gly Pro Gly Leu Val Lys Pro Ser Gln
1               5               10              15

Thr Leu Ser Leu Thr Cys Thr Val Ser Gly Tyr Ser Ile Thr Ser Asp
            20              25              30

Tyr Ala Trp Asn Trp Ile Arg Gln His Pro Gly Lys Gly Leu Glu Trp
        35              40              45

Ile Gly Tyr Ile Ser Phe Ser Gly Tyr Thr Ser Tyr Asn Pro Ser Leu
    50              55              60

Lys Ser Arg Val Thr Ile Ser Val Asp Thr Ser Lys Asn Gln Phe Ser
65              70              75              80

Leu Lys Leu Ser Ser Val Thr Ala Ala Asp Thr Ala Val Tyr Tyr Cys
            85              90              95

Ala Arg Glu Val Asn Tyr Gly Asp Ser Tyr His Phe Asp Tyr Trp Gly
            100             105             110

Gln Gly Thr Leu Val Thr Val Ser Ser
        115             120

FIG. 32Z hV$_L$ MAb19(c)

```
Gln Leu Val Leu Thr Gln Ser Pro Ser Ala Ser Ala Ser Leu Gly Ala
1               5                   10                  15

Ser Val Lys Leu Thr Cys Thr Leu Ser Ser Gln His Arg Thr Tyr Thr
            20                  25                  30

Ile Glu Trp His Gln Gln Pro Glu Lys Gly Pro Arg Tyr Leu Met
        35                  40                  45

Glu Val Lys Lys Asp Gly Ser His Ser Lys Gly Asp Gly Ile Pro Asp
    50                  55                  60

Arg Phe Ser Gly Ser Ser Ser Gly Ala Glu Arg Tyr Leu Thr Ile Ser
65                  70                  75                  80

Ser Leu Gln Ser Glu Asp Glu Ala Asp Tyr Tyr Cys Gly Val Gly Asp
                85                  90                  95

Ala Ile Lys Gly Gln Ser Val Phe Val Phe Gly Gly Thr Lys Val
            100                 105                 110

Glu Ile Lys
        115
```

METHODS FOR TREATING COLORECTAL CANCER

1. CROSS REFERENCE TO RELATED APPLICATIONS

This application claims the benefit under 35 U.S.C. §119 (e) of provisional application No. 61/293,612, filed 8 Jan. 2010, and of provisional application No. 61/367,855, filed 26 Jul. 2010, the contents of all which are incorporated herein by reference in their entirety.

2. REFERENCE TO SEQUENCE LISTING, TABLE OR COMPUTER PROGRAM

The Sequence Listing concurrently submitted herewith under 37 CFR §1.821 in a computer readable form (CRF) via EFS-Web as file name BR002SEQLIST.txt is incorporated herein by reference. The electronic copy of the Sequence Listing was created on 30 Dec. 2010, with a file size of 79 KBytes.

3. FIELD OF INVENTION

The present disclosure is directed to, among other things, methods of treating and preventing colorectal cancer metastasis and recurrence by administering a composition comprising an antibody specific for progastrin.

4. BACKGROUND

Despite decades of basic and clinical research, colorectal cancer remains one of mankind's most deadly non-communicable diseases. According to the GLOBOCAN Project of the World Health Organization's International Agency for Research on Cancer, it was estimated that in 2008 the incidence of colorectal cancer was over 1.2 million and that in the same year more than 600 thousand people were killed by the disease. While much has been learned recently regarding how colorectal cancer works at the molecular level, clinicians still rely on therapeutic modalities such as surgery, radiation and chemotherapy that would have been familiar to oncologists of a generation ago. Early diagnosis, made possible by advances in imaging technology and molecular diagnostics, factors greatly in the success of any treatment. Although the efficacy of all these treatments has improved over the years, the improvement in cure rates and the increase in longevity have been incremental. Even the new targeted therapies resulting from the revolution in molecular oncology have, for the most part, improved outcomes only modestly.

Two of the most challenging aspects of managing colorectal cancer patients are metastasis and recurrence.

Metastasis occurs when the colorectal cancer spreads to distant organs from the primary tumor. While it is often possible to resect the primary tumor, it is the metastases that frequently end up killing the patient because they become too numerous or entwined with healthy host tissue to treat surgically. According to the American Cancer Society, the five year survival rate in the United States for patients diagnosed with Stage IIIC colon cancer between 1998 and 2000 was 28%, which dropped to only 6% at Stage IV (i.e., metastatic colorectal cancer).

Recurrence is the phenomenon by which colorectal cancer returns after initially responding to treatment and apparently disappearing. Apart from the emotional toll inflicted on patients and their families, recurrence is problematic because the returning cancer may be less responsive to the therapy or therapies that were effective to fight the first cancer. For other patients, prior treatments for the first cancer may have caused irreversible side effects, such as cardiac or neurological damage. In such patients, the risks of using the same therapy to fight the recurrent cancer may be too great. Under these circumstances, a patient may have fewer treatment options with a concomitantly greater risk of mortality.

While improvements in radiation treatment, chemotherapy and the advent of targeted therapies have increased the longevity of patients stricken by colorectal cancer, many such patients continue to die within months to a few years after their diagnosis. An urgent need therefore exists for new treatments effective against metastatic colorectal cancer and recurrence of colorectal cancer.

5. SUMMARY

The present disclosure provides methods useful for treating patients in need of treatment for metastatic colorectal cancer by administering a therapeutically effective amount of a composition comprising antibodies that specifically bind progastrin. In some embodiments, the metastatic colorectal cancer to be treated is located in the liver, lung, brain or lymph nodes.

In some other embodiments, it is useful to treat a patient by administering the anti-progastrin antibody composition before surgical resection of metastatic colorectal cancer. In other embodiments, it is useful to treat such patients by administering the antibody composition after surgical resection of such tumors.

In some embodiments, it is useful to treat a patient by administering the anti-progastrin antibody composition before giving radiation therapy to the patient. In other embodiments, it is useful to treat such patients by administering the antibody composition after radiation therapy.

In some other embodiments, it is useful to treat a patient by administering the anti-progastrin antibody composition before, concurrently with or after a chemotherapeutic agent. Useful chemotherapeutic agents for this purpose, include, but are not limited to folate antagonists, purine antagonists, pyrimidine antagonists, DNA alkylating agents, DNA cross-linking drugs, antibiotics, platinum complexes, proteasome inhibitors, mitotic spindle poisons, topoisomerase inhibitors, tyrosine kinase inhibitors, and others.

In some embodiments, it is useful to treat a patient by administering the anti-progastrin antibody composition before, concurrently with or after a different type of antibody with efficacy against metastatic colorectal cancer. Such antibodies include, but are not limited to antibodies that target EGFR, such as cetuximab or panitumumab, and antibodies that target VEGF, such as bevacizumab.

For use in the methods of treating metastatic colorectal cancer, therapeutic antibodies may be effective to reduce the proliferation or increase the differentiation or rate of cell death of metastatic colorectal cancer cells, reduce the average number or size of colorectal metastases, or reduce the blood concentration of progastrin in treated patients.

Antibody compositions for use in the methods of the disclosure can be prepared as different formulations, including, but not limited to, an aqueous suspension, for administration by a variety of routes, including, but not limited to, parenteral administration, intrathecal administration, subcutaneous administration, intravenous administration, intramuscular administration, intraperitoneal administration, infusion administration, or bolus administration. In some embodiments, the composition is formulated for parenteral administration, and in some specific embodiments, intravenous injection by infusion.

In some embodiments, an effective dose the anti-progastrin antibodies of the disclosure ranges from 0.001 mg/kg to about 250 mg/kg, which may be given in one administration, or over multiple, spaced administrations.

The disclosure also provides pharmaceutical kits for use by clinicians and others to facilitate administration of anti-progastrin antibody compositions to patients. In some embodiments, kits include an anti-progastrin antibody of the disclosure in either lyophilized form or as an aqueous solution, a diluent, such as pharmaceutical grade water or buffer, and a device for administering the anti-progastrin antibody, such as a syringe and needle. In other embodiments, kits may additionally include a second therapeutic agent, such as, but not limited to, the chemotherapeutic agents of the disclosure, a second anti-progastrin antibody of the disclosure, or others.

Methods are also provided for preventing metastatic colorectal cancer by administering to a patient in need of prevention of metastatic colorectal cancer a composition comprising an antibody that specifically binds to progastrin in an amount effective to prevent metastatic colorectal cancer. In a number of embodiments, the antibodies of the composition are effective to reduce the proliferation or increase the differentiation or rate of cell death of metastatic colorectal cancer cells, or reduce the blood concentration of progastrin in treated patients.

In some embodiments, the composition can be administered before or after surgery or radiation therapy for primary colorectal cancer, or concurrently with or after administration of a chemotherapeutic agent effective to prevent metastatic colorectal cancer. The composition can also be administered concurrently with or after a second therapeutic antibody effective to prevent metastatic colorectal cancer having specificity other than for progastrin.

Methods are also provided for preventing recurrence of colorectal cancer by administering to a patient in need of prevention of recurrence of colorectal cancer a composition comprising an antibody that specifically binds to progastrin in an amount effective to prevent recurrence of colorectal cancer. In certain of these methods, the patient previously underwent treatment for colorectal cancer, such as surgery, radiation therapy, biological therapy, immunotherapy and chemotherapy, after which the colorectal cancer apparently disappeared.

In a number of embodiments, the antibodies of the composition are effective to reduce the proliferation or increase the differentiation or rate of cell death of metastatic colorectal cancer cells, or reduce the blood concentration of progastrin in treated patients. In other embodiments, the composition can be administered concurrently with or after a second therapeutic agent effective to prevent metastatic colorectal cancer including, for example, an antibody having specificity other than for progastrin.

Methods are also provided for inhibiting the growth of a colorectal cancer stem cell in a patient by administering to a patient in need of inhibition of growth of a colorectal cancer stem cell a composition comprising an antibody that specifically binds to progastrin in an amount effective to inhibit said colorectal cancer stem cell.

In a number of embodiments, the antibodies of the composition are effective to reduce the proliferation or increase the differentiation or rate of cell death of colorectal cancer stem cells, or reduce the blood concentration of progastrin in treated patients. In other embodiments, the composition can be administered concurrently with or after a second therapeutic agent effective to inhibit the growth of colorectal cancer stem cells, for example, an antibody having specificity other than for progastrin.

Methods are also provided for monitoring the efficacy of a treatment for metastatic colorectal cancer in a patient, such as chemotherapy, biological therapy, immunotherapy or antibody therapy, by determining the concentration of progastrin in a first sample, such as a bodily fluid or biopsy of metaststic colorectal cancer, obtained from a patient before treatment for metastatic colorectal cancer, and then comparing the concentration of progastrin in the first sample to that in a second sample obtained from the same patient after treatment, where a reduction in the concentration of progastrin in said second sample compared to said first sample indicates that the treatment was effective.

In some embodiments of the method an assay, such as an RIA or ELISA, employing an antibody specific for progastrin is used to determine the concentration of progastrin in the first and second samples.

Methods are also provided for diagnosing the presence of colorectal cancer in a patient by determining the concentration of progastrin in a sample, such as a bodily fluid, obtained from a patient suspected of having colorectal cancer and then comparing the concentration of progastrin in the sample to a predetermined value where an elevated level of progastrin in the sample compared to the predetermined value indicates the presence of colorectal cancer in the patient. In some embodiments, the predetermined value is based on an average of sample values obtained when the patient was known to be free of colorectal cancer and in others the predetermined value is based on a population average.

In some embodiments of the method, the patient was formerly treated for colorectal cancer and is in remission at the time the sample is obtained. In other embodiments, the method includes the additional step of performing a second diagnostic test on the patient to confirm the presence of colorectal cancer including, for example, a blood test, a medical imaging test or a genetic test. In some embodiments the blood test is to detect carcinoembryonic antigen and in other embodiments, the genetic test is to detect mutations in the adenomatous polyposis coli (APC) gene. In yet other embodiments, an assay such as an RIA or ELISA employing an antibody specific for progastrin is used to determine the concentration of progastrin in the sample.

Many different types of antibodies that specifically bind to progastrin can be effective for treating metastatic colorectal cancer. This includes, but is not limited to, polyclonal antibodies, monoclonal antibodies, which may be humanized, as well as chimeric antibodies, antibodies having the isotypes of IgA1, IgA2, IgD, IgE, IgG1, IgG2, IgG3, IgG4, and IgM, and single chain antibodies. In some other embodiments, antibodies useful for the methods of the disclosure include antibodies conjugated to moieties that usefully alter their function or characteristics, for example, but not limited to, increasing serum half life. In yet other embodiments, amino acid changes can be effected for a similar purpose, or other purposes.

In some embodiments, the antibodies recognize just one epitope of progastrin. In other embodiments, mixtures of antibodies specific for different epitopes of progastrin can be used.

Antibodies for use in the methods of treating metastatic colorectal cancer can have a range of binding affinities for progastrin, for example, about 5000 nM, or even higher, for example, at least about 4000 nM, 3000 nM, 2000 nM, 1000 nM, 900 nM, 800 nM, 700 nM, 600 nM, 500 nM, 400 nM, 300 nM, 200 nM, 100 nM, 90 nM, 80 nM, 70 nM, 60 nM, 50 nM, 40 nM, 30 nM, 25 nM, 20 nM, 15 nM, 10 nM, 7 nM, 6 nM, 5 nM, 4 nM, 3 nM, 2 nM, 1 nM, 0.1 nM, 0.01 nM or 0.001 nM.

In certain embodiments of the disclosed methods, monoclonal antibodies as disclosed herein may be used including, for example, MAb1, MAb2, MAb3, MAb4, MAb5, MAb6, MAb7, MAb8, MAb9, MAb10, MAb11, MAb12, MAb13, MAb14, MAb15, MAb16, MAb17, MAb18, MAb19, MAb20, MAb21, MAb22, MAb23, or others.

In other embodiments of the disclosed methods, monoclonal antibodies as disclosed herein may be used including, for example, monoclonal antibodies having a heavy chain variable region ($V_H$) in which the first CDR is selected from $V_H$ CDR 1.3, $V_H$ CDR 1.4, $V_H$ CDR 1.8, $V_H$ CDR 1.13, $V_H$ CDR 1.16, $V_H$ CDR 1.19, the second CDR is selected from $V_H$ CDR 2.3, $V_H$ CDR 2.4, $V_H$ CDR 2.8, $V_H$ CDR 2.13, $V_H$ CDR 2.16, $V_H$ CDR 2.19, and the third CDR is selected from $V_H$ CDR 3.3, $V_H$ CDR 3.4, $V_H$ CDR 3.8, $V_H$ CDR 3.13, $V_H$ CDR 3.16, $V_H$ CDR 3.19. The particular sequences of these CDRs are described below. Other useful antibodies have a light chain region ($V_L$) in which the first CDR is selected from $V_L$ CDR 1.3, $V_L$ CDR 1.4, $V_L$ CDR 1.8, $V_L$ CDR 1.13, $V_L$ CDR 1.16, $V_L$ CDR 1.19, the second CDR is selected from $V_L$ CDR 2.3, $V_L$ CDR 2.4, $V_L$ CDR 2.8, $V_L$ CDR 2.13, $V_L$ CDR 2.16, $V_L$ CDR 2.19, and the third CDR is selected from $V_L$ CDR 3.3, $V_L$ CDR 3.4, $V_L$ CDR 3.8, $V_L$ CDR 3.13, $V_L$ CDR 3.16, $V_L$ CDR 3.19. The particular sequences of these CDRs are also described below.

6. BRIEF DESCRIPTION OF THE FIGURES

FIG. 1 provides a graph comparing gastrin gene expression levels among different human primary and metastatic colorectal cancer cell lines.

Figure 2:
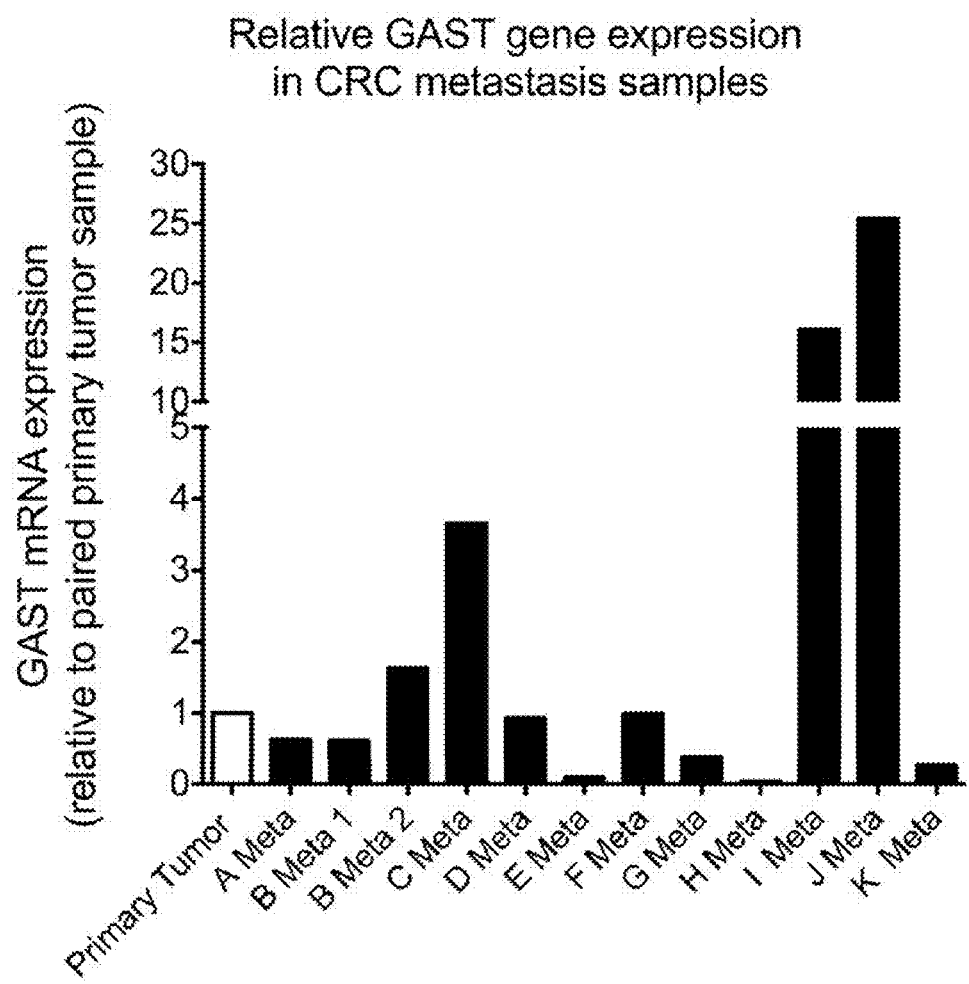

FIG. 2 provides a graph comparing the relative gastrin gene expression levels in metastatic colorectal tumors from each of 11 different patients. Expression levels in the metastatic colorectal tumor(s) from each patient were normalized to the expression level in the matched primary colorectal tumor from the same patient.

Figure 3:
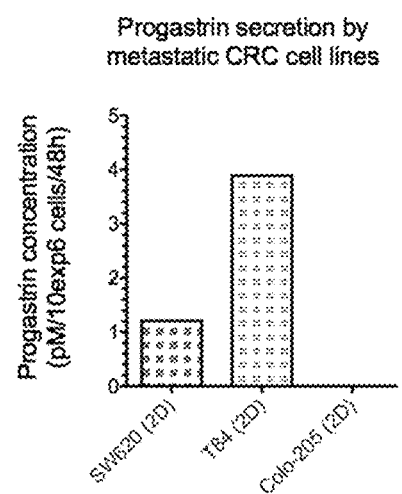

FIG. 3 provides a graph comparing the amount of progastrin secreted into the growth medium by three different metastatic colorectal cancer cell lines.

Figure 4:
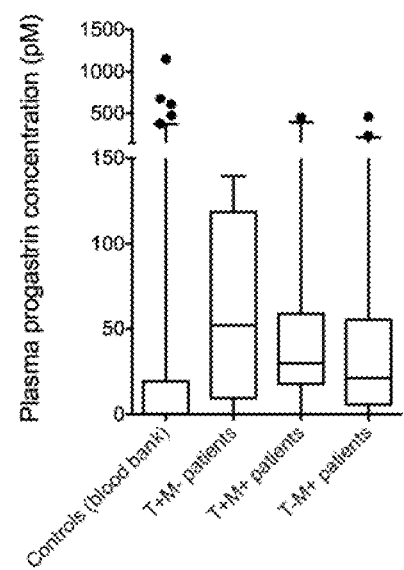

FIG. 4 provides a graph showing plasma or serum progastrin concentrations in patients with primary colorectal cancer, metastatic colorectal cancer, and metastatic colorectal cancer from whom the primary tumor was resected, compared to healthy controls.

Figure 5:
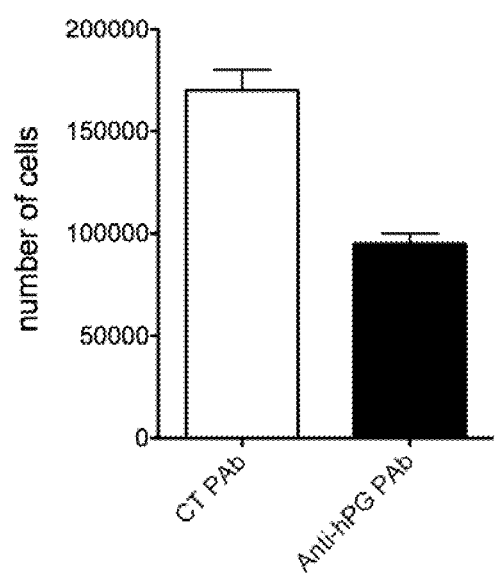

FIG. 5 provides a graph comparing the effect of control and anti-hPG polyclonal antibodies on the growth of SW620 metastatic colorectal cancer cells in culture.

FIG. 6A provides a graph comparing the effect of control and four different anti-hPG monoclonal antibodies (MAb1-MAb4) on the growth of SW620 metastatic colorectal cancer cells in culture.

Figure 6B:
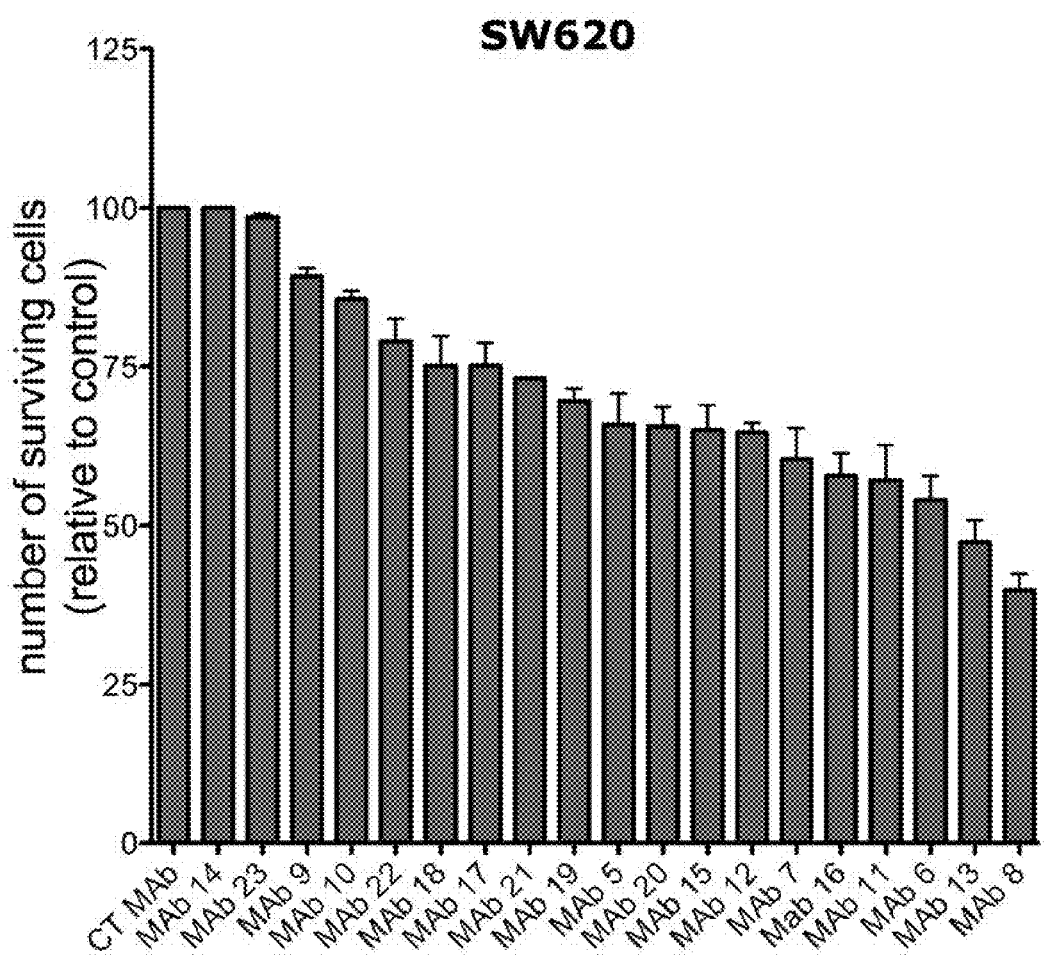

FIG. 6B provides a graph comparing the effect on the growth of SW620 metastatic colorectal cancer cells in culture of treatment with 19 different anti-hPG monoclonal antibodies (MAb5-MAb23) compared to a control antibody.

Figure 7:
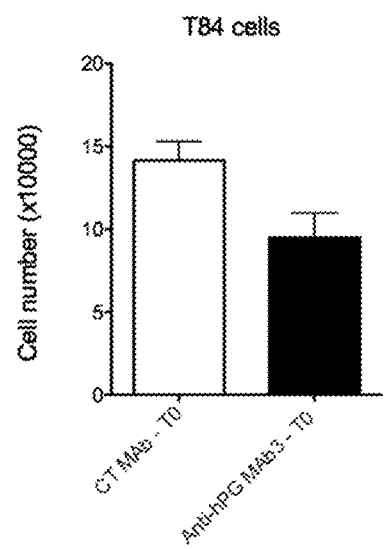

FIG. 7 provides a graph comparing the effect of control and an anti-hPG monoclonal antibody on the growth of T84 metastatic colorectal cancer cells in culture.

Figure 8A:
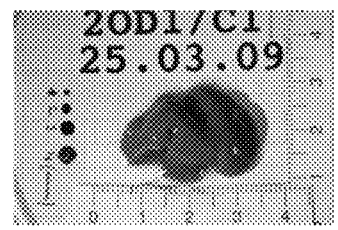

FIG. 8A provides a photograph of a liver in which no visible metastases are present removed from a nude mouse treated with anti-hPG polyclonal antibodies. SW620 cells were injected into the spleens of nude mice, and then treated for six weeks with anti-hPG polyclonal antibodies, a control polyclonal antibody or phosphate buffered saline.

Figure 8B:
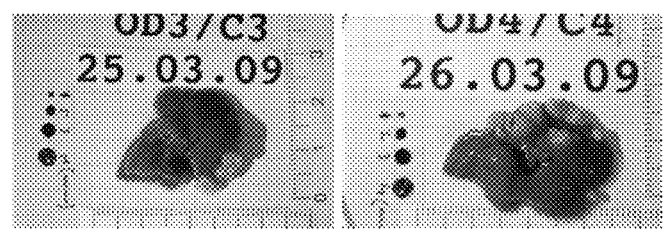

FIG. 8B provides photographs of livers with visible metastases removed from a nude mouse treated with a control polyclonal antibody. SW620 cells were injected into the spleens of nude mice, and then treated for six weeks with anti-hPG polyclonal antibodies, a control polyclonal antibody or phosphate buffered saline.

Figure 9:
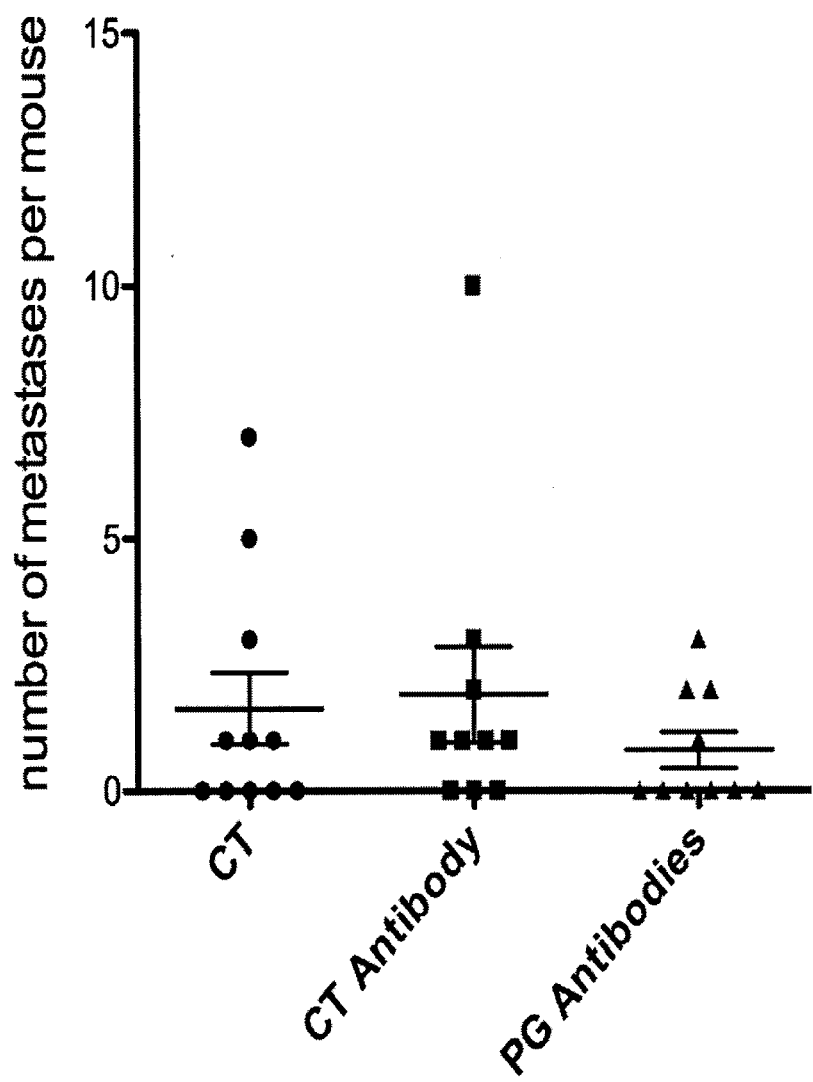

FIG. 9 provides a graph comparing the number of visible liver metastases formed after SW620 cells were injected into the spleens of nude mice, and then treated for six weeks with anti-hPG polyclonal antibodies, a control polyclonal antibody or phosphate buffered saline.

Figure 10:
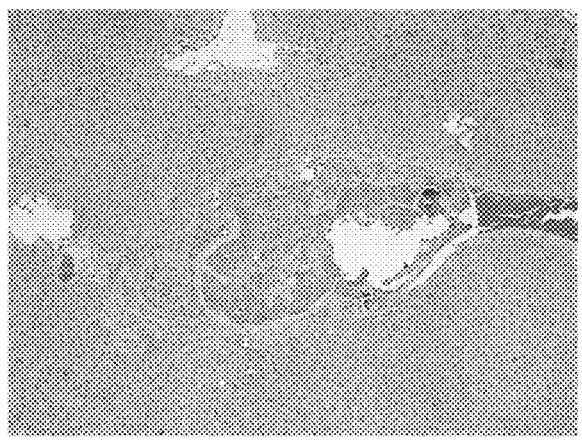

FIG. 10 provides a photomicrograph of an exemplary liver micrometastasis formed after SW620 cells were injected into the spleens of control nude mice, and then treated for six weeks with control polyclonal antibodies or phosphate buffered saline.

Figure 11:
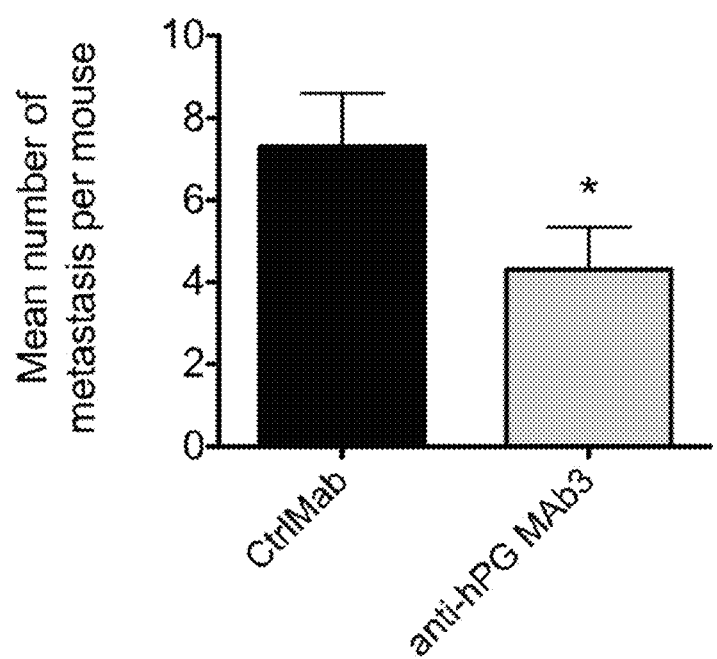

FIG. 11 provides a graph comparing the number of visible liver metastases formed after SW620 cells were injected into the spleens of nude mice, and then treated for six weeks with anti-hPG monoclonal antibodies versus a control antibody.

Figure 12:
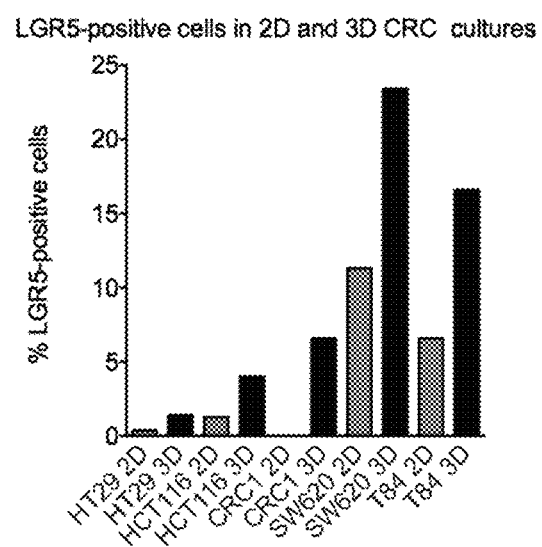

FIG. 12 provides a graph demonstrating the effect of growth under low adherence culture conditions on expression of the stem cell marker LGR5 by primary and metastatic colorectal cancer cell lines, as well as cells obtained from a biopsy sample of primary human colorectal cancer.

Figure 13:
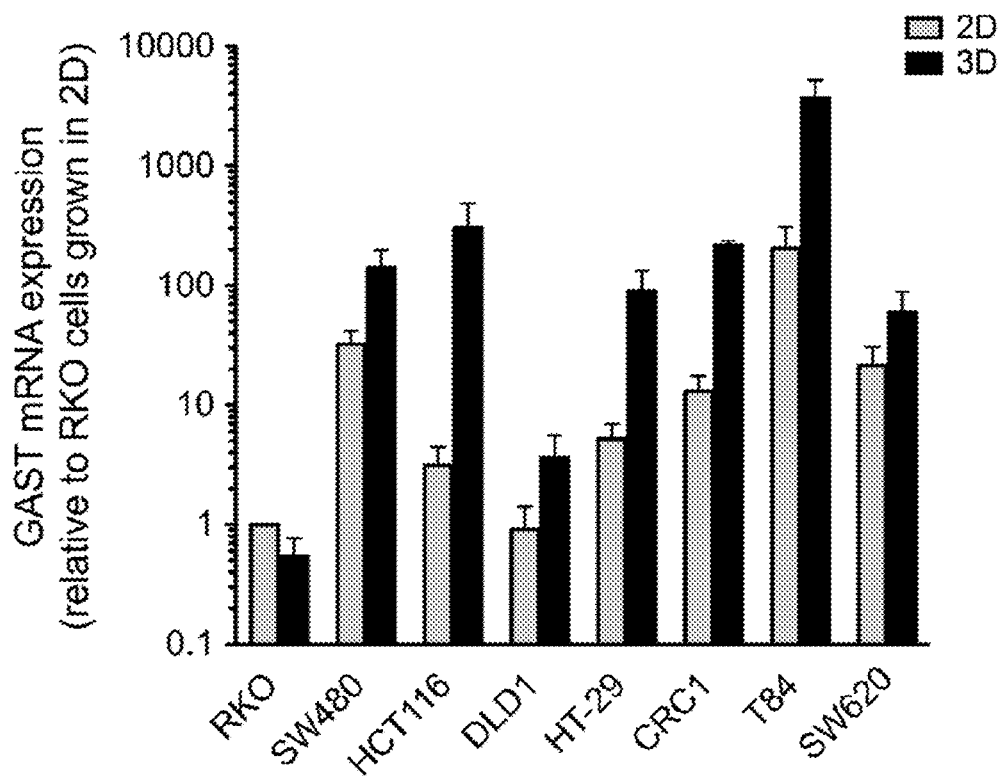

FIG. 13 provides a graph demonstrating the effect of growth under low adherence culture conditions on the amount of gastrin mRNA expressed by primary and metastatic colorectal cancer cell lines, as well as cells obtained from a biopsy sample of primary human colorectal cancer.

Figure 14:
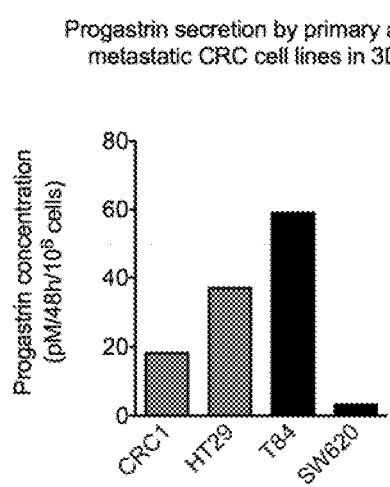

FIG. 14 provides a graph demonstrating the amount of progastrin secreted into the medium by primary and metastatic colorectal cancer cell lines, as well as cells obtained from a biopsy sample of primary human colorectal cancer, grown under low adherence culture conditions.

Figure 15:
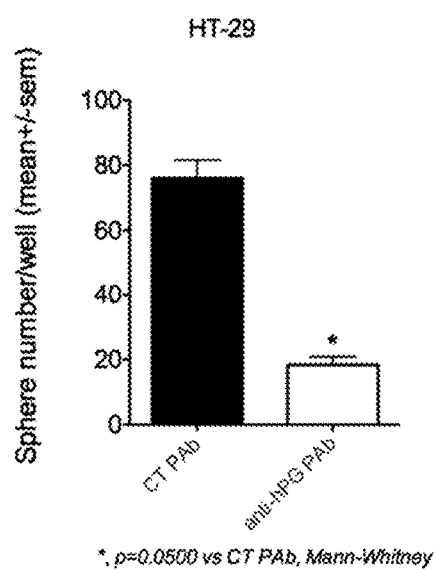

FIG. 15 provides a graph demonstrating the effect of anti-progastrin polyclonal antibodies on formation of spheroids by HT-29 primary colorectal cancer cells grown under low adherence culture conditions.

Figure 16:
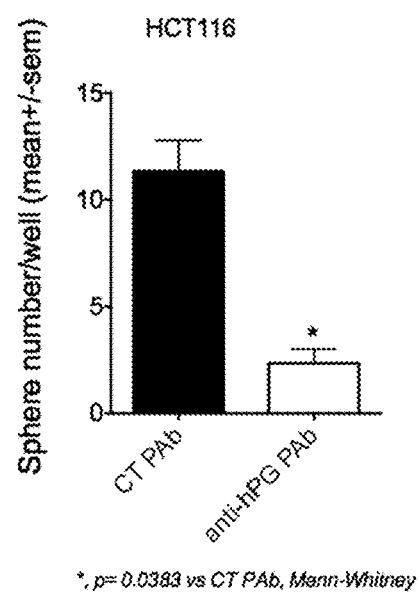

FIG. 16 provides a graph demonstrating the effect of anti-progastrin polyclonal antibodies on formation of spheroids by HCT116 primary colorectal cancer cells grown under low adherence culture conditions.

Figure 17:
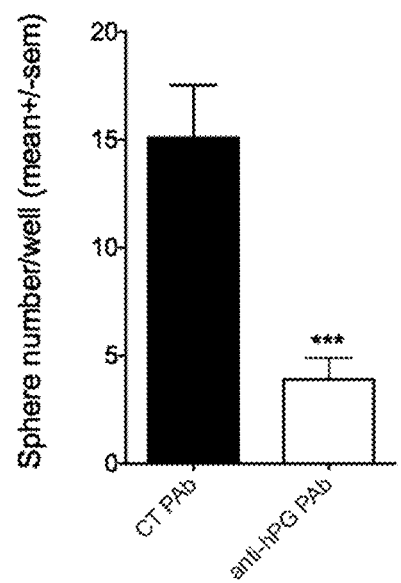

FIG. 17 provides a graph demonstrating the effect of anti-progastrin polyclonal antibodies on formation of spheroids by cells obtained from a biopsy sample of primary human colorectal cancer grown under low adherence culture conditions.

Figures 18A, 19A:
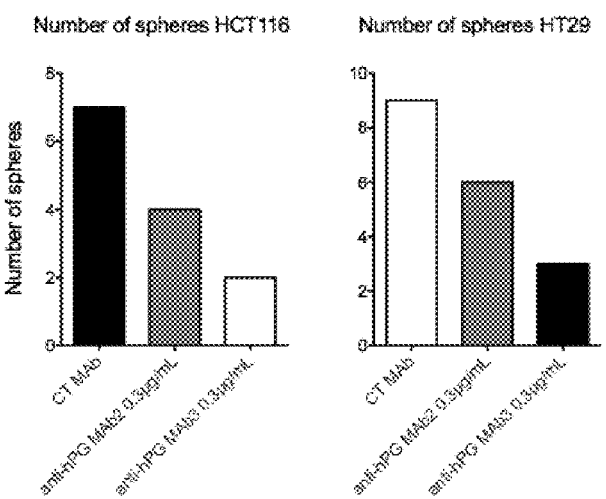

FIG. 18A provides a graph demonstrating the effect of two anti-progastrin monoclonal antibodies on formation of spheroids by LGR5-positive HT29 primary colorectal cancer cells incubated in low adherence culture conditions over 14 days.

Figures 18B, 19B:
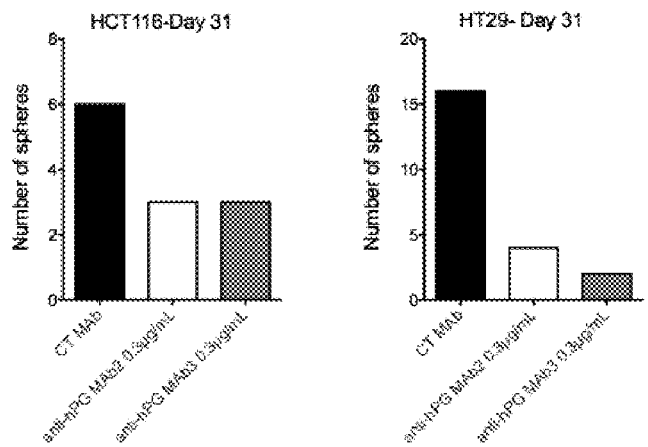

FIG. 18B provides a graph demonstrating that the inhibitory effect of treatment with anti-progastrin monoclonal antibodies on sphere formation by LGR5-positive HT29 primary colorectal cancer cells in low adherence culture continues for at least 17 days after the antibodies are removed.

FIG. 19A provides a graph demonstrating the effect of two anti-progastrin monoclonal antibodies on formation of spheroids by LGR5-positive HCT116 primary colorectal cancer cells incubated in low adherence culture conditions over 14 days.

FIG. 19B provides a graph demonstrating that the inhibitory effect of treatment with anti-progastrin monoclonal antibodies on sphere formation by LGR5-positive HCT116 primary colorectal cancer cells in low adherence culture continues for at least 17 days after the antibodies are removed.

Figure 20:
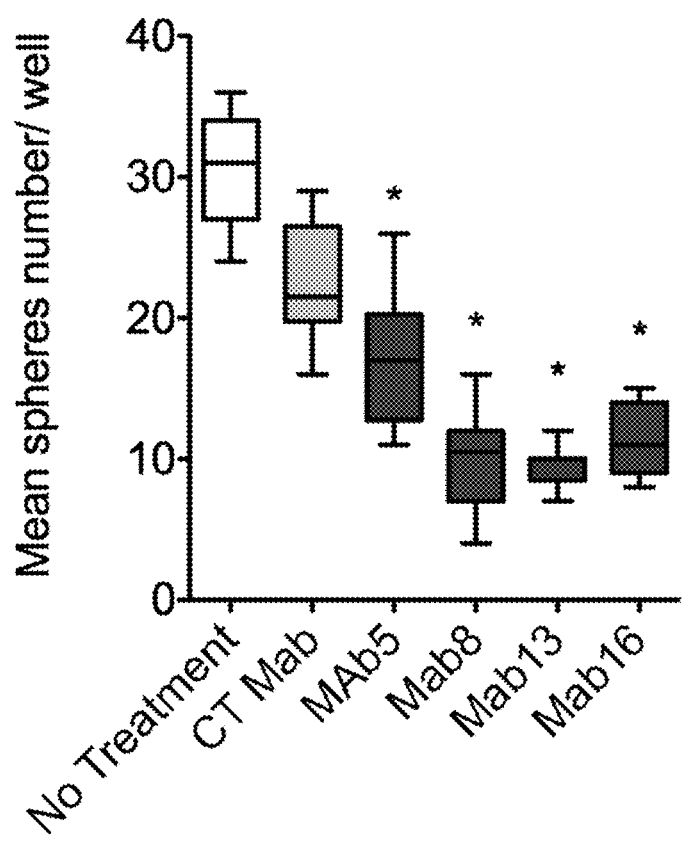

FIG. 20 provides a graph demonstrating the effect of treatment with four different anti-progastrin monoclonal antibodies on formation of spheroids by CRC1 primary colorectal cancer cells grown under low adherence culture conditions.

Figure 21:
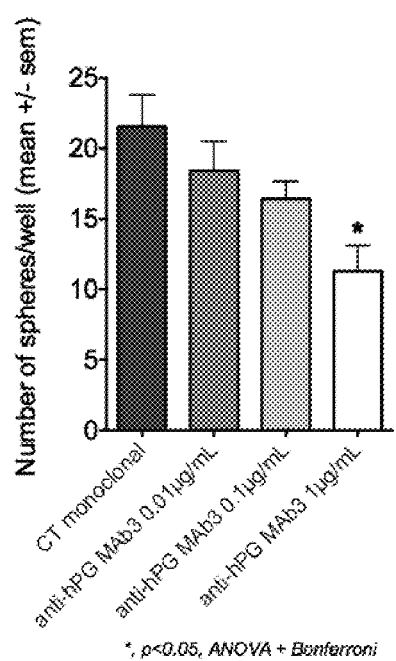

FIG. 21 provides a graph demonstrating the effect of anti-progastrin monoclonal antibodies on formation of spheroids by T84 metastatic colorectal cancer cells grown under low adherence culture conditions.

Figure 22:
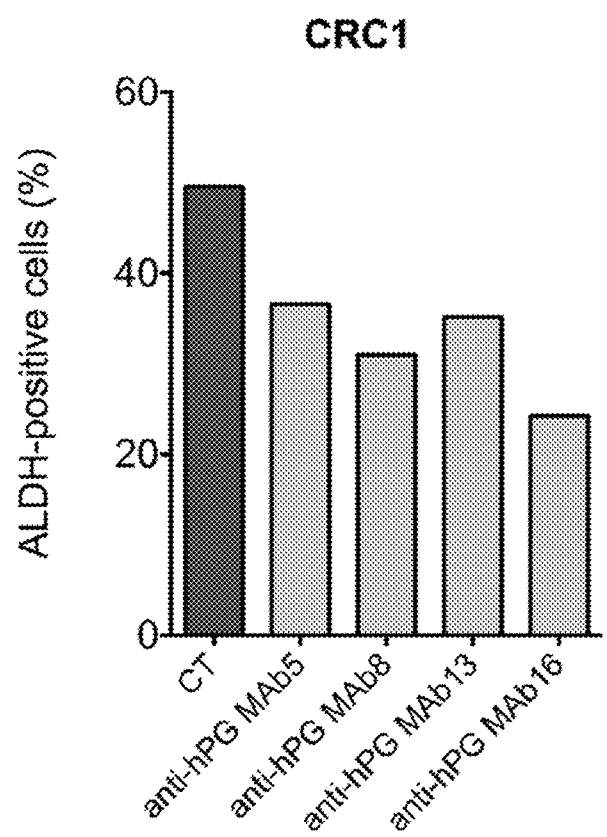

FIG. 22 provides a graph demonstrating the effect of treatment with four different anti-progastrin monoclonal antibodies on growth of ALDH1 positive primary colorectal cancer cells grown under conventional tissue culture conditions.

Figure 23:
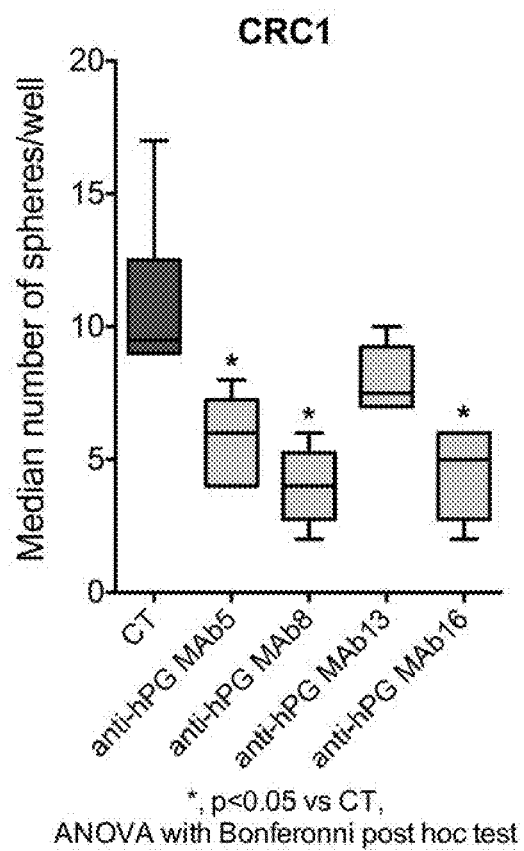

FIG. 23 provides a graph demonstrating the effect of pre-treatment with four different anti-progastrin monoclonal antibodies on growth of primary colorectal cancer cells as spheroids when grown under low adherence culture conditions.

Figure 24:
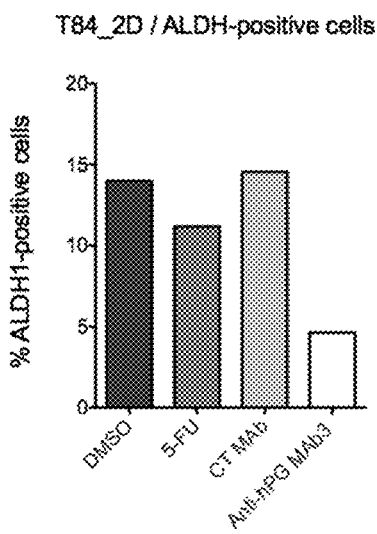

FIG. 24 provides a graph demonstrating the effect of pre-treatment with anti-progastrin monoclonal antibodies on expression of the cancer stem cell marker ALDH1 in T84 metastatic colorectal cancer cells.

Figure 25:
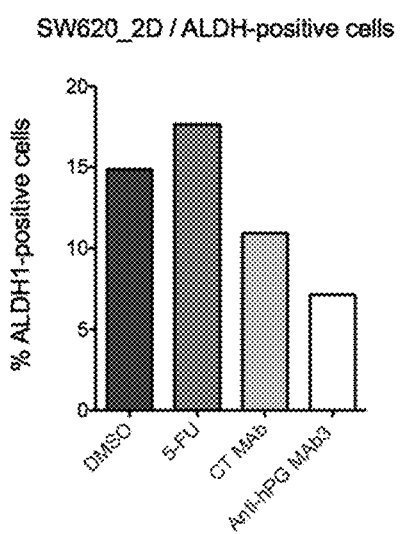

FIG. 25 provides a graph demonstrating the effect of pre-treatment with anti-progastrin monoclonal antibodies on expression of the cancer stem cell marker ALDH1 in SW620 metastatic colorectal cancer cells.

Figure 26:
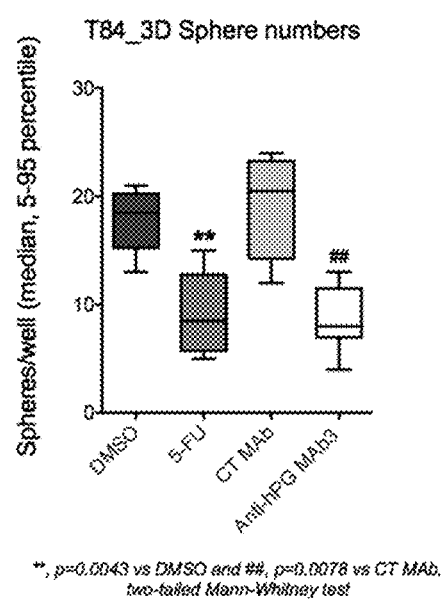

FIG. 26 provides a graph demonstrating the effect of pre-treatment with anti-progastrin monoclonal antibodies on formation of spheroids by T84 metastatic colorectal cancer cells grown under low adherence culture conditions.

Figure 27:
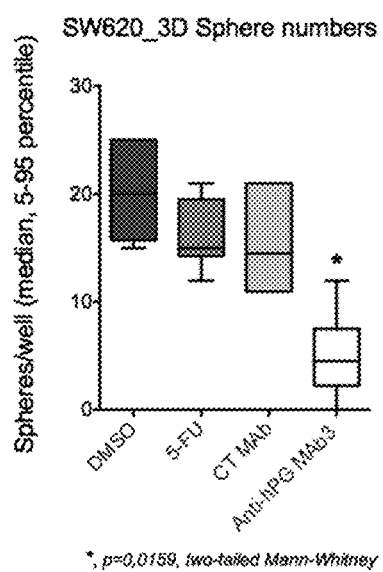

FIG. 27 provides a graph demonstrating the effect of pre-treatment with anti-progastrin monoclonal antibodies on formation of spheroids by SW620 metastatic colorectal cancer cells grown under low adherence culture conditions.

Figure 28:
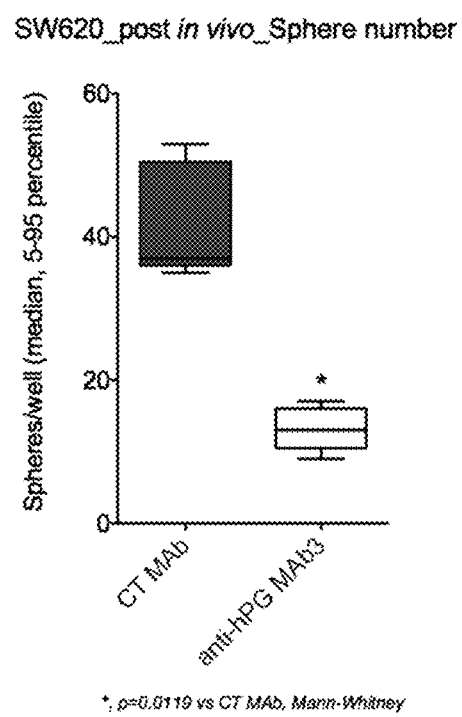

FIG. 28 provides a graph demonstrating the effect of treating mice bearing human metastatic colorectal cancer xenografts with anti-progastrin monoclonal antibodies on the ability of metastatic colorectal cancer cells isolated from the xenograft to grow as spheroids under low adherence culture conditions.

Figure 29:
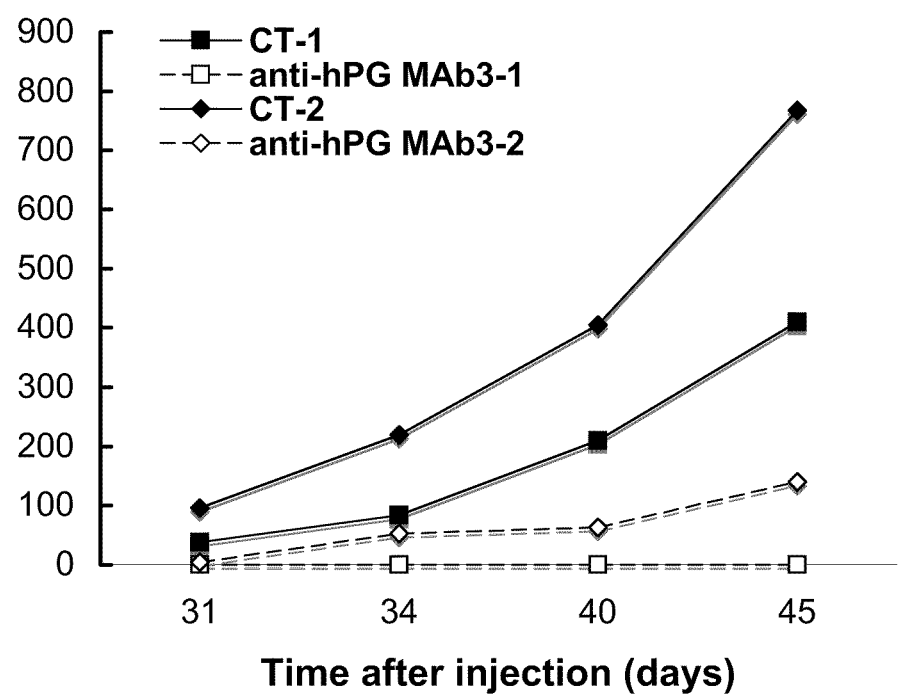

FIG. 29 provides a graph demonstrating the effect of treating mice bearing human metastatic colorectal cancer xenografts with anti-progastrin monoclonal antibodies on the ability of metastatic colorectal cancer cells isolated from the xenograft to initiate new tumor growth when transplanted into other mice.

FIG. 30 provides amino acid sequences of human preprogastrin (SEQ ID NO:100), where the signal peptide sequence is underlined, mature human progastrin (SEQ ID NO:101) and certain products of progastrin processing, including G34 (SEQ ID NO:102), G34-Gly (SEQ ID NO:103), G17 (SEQ ID NO:104), G17-Gly (SEQ ID NO:105) and CTFP (SEQ ID NO:106).

FIG. 31. provides polynucleotide and amino acid sequences of variable light and variable heavy chains of certain exemplary murine anti-hPG monoclonal antibodies. In each case, the three CDRs are shown in bolded-underlined text. Specifically:

FIG. 31A provides the polypeptide sequence of the $V_H$ chain of murine anti-hPG MAb3 (SEQ ID NO:12) and a polynucleotide sequence encoding it (SEQ ID NO:16);

FIG. 31B provides the polypeptide sequence of the $V_L$ chain of murine anti-hPG MAb3 (SEQ ID NO:13) and a polynucleotide sequence encoding it (SEQ ID NO:17);

FIG. 31C provides the polypeptide sequence of the $V_H$ chain of murine anti-hPG MAb4 (SEQ ID NO:14) and a polynucleotide sequence encoding it (SEQ ID NO:18);

FIG. 31D provides the polypeptide sequence of the $V_L$ chain of murine anti-hPG MAb4 (SEQ ID NO:15) and a polynucleotide sequence encoding it (SEQ ID NO:19);

FIG. 31E provides the polypeptide sequence of the $V_H$ chain of murine anti-hPG MAb8 (SEQ ID NO:59) and a polynucleotide sequence encoding it (SEQ ID NO:67);

FIG. 31F provides the polypeptide sequence of the $V_L$ chain of murine anti-hPG MAb8 (SEQ ID NO:63) and a polynucleotide sequence encoding it (SEQ ID NO:71);

FIG. 31G provides the polypeptide sequence of the $V_H$ chain of murine anti-hPG MAb13 (SEQ ID NO:60) and a polynucleotide sequence encoding it (SEQ ID NO:68);

FIG. 31H provides the polypeptide sequence of the $V_L$ chain of murine anti-hPG MAb13 (SEQ ID NO:64) and a polynucleotide sequence encoding it (SEQ ID NO:72);

FIG. 31I provides the polypeptide sequence of the $V_H$ chain of murine anti-hPG MAb16 (SEQ ID NO:61) and a polynucleotide sequence encoding it (SEQ ID NO:69);

FIG. 31J provides the polypeptide sequence of the $V_L$ chain of murine anti-hPG MAb16 (SEQ ID NO:65) and a polynucleotide sequence encoding it (SEQ ID NO:73);

FIG. 31K provides the polypeptide sequence of the $V_H$ chain of murine anti-hPG MAb19 (SEQ ID NO:62) and a polynucleotide sequence encoding it (SEQ ID NO:70); and FIG. 31L provides the polypeptide sequence of the $V_L$ chain of murine anti-hPG MAb19 (SEQ ID NO:66) and a polynucleotide sequence encoding it (SEQ ID NO:74).

FIG. 32 provides projected polypeptide sequences for humanized variable heavy and light chains of selected anti-hPG monoclonal antibodies described herein. In each case, the three CDRs are shown in bolded-underlined text. Specifically:

FIG. 32A provides the projected amino acid sequence of the $V_H$ chain of humanized MAb3 (SEQ ID NO:21);

FIG. 32B provides the projected amino acid sequence of the $V_L$ chain of humanized MAb3 (SEQ ID NO:22);

FIG. 32C provides the projected amino acid sequence of the $V_H$ chain of humanized MAb4 (SEQ ID NO:23);

FIG. 32D provides the projected amino acid sequence of the $V_L$ chain of humanized MAb4 (SEQ ID NO:24);

FIG. 32E provides the projected amino acid sequence of the $V_H$ chain of humanized MAb8(a) (SEQ ID NO:75);

FIG. 32F provides the projected amino acid sequence of the $V_L$ chain of humanized MAb8(a) (SEQ ID NO:76);

FIG. 32G provides the projected amino acid sequence of the $V_H$ chain of humanized MAb8(b) (SEQ ID NO:77);

FIG. 32H provides the projected amino acid sequence of the $V_L$ chain of humanized MAb8(b) (SEQ ID NO:78);

FIG. 32I provides the projected amino acid sequence of the $V_H$ chain of humanized MAb8(c) (SEQ ID NO:79);

FIG. 32J provides the projected amino acid sequence of the $V_L$ chain of humanized MAb8(c) (SEQ ID NO:76);

FIG. 32K provides the projected amino acid sequence of the $V_H$ chain of humanized MAb13(a) (SEQ ID NO:80);

FIG. 32L provides the projected amino acid sequence of the $V_L$ chain of humanized MAb13(a) (SEQ ID NO:81);

FIG. 32M provides the projected amino acid sequence of the $V_H$ chain of humanized MAb13(b) (SEQ ID NO:82);

FIG. 32N provides the projected amino acid sequence of the $V_L$ chain of humanized MAb13(b) (SEQ ID NO:83);

FIG. 32O provides the projected amino acid sequence of the $V_H$ chain of humanized MAb16(a) (SEQ ID NO:84);

FIG. 32P provides the projected amino acid sequence of the $V_L$ chain of humanized MAb16(a) (SEQ ID NO:85);

FIG. 32Q provides the projected amino acid sequence of the $V_H$ chain of humanized MAb16(b) (SEQ ID NO:86);

FIG. 32R provides the projected amino acid sequence of the $V_L$ chain of humanized MAb16(b) (SEQ ID NO:87);

FIG. 32S provides the projected amino acid sequence of the $V_H$ chain of humanized MAb16(c) (SEQ ID NO:88);

FIG. 32T provides the projected amino acid sequence of the $V_L$ chain of humanized MAb16(c) (SEQ ID NO:89);

FIG. 32U provides the projected amino acid sequence of the $V_H$ chain of humanized MAb19(a) (SEQ ID NO:90);

FIG. 32V provides the projected amino acid sequence of the $V_L$ chain of humanized MAb19(a) (SEQ ID NO:91);

FIG. 32W provides the projected amino acid sequence of the $V_H$ chain of humanized MAb19(b) (SEQ ID NO:92);

FIG. 32X provides the projected amino acid sequence of the $V_L$ chain of humanized MAb19(b) (SEQ ID NO:93);

FIG. 32Y provides the projected amino acid sequence of the $V_H$ chain of humanized MAb19(c) (SEQ ID NO:94); and FIG. 32Z provides the projected amino acid sequence of the $V_L$ chain of humanized MAb19(c) (SEQ ID NO:95).

7. DETAILED DESCRIPTION

7.1. Colorectal Cancer Metastasis

Metastasis refers to a process by which cancer spreads. Briefly, tumor cells leave a primary tumor, travel via the blood circulation or lymphatic system to a new tissue site, and form a secondary tumor. The tumors at the new tissue site are referred to as metastatic tumors, and typically identify the source of the primary tumor. For example, colorectal cancer that has spread to other tissues is referred to as "metastatic colorectal cancer," despite the tissue location of the secondary, metastatic tumor. The most common organs to which colorectal cancer metastasizes are the liver and lungs, but colorectal cancer may spread to other organs as well.

Cancer cells frequently spread to lymph nodes near the primary tumor, which is called lymph node involvement or regional disease.

Without wishing to be bound by any particular theory of operation, metastasis is believed to proceed through a number of distinct steps, including invasion and migration, intravasation, circulation, extravasation and colonization, proliferation and angiogenesis. During invasion and migration, individual cells detach themselves from the primary tumor and invade adjacent healthy tissue. To accomplish this, the cancer cells are hypothesized to undergo a phenotypic transformation called an epithelial to mesenchymal transition. Kalluri, R., et al., *J. Clin. Invest.*, 119(6) (2009), 1420-28. Such cells may produce enzymes capable of degrading the extracellular matrix, thereby facilitating migration out of the primary tumor and into surrounding healthy tissue. When a migrating cancer cell encounters a blood or lymphatic vessel it inserts itself between the endothelial cells lining the vessels and penetrates into the blood stream or lymphatic system. The aberrant cell then travels via the circulatory system or lymphatic system to a new organ. The cancer cell may then lodge in the capillaries or lymphatics of the new organ and then extravasate by penetrating the endothelium into the tissue space. Finally, during colonization, proliferation and angiogenesis, the metastatic cancer cell takes up residence in its new host tissue and begins to grow. When the new metastatic tumor reaches sufficient size, it may secrete growth factors, such as VEGF, to stimulate growth of new blood vessels into the tumor to supply oxygen and nutrition required by the fast growing tumor.

7.2. Colorectal Cancer Recurrence

Colorectal cancer recurrence is defined as a return of colorectal cancer after treatment which apparently caused the colorectal cancer to disappear. If the returning colorectal cancer is in the same place as the original cancer or is very close to it, it is known as local recurrence. Where the returning colorectal cancer grows in lymph nodes or tissues near the place of the original cancer, it is known as a regional recurrence, and where the returning colorectal cancer metastasized to organs or tissues far from the place of the original cancer, it is known as a distant recurrence.

7.3. Cancer Stem Cells and Colorectal Cancer

Solid tumors are not necessarily homogenous tissues. Rather, some tumors comprise a plurality of aberrant cell types having distinct phenotypic and functional properties. In this respect, such tumors are analogous to abnormal organs. One important difference among the cells comprising solid tumors is the extent to which they are capable of initiating formation of a new tumor when transplanted to a new site in the same host, or to a new host of the same or different species. Cells having this property are known as tumor or cancer initiating cells, or alternatively, tumor or cancer stem cells. In contrast, other cells comprising the tumor have much reduced potential to initiate new tumors after transplantation, even when many more cells are used. In one non-limiting example, several hundred colon cancer stem cells derived from human tumors were sufficient to initiate a new tumor after transplantation into mice, whereas 10,000 non-stem cells from the tumors were insufficient to do so. Dalerba, P., et al., 2007, "Phenotypic characterization of human colorectal cancer stem cells," *Proc. Natl. Acad. Sci. USA,* 104:10158-10163.

In many tumors, cancer stem cells comprise a relatively small proportion of all viable cells existing within a tumor. By contrast, the majority of tumor cells comprising the bulk of the tumor are unable to initiate a new tumor when transplanted. In some tumors, however, cancer stem cells may constitute the majority, or even all the cells comprising the tumor. As used herein, bulk tumor cells refer to tumor cells unable to initiate new tumors upon transplantation, unless large numbers of such cells are used. Cancer stem cells also have different phenotypic characteristics than bulk tumor cells including the ability to self-renew and form a new tumor upon transplantation of a relatively small number of cancer stem cells, and expression of different markers detectable by fluorescence activated cell sorting (FACS) or other assays. Other distinctions between cancer stem cells and bulk tumor cells are also possible.

Without wishing to be bound by any particular theory of operation, cancer stem cells are believed to share certain properties with normal stem cells which in the context of cancer stem cells contributes to their ability to give rise to tumors. In particular, cancer stem cells undergo asymmetric cell division to produce two types of daughter cells. The first remains undifferentiated and retains the stem cell characteristic of its parent of being able to renew itself indefinitely. The other daughter, called a progenitor cell, is capable of dividing and differentiating, albeit aberrantly, to give rise to the spectrum of more differentiated cells found in many solid tumors. Progenitor cells proliferate at a higher rate than stem cells and thus contribute to the physical growth of the tumor, whereas the stem cells are responsible for the ability of the tumor to grow indefinitely by generating new progenitors.

These properties allow cancer stem cells to give rise ultimately to the great number of cells comprising the growing tumor. Thus, when transplanted into a new animal, cancer stem cells can reconstitute the type of tumor from which they originated, even after multiple serial transplantations. Cancer stem cells however, unlike normal stem cells, harbor genetic mutations and/or epigenetic changes that can result in altered proliferation patterns and/or low rates of apoptosis, as well as result in aberrant differentiation causing the accumulation of the abnormal cells that may constitute the bulk of the tumor.

Cancer stem cells can be identified according to a number of phenotypic characteristics that distinguish them from bulk tumor cells. First, as noted above, cancer stem cells have the ability to initiate a new tumor when transplanted into a new host. By contrast, bulk tumor cells are either unable to initiate new tumors or require many more cells than cancer stem cells to achieve new tumor initiation. Cancer stem cells are also identifiable by their expression or non-expression of certain markers, whereas bulk tumor cells from the same tumor have different patterns of marker expression. Cancer stem cells also have a preferential ability, compared to bulk tumor cells, to grow under serum-free low-adherence culture conditions and form so-called spheroids. Other phenotypic differences capable of distinguishing cancer stem cells from bulk tumor cells are possible.

As noted above, cancer stem cells may also be identified according to patterns of expression of certain markers, either alone or in combination with others. Cancer stem cells from different tumors, however, may exhibit different marker phenotypes. Such markers include proteins expressed within the cell, or on the cell surface, and can be detected using a variety of techniques including, but not limited to, immunohistochemistry, immunofluorescence and FACS analysis. Other techniques for detecting marker are also possible according to the knowledge of those ordinarily skilled in the art. Markers also include proteins the activity of which can be assayed functionally in cancer stem cells. Non-limiting examples of types of markers include transporter proteins, such as those that export substances from cells or uptake substances into cells, enzymes, such as detoxifying enzymes.

Exemplary markers that may be used to identify colorectal cancer stem cells include, but are not limited to: CD133, CD44, CD166, EpCAM and LGR5. Other markers useful for identifying colorectal cancer stem cells are also possible. In some embodiments, the absence of expression of a marker is indicative of the cancer stem cell phenotype. In addition, Aldehyde dehydrogenase 1 (ALDH1) is a detoxifying enzyme and cancer cells can be assayed for increased ALDH1 activity, another marker for cancer stem cells.

In some embodiments of the present disclosure, colorectal cancer stem cells may be identified by the following marker phenotype, using FACS, or other techniques familiar to those of ordinary skill in the art: EpCAM(hi)CD44(+), EpCAM(hi) CD44(+)CD166(+), CD133(+), ALDH1(+), CD133(−)/ ALDH1(+), CD44(+)/CD24(+) or LGR5(+). Expression of other markers, and combinations and patterns thereof, may also be used to identify cancer stem cells in these cancers, as well as other types of cancers.

In other embodiments of the present disclosure, cancer stem cells may be identified using FACS analysis as those cells sorted into the so-called side population according to their preferential ability to exclude certain dyes. One non-limiting example of such a dye is Hoechst dye 33342.

As noted above, cancer stem cells can also be distinguished from bulk tumor cells by their increased capacity to initiate new tumor growth after transplantation into a new host. Thus, one way to confirm the identity of a population of cells suspected of being cancer stem cells is to test their ability to initiate tumor growth after transplantation into a non-human recipient animal of a relative small population of such cells compared to bulk tumor cells.

Methods of transplantation useful for assessing whether a tumor or cell line contains cancer stem cells are familiar to those of ordinary skill in the art. As a non-limiting example, a tumor, or portion thereof, suspected of containing cancer stem cells is isolated, such as by surgical resection. Thereafter the tumor tissue is minced and treated with enzymes, or some other treatment, effective to disaggregate the tumor and release its constituent cells. Alternatively, where a cell line is under analysis, it may only be necessary to disassociate the cells with enzymatic or chemical treatment.

After a cell suspension is prepared, the cells are collected by centrifugation and subpopulations known to correspond to cancer stem cells are isolated according to methods known in the art. As discussed above, in one non-limiting example, such cells express certain patterns of markers indicative of cancer stem cells, which are detectable using specific antibodies and fluorescence activated cell sorting (FACS). In other embodiments, subpopulations suspected of containing cancer stem cells can be isolated according to other phenotypic characteristics, such as their ability to exclude certain dyes.

After isolating the relevant cellular subpopulations, predetermined numbers of such cells are then implanted into one or more target tissues or organs in a recipient animal. In some embodiments, the recipient animal is an immunodeficient mouse, including but not limited to nude mice, mice with severe combined immunodeficiency (SCID), and nonobese-diabetic SCID (NOD-SCID) mice. Other species can also be used, according to the knowledge of the ordinarily skilled artisan.

Cells can be implanted subcutaneously, into fat pads (such as the mammary fat pad of mice), into the brain, caecum, pancreas or liver, or into the kidney (such as into the renal capsule). Cells can be implanted into other tissues and organs, as well. In some embodiments, the target tissue or organ is chosen to replicate the tissue or organ of origin of the tumor under analysis. However, in other embodiments, distinct tissues or organs are chosen in which to host the implanted cells. As a non-limiting example, colon cancer stem cells can be transplanted into the renal capsule of a NOD-SCID mouse to assess their ability to initiate a new tumor.

After implantation, which is effected using techniques familiar to those of ordinary skill, the cells are left undisturbed to determine whether a new tumor grows at the site of implantation. For cells implanted subcutaneously, tumor growth can be assessed by visual examination and palpation of the site of implantation. If a tumor does grow, its size can be measured through time using calipers. For cells implanted into an internal organ, the animal may be sacrificed at a predetermined time post-implantation to determine if a tumor is present, and if so, its size. Alternatively, according to the knowledge of the ordinary skilled artisan, non-invasive techniques can be used to assess tumor growth.

The cancer stem cell phenotype is also characterized by the preferential ability of cancer stem cells to grow as spheroids under serum-free, low adherence culture conditions, whereas bulk tumor cells are less likely to be able to grow as spheroids under the same conditions. Spheroids are compacted balls of cells that form as certain cells grow in culture after being seeded as disaggregated suspensions. The formation of such spheroids is promoted when the cells are grown in serum-free medium, generally in the presence of specific growth factors (including, but not limited to, Epidermal Growth Factor (EGF) and basic Fibroblast Growth Factor (bFGF)), and in tissue culture dishes having surfaces to which mammalian cells poorly adhere. Similar to stem cells from normal tissues, it has been discovered that cancer stem cells preferentially grow as spheroids under the appropriate culture conditions. See, e.g., Rappa, G., et al., *Exp. Cell Res.*, 314:2110 (2008); Singh, S. K., et al., *Cancer Res.*, 63:5821 (2003); Fang, D., et al., *Cancer Res.*, 65:9328 (2005). By contrast, bulk tumor cells, which tend to more highly differentiated, are less likely to form spheroids under the same culture conditions. Where bulk tumor cells are able to form spheroids, they tend to be smaller and/or fewer in number compared to those formed by a similar number of cancer stem cells.

7.4. Cancer Stem Cells and Colorectal Cancer Recurrence

Tumor cells with properties of cancer stem cells have been identified that exhibit enhanced resistance to radiation and/or chemotherapeutic agents. Different molecular mechanisms have been proposed to explain resistance of cancer stem cells to radiation or chemotherapeutic agents. For example, it has been reported that certain cancer stem cells may be able to more readily repair their DNA after genotoxic insults, whereas other cancer stem cells express high levels of anti-apoptotic proteins or of molecular pumps effective to eliminate chemotherapeutic agents entering such cells. Eyler, C. E., and J. N. Rich, *J. Clin. Oncol.*, 26:2839-2845 (2008). That cancer stem cells also proliferate more slowly than progenitor cells may also explain the comparative ability of stem cells to survive exposure to radiation and toxic chemotherapeutic agents that would kill bulk tumor cells.

Without wishing to be bound by any particular theory of operation, the observation that cancer stem cells are resistant to radiation and chemotherapy may explain the phenomenon of recurrence in cancer patients treated with such therapies. Eyler, supra. In such patients, treatment is initially effective, causing the tumors to apparently disappear in diagnostic scans but the tumors reappear some time after treatment ceases.

With respect to the role of cancer stem cells in the mechanism of recurrence, it is hypothesized that while most or even all the bulk tumor cells are killed by the therapy, there remain a number of viable cancer stem cells that survive due to their enhanced ability to resist the effects of radiation or chemotherapy. After therapy is concluded, these surviving cells continue to grow, permitting reformation of the original tumor or formation of new tumors. Consistent with this theory, it was reported that treatment of mice with a chemotherapeutic agent caused tumors initiated from human colorectal cancer cells to shrink, but increased the proportion of cancer stem cells within the tumors. Dylla, S. J., et al., 2008, "Colorectal Cancer Stem Cells Are Enriched in Xenogeneic Tumors Following Chemotherapy," *PLoS ONE*, 3 (6):e2428.

7.5. Advances in Understanding the Role of Progastrin in Colorectal Cancer

It has surprisingly been discovered that there exist progastrin sensitive metastatic colorectal cancer cells and colorectal cancer stem cells as demonstrated by the ability of certain antibodies that specifically bind to progastrin ("PG") to inhibit the growth of such cells in vitro or in vivo.

A PG-sensitive colorectal cancer cell is one that at least partly depends on progastrin for its survival and/or growth, directly or indirectly. Without wishing to be bound by any particular theory of operation, it is hypothesized that certain anti-PG antibodies are effective to inhibit the survival and/or growth of such cells by binding to PG and blocking PG-dependent signaling. Progastrin is therefore prevented from mediating its survival and/or growth-promoting effects. Other mechanisms by which anti-PG antibodies inhibit the survival and/or growth of colorectal cancer cells may exist, and the particular mechanism of action is not intended to limit the scope of the present disclosure.

As described in further detail in the examples, applicants have surprisingly discovered that the gastrin gene (GAST) is expressed in six different human primary colorectal cancer cell lines, HT29, HCT116, RKO, SW480, DLD1 and CRC1 cells, and in two different human metastatic colorectal cancer cell lines, SW620 and T84 cells. Related to the data from the in vitro experiments, applicants have also surprisingly discovered that the gastrin gene was expressed in the primary colorectal tumor and matched colorectal metastases obtained from each of 11 different patients, although relative to the levels in the primary tumors the level of expression in the matched metastases varied among the different patients. Because progastrin is a product of the gastrin gene (along with other peptides processed post-translationally from the same gene product), this data suggests that primary and metastatic colorectal tumors secrete progastrin. Additional experiments, as explained below, confirmed this.

First, applicants confirmed that detectable amounts of PG protein were secreted into the growth medium by SW620 and T84 cells (although not by Colo-205 cells). Additionally, applicants demonstrated that patients having primary colorectal cancer only, primary and metastatic colorectal cancer concurrently, and metastatic colorectal cancer after resection of the primary tumor, all had levels of PG in their blood that were statistically significantly higher than in the blood of healthy controls. These results indicate that primary and metastatic colorectal tumors secrete PG, which directly or indirectly enters the blood stream. Thus, elevated blood PG levels are indicative of the presence of primary as well as metastatic colorectal cancer. Accordingly, the methods of the present disclosure provide methods of detecting or diagnosing the presence of both primary and metastatic colorectal cancer in different patient populations.

The applicants have also surprisingly discovered that certain anti-PG antibodies, i.e., neutralizing antibodies, are capable of inhibiting the growth of metastatic colorectal cancer cells in culture. Specifically, applicants demonstrated experimentally that anti-PG polyclonal antibodies and four different anti-PG monoclonal antibodies were able to inhibit the growth of SW620 cells growing in culture. Similarly, the growth of T84 cells was inhibited by incubation with an anti-PG monoclonal antibody. These data demonstrate that neutralizing anti-PG antibodies are capable of preventing the growth of metastatic colorectal cancer cells, and that such cells are therefore PG sensitive. These data further indicate that therapeutically effective amounts of such antibodies, when administered to a subject in need of treatment of metastatic colorectal cancer, will be effective to treat such metastases.

Further experiments conducted in nude mice extend and confirm applicants' in vitro experiments. Thus, applicants injected metastatic SW620 cells into the spleens of nude mice. Shortly thereafter, the spleens were resected, and the mice were administered an anti-PG monoclonal antibody over a time course. Control animals were processed similarly, but injected with a control antibody. After six weeks of treatment, the mice were sacrificed, and the number and weight of the metastases that formed in the liver were counted. Surprisingly, applicants found that the mean number of metastases dropped by a statistically significant 41% in the treated animals versus the control animals. This compelling data confirms that neutralizing anti-PG antibodies are capable of inhibiting the growth of metastatic colorectal cancer in vivo, and demonstrates that therapeutically effective amounts of such antibodies, when administered to a subject in need of treatment for metastatic colorectal cancer, are effective to treat such metastases.

Additional experiments carried out in vitro and in vivo by applicants have surprisingly demonstrated that primary and metastatic colorectal cancers contain colorectal cancer stem cells that are PG sensitive and that neutralizing anti-hPG antibodies are capable of inhibiting the growth of such cells.

In one experiment, applicants demonstrated that growth of primary (HT29, HCT116, CRC1) and metastatic (SW620 and T84) colorectal cancer cell lines under low adherence culture conditions increased the proportion of cells expressing LGR5, a phenotypic marker of colorectal cancer stem cells. Such culture conditions preferentially select for the growth of cancer stem cells compared to the non-stem cell subpopulation, and the increased expression of LGR5 confirms that both primary and metastatic colorectal cancers contain cancer stem cells.

Applicants then discovered that low adherence conditions increased the level of gastrin gene expression in the same cells compared to growth of the cells under conventional conditions. This data suggests that gastrin gene expression is higher in colorectal cancer stem cells from both primary and metastatic colorectal cancers compared to the non-stem cells in the same populations, and further suggests that the level of secreted progastrin would be higher as well. Applicants confirmed progastrin expression in CRC1, HT29, SW620 and T84 cells at different levels when grown under low adherence conditions, suggesting that these cell lines contain PG sensitive colorectal cancer stem cells.

Applicants confirmed this by treating primary and metastatic colorectal cancer cells grown under low adherence conditions with anti-hPG antibodies and surprisingly found that the number of so-called cell spheroids formed was reduced compared to treatment with a control antibody. Because formation of spheroids under low adherence conditions is a property of colorectal cancer stem cells, but not the non-stem cell subpopulation, this result is interpreted to mean that anti-hPG antibodies are effective to inhibit the growth of colorectal cancer stem cells in both primary and metastatic colorectal cancers.

For example, treatment of HT29, HCT116 and CRC1 cells, all of which are primary colorectal cancer cells, with anti-hPG polyclonal antibodies resulted in reduced sphere formation. Further testing of the HCT116 and HT29 cells found a similar effect on sphere growth by the subpopulation of LGR5 positive cancer stem cells using two different anti-hPG monoclonal antibodies. Interestingly, removal of the antibodies by washing, followed by continued incubation for 17 days in the absence of added antibodies did not result in increased sphere numbers, suggesting that the inhibitory effect of the anti-hPG antibodies on colorectal cancer stem cells was permanent and not dependent on their continued presence. Treatment of CRC1 cells with four different anti-hPG monoclonal antibodies was also effective to reduce sphere formation. Additionally, pretreatment of CRC1 cells growing under conventional conditions with the same set of anti-hPG monoclonal antibody reduced the number of ALDH1 positive cells as well as the number of spheroids formed after the pretreated cells were transferred to low adherence culture conditions. Three of the antibodies recognized the C-terminal portion PG, whereas one recognized the N-terminal portion.

Similar results were obtained when metastatic colorectal cancer cell lines were tested. Thus, after isolation of the subpopulation of T84 cells positive for ALDH1, another marker for colorectal cancer stem cells, the number of spheroids formed by such cells was reduced in a dose responsive manner by treatment with an anti-hPG monoclonal antibody compared to control antibody. Similarly, pretreatment of T84 and SW620 cells growing under conventional conditions with the same anti-hPG monoclonal antibody reduced the number of ALDH1 positive cells as well as the number of spheroids formed after the pretreated cells were transferred to low adherence culture conditions. In fact, the growth inhibitory effect was greater than that of 5-fluorouracil, a chemotherapeutic drug. This data confirms the surprising conclusion that metastatic colorectal cancer cells contain progastrin sensitive stem cells, the growth of which can be inhibited by treatment with a specific anti-hPG monoclonal antibody.

As discussed earlier, one of the characteristic properties of cancer stem cells is their ability to initiate a new tumor after transplantation. To confirm the ability of anti-hPG antibodies to inhibit colorectal cancer stem cells, applicants tested the effect of a specific anti-hPG monoclonal antibody on the ability of cells from colorectal cancer liver metastases to grow as spheroids in culture and to initiate new tumors after transplantation. As explained further in the examples, applicants injected metastatic SW620 cells into the spleens of nude mice. Shortly thereafter, the spleens were resected, and the mice were administered an anti-PG monoclonal antibody over a time course. Control animals were processed similarly, but injected with a control antibody.

After six weeks of treatment, the mice were sacrificed and colorectal metastases forming in the liver were dissected and then treated to release viable metastatic colorectal cancer cells. The cells were then tested for their ability to form spheroids in low adherence culture and to form new tumors after transplantation into new mice. Both of these properties are characteristics of colorectal cancer stem cells.

The results confirmed the inhibitory effect of anti-hPG antibodies on the growth of colorectal cancer stem cells. First, the applicants found that fewer spheroids formed in low adherence culture from metastatic colorectal cancer cells isolated from the livers of the animals treated with the specific antibodies compared to controls. Further, applicants also found that when cells from the spheroids were injected subcutaneously into the thighs of two new test animals, the size of the tumors growing from the cells treated in vivo with the specific antibody were on average considerably smaller than those growing from the cells treated in vivo with control antibody. These compelling results demonstrate that treatment of metastatic colorectal cancer cells in vivo with an antibody specific for hPG reduces the number of colorectal cancer stem cells in the metastatic tumors.

Based upon the surprising and compelling results described above, treating patients with anti-hPG antibodies is expected to be effective to prevent recurrence of primary or metastatic colorectal cancer. Furthermore, the inhibitory effect of the antibodies on growth of such stem cells may not require the continued presence of anti-hPG antibodies.

7.6. Antibodies

Antibodies useful in the methods and kits disclosed herein are those that specifically bind human progastrin over other products of the gastrin gene. As illustrated in FIG. 30, the gastrin gene is translated into a 101-amino acid polypeptide, called pre-progastrin, which contains a signal sequence (underlined) that is cleaved, giving rise to progastrin, an 80-amino-acid polypeptide. Progastrin, in turn, is cleaved to generate a 34-amino-acid product, corresponding in sequence to residues 38-71 of progastrin, which is then extended at its carboxy terminus with a glycine residue, generating glycine-extended G34 ("G34-Gly"). A by-product of this cleavage is a 6-amino-acid peptide, called the C-terminal flanking peptide, or CTFP, which corresponds in sequence to residues 75-80 of progastrin. G34-Gly is then further cleaved to generate a 17-residue polypeptide corresponding in sequence to residues 55-71 of progastrin and referred to as G17-Gly. Removal of the C-terminal glycines of G34-Gly and G17-Gly, followed by C-terminal amidation, yields G34 and G17, respectively, both of which are C-terminal amidated.

As used herein, an antibody is "highly specific for" hPG or "highly specifically binds" hPG if it binds to full-length progastrin but does not bind at all to CTFP, to amidated gastrin, or to glycine-extended gastrin, and is "specific for" hPG or "specifically binds" hPG if it exhibits at least about 5-fold greater binding of hPG than CTFP and the other products of the gastrin gene, as measured in standard binding assays. A specific ELISA assay that can be used to assess the specificity of a particular anti-hPG antibody is provided in Example 21.

Such highly specific and/or specific anti-hPG antibodies (referred to herein as "anti-hPG antibodies") may be polyclonal ("anti-hPG PAbs") or monoclonal ("anti-hPG MAbs"), although for therapeutic uses and, in some instances, diagnostic or other in vitro uses, monoclonal antibodies are preferred.

The epitope bound by the anti-hPG antibodies is not critical. Useful anti-hPG antibodies may bind an N-terminal region of hPG, a C-terminal region of hPG, or a different region of hPG. Recently, it has been discovered that, at least for monoclonal anti-hPG antibodies, the selection of antigen used to raise the anti-hPG antibodies may be important (see, International Application No. PCT/EP2010/006329 filed Oct. 15, 2010 and U.S. application Ser. No. 12/906,041 filed Oct. 15, 2010, the disclosures and specifically disclosed anti-hPG antibodies of which are incorporated herein by reference; hereinafter referred to as the '329 and '041 applications, respectively). As disclosed in the '329 and '041 applications, not all antigens derived from hPG stimulate production of monoclonal antibodies that specifically bind hPG under physiological conditions. Indeed, certain antigens that have been used to successfully raise polyclonal anti-hPG antibodies, such as full-length recombinant hPG (see, e.g., WO 08/076454 to Singh) and a peptide corresponding to the last ten amino acids at the C-terminal end of hPG (see WO 07/135542 to Hollande et al.) failed to generate monoclonal antibodies. As noted in the '329 and '041 applications, antigenic N-terminal and C-terminal sequences within the hPG sequence have been identified that can be used to generate monoclonal antibodies that specifically bind hPG. Interestingly, the antigenic sequence need not be limited to regions of the hPG sequence that are unique to it. Peptide antigens having regions of sequence in common with other products of the gastrin gene, for example, G17, G34 and CTFP, yield monoclonal antibodies that not only bind hPG, but bind it specifically.

Anti-hPG antibodies obtainable using a peptide antigen having a sequence corresponding to an N-terminal region of hPG and/or that bind an N-terminal region of hPG are referred to herein as "N-terminal anti-PG antibodies." A specific exemplary antigenic region of hPG that can be used to construct an immunogen suitable for obtaining both polyclonal and monoclonal antibodies specific for hPG corresponds to residue 1 to 14 of hPG: SWKPRSQQPDAPLG (SEQ ID NO:25). Exemplary immunogens useful for obtaining N-terminal anti-hPG antibodies, as well as CDR and $V_H$ and $V_L$ sequences of N-terminal anti-hPG monoclonal antibodies obtained with these exemplary immunogens, are provided in TABLE 1A, below, and the Example sections:

TABLE 1A

N-Terminal Anti-hPG Monoclonal Antibodies

| Immunogen | Hybridoma (Deposit #) | MAb | Murine CDR Sequences | | | Murine $V_H$ and $V_L$ Sequences | Humanized $V_H$ and $V_L$ Sequences (projected) |
|---|---|---|---|---|---|---|---|
| N1 | 43B9G11 | MAb1 | | | | | |
| N1 | WE5H2G7 | MAb2 | | | | | |
| N2 | 6B5B11C10 | MAb3 | $V_H$ CDR 1.3 | GYIFTSYW | (SEQ ID NO: 1) | m$V_H$.3 (SEQ ID NO: 12) | h$V_H$.3 (SEQ ID NO: 21) |
| | | | $V_H$ CDR 2.3 | FYPGNSDS | (SEQ ID NO: 2) | | |
| | | | $V_H$ CDR 3.3 | TRRDSPQY | (SEQ ID NO: 3) | | |
| | | | $V_L$ CDR 1.3 | QSIVHSNGNTY | (SEQ ID NO: 4) | m$V_L$.3 (SEQ ID NO: 13) | h$V_L$.3 (SEQ ID NO: 22) |
| | | | $V_L$ CDR 2.3 | KVS | (SEQ ID NO: 5) | | |
| | | | $V_L$ CDR 3.3 | FQGSHVPFT | (SEQ ID NO: 6) | | |
| N2 | 20D2C3G2 | MAb4 | $V_H$ CDR 1.4 | GYTFSSSW | (SEQ ID NO: 7) | m$V_H$.4 (SEQ ID NO: 14) | m$V_H$.4 (SEQ ID NO: 23) |
| | | | $V_H$ CDR 2.4 | FLPGSGST | (SEQ ID NO: 8) | | |
| | | | $V_H$ CDR 3.4 | ATDGNYDWFAY | (SEQ ID NO: 9) | | |
| | | | $V_L$ CDR 1.4 | QSLVHSSGVTY | (SEQ ID NO: 10) | m$V_L$.4 (SEQ ID NO: 15) | m$V_L$.4 (SEQ ID NO: 24) |
| | | | $V_L$ CDR 2.4 | KVS | (SEQ ID NO: 5) | | |
| | | | $V_L$ CDR 3.4 | SQSTHVPPT | (SEQ ID NO: 11) | | |
| N2 | 1E9A4A4 (I-4376) | MAb15 | | | | | |
| N2 | 1E9D9B6 | MAb16 | $V_H$ CDR 1.16 | GYTFTSYY | (SEQ ID NO: 39) | m$V_H$.16 (SEQ ID NO: 61) | h$V_H$.16a (SEQ ID NO: 84) |
| | | | $V_H$ CDR 2.16 | INPSNGGT | (SEQ ID NO: 43) | | h$V_H$.16b (SEQ ID NO: 86) |
| | | | $V_H$ CDR 3.16 | TRGGYYPFDY | (SEQ ID NO: 47) | | h$V_H$.16c (SEQ ID NO: 88) |
| | | | $V_L$ CDR 1.16 | QSLLDSDGKTY | (SEQ ID NO: 50) | m$V_L$.16 (SEQ ID NO: 65) | h$V_L$.16a (SEQ ID NO: 85) |
| | | | $V_L$ CDR 2.16 | LVS | (SEQ ID NO: 53) | | h$V_L$.16b (SEQ ID NO: 87) |
| | | | $V_L$ CDR 3.16 | WQGTHSPYT | (SEQ ID NO: 57) | | h$V_L$.16c (SEQ ID NO: 89) |
| N2 | 1C8D10F5 | MAb17 | | | | | |
| N2 | 1A7C3F11 | MAb18 | | | | | |

TABLE 1A-continued

N-Terminal Anti-hPG Monoclonal Antibodies

| Immuno-gen | Hybridoma (Deposit #) | MAb | Murine CDR Sequences | | | Murine $V_H$ and $V_L$ Sequences | Humanized $V_H$ and $V_L$ Sequences (projected) |
|---|---|---|---|---|---|---|---|
| N2 | 1B3B4F11 | MAb19 | $V_H$ CDR 1.19 | GYSITSDYA | (SEQ ID NO: 40) | $mV_H$.19 (SEQ ID NO: 62) | $hV_H$.19a(SEQ ID NO: 90) |
| | | | $V_H$ CDR 2.19 | ISFSGYT | (SEQ ID NO: 44) | | $hV_H$.19b(SEQ ID NO: 92) |
| | | | $V_H$ CDR 3.19 | AREVNYGSDYHFDY | (SEQ ID NO: 48) | | $hV_H$.19c(SEQ ID NO: 94) |
| | | | $V_L$ CDR 1.19 | SAHRTYT | (SEQ ID NO: 51) | $mV_L$.19 (SEQ ID NO: 66) | $hV_L$.19a(SEQ ID NO: 91) |
| | | | $V_L$ CDR 2.19 | VKKDGSH | (SEQ ID NO: 54) | | $hV_L$.19b(SEQ ID NO: 93) |
| | | | $V_L$ CDR 3.19 | GVGDAIKGQSVFV | (SEQ ID NO: 58) | | $hV_L$.19c(SEQ ID NO: 95) |
| N2 | 1C11F5E8 | MAb20 | | | | | |

Immunogen N1 = SWKPRSQQPDAPLG-Ahx-Cys-BSA, also represented as (SEQ ID NO: 25)-Ahx-Cys-BSA
Immunogen N2 = SWKPRSQQPDAPLG-Ahx-Cys-KLH, also represented as (SEQ ID NO: 25)-Ahx-Cys-KLH
In TABLE 1A, all amino acid sequences are represented using conventional N→C orientation. For each immunogen, the progastrin peptide was synthesized with a C-terminal linker of one aminohexanoic acid (Ahx) residue followed by a cysteine (Cys) residue, which
was then conjugated to a either a bovine serum albumin ("BSA") or keyhole limpet hemocyanin ("KLH") carrier via the Cys linker residue.

Anti-hPG antibodies obtainable using a peptide antigen having a sequence corresponding to a C-terminal region of hPG, and/or that bind a C-terminal region of hPG, are referred to herein as "C-terminal anti-hPG antibodies." A specific exemplary antigenic region that can be used to construct an immunogen useful for obtaining both polyclonal and monoclonal C-terminal anti-hPG antibodies corresponds to residues 55 to 80 of hPG: QGPWLEEEEEAYGWMDFGRRSAEDEN (SEQ ID NO:27). Exemplary immunogens including this antigen useful for obtaining C-terminal anti-hPG antibodies, as well as CDR and $V_H$ and $V_L$ sequences of C-terminal anti-hPG monoclonal antibodies obtained with these exemplary immunogens, are provided in TABLE 1B, below, and the Examples section.

TABLE 1B

C-Terminal Anti-hPG Monoclonal Antibodies

| Immuno-gen | Hybridoma (Deposit #) | MAb | Murine CDR Sequences | | | Murine $V_H$ and $V_L$ Sequences | Humanized $V_H$ and $V_L$ Sequences (projected) |
|---|---|---|---|---|---|---|---|
| C1 | 1B4A11D11 (I-4371) | MAb5 | | | | | |
| C1 | 1B6A11F2 (I-4372) | MAb 6 | | | | | |
| C1 | 1B11E4B11 (I-4373) | MAb7 | | | | | |
| C1 | 1C10D3B9 | MAb8 | $V_H$ CDR 1.8 | GFTFTTYA | (SEQ ID NO: 37) | $mV_H$.8 (SEQ ID NO: 59) | $hV_H$.8a (SEQ ID NO: 75) |
| | | | $V_H$ CDR 2.8 | ISSGGTYT | (SEQ ID NO: 41) | | $hV_H$.8b (SEQ ID NO: 77) |
| | | | $V_H$ CDR 3.8 | ATQGNYSLDF | (SEQ ID NO: 45) | | $hV_H$.8c (SEQ ID NO: 79) |
| | | | $V_L$ CDR 1.8 | KSLRHTKGITF | (SEQ ID NO: 49) | $mV_L$.8 (SEQ ID NO: 63) | $hV_L$.8a (SEQ ID NO: 76) |
| | | | $V_L$ CDR 2.8 | QMS | (SEQ ID NO: 52) | | $hV_L$.8b (SEQ ID NO: 78) |
| | | | $V_L$ CDR 3.8 | AQNLELPLT | (SEQ ID NO: 55) | | $hV_L$.8c (SEQ ID NO: 76) |
| C1 | 1D8F5B3 | MAb9 | | | | | |
| C1 | 1E1C7B4 | MAb10 | | | | | |
| C1 | 2B4C8C8 (I-4374) | MAb11 | | | | | |
| C1 | 2B11E6G4 (I-4375) | MAb12 | | | | | |
| C1 | 2C6C3C7 | MAb13 | $V_H$ CDR 1.13 | GFIFSSYG | (SEQ ID NO: 38) | $mV_H$.13 (SEQ ID NO: 60) | $hV_H$.13a(SEQ ID NO: 80) |
| | | | $V_H$ CDR 2.13 | INTFGDRT | (SEQ ID NO: 42) | | $hV_H$.13b(SEQ ID NO: 82) |
| | | | $V_H$ CDR 3.13 | ARGTGTY | (SEQ ID NO: 46) | | |
| | | | $V_L$ CDR 1.13 | QSLLDSDGKTY | (SEQ ID NO: 50) | $mV_L$.13 (SEQ ID NO: 64) | $hV_L$.13a(SEQ ID NO: 81) |
| | | | $V_L$ CDR 2.13 | LVS | (SEQ ID NO: 53) | | $hV_L$.13b(SEQ ID NO: 83) |
| | | | $V_L$ CDR 3.13 | WQGTHFPQT | (SEQ ID NO: 56) | | |

TABLE 1B-continued

C-Terminal Anti-hPG Monoclonal Antibodies

| Immuno-gen | Hybridoma (Deposit #) | MAb | Murine CDR Sequences | Murine $V_H$ and $V_L$ Sequences | Humanized $V_H$ and $V_L$ Sequences (projected) |
|---|---|---|---|---|---|
| C1 | 2H9F4B7 | MAb14 | | | |
| C2 | 1F11F5E10 | MAb21 | | | |
| C2 | 1F11F5G9 | MAb22 | | | |
| C2 | 1A11F2C9 | MAb23 | | | |

Immunogen C1 = KLH-Cys-Ahx-Ahx-QGPWLEEEEEAYGWMDFGRRSAEDEN, also represented as KLH-Cys-Ahx-Ahx-(SEQ ID NO: 27)
Immunogen C2 = DT-Cys-Ahx-Ahx-QGPWLEEEEEAYGWMDFGRRSAEDEN, also represented as DT-Cys-Ahx-Ahx-(SEQ ID NO: 27)
In TABLE 1B, all amino acid sequences are represented using conventional N→C orientation. For each immunogen, the progastrin peptide was synthesized with an N-terminal Ahx-Ahx-Cys linker, which was then conjugated to a either a keyhole limpet hemocyanin ("KLH") or a diphtheria toxin ("DT") carrier via the Cys linker residue.

The specific epitopes bound by the exemplary anti-hPG monoclonal antibodies MAb1-MAb23 provided in TABLES 1A and 1B were mapped using the SPOT technique and alanine scanning, as described in Laune et al., 2002, J. Immunol. Methods 267:53-70 and Laune, 1997, J. Biol. Chem. 272:30937-30944, respectively (see also, Example 6 of the '329 application).

In the SPOT technique, 15 amino acid peptide sequences spanning a putative epitope are generated and spotted onto a nitrocellulose membrane which is then probed with the test antibody to determine the minimal epitope sequence recognized by the antibody. Alanine scanning is used to determine residues within an epitope that are critical for antibody binding. Each residue within a putative epitope is mutated, one by one, to an alanine, and the alanine-containing peptides are then probed with the test antibody.

For N-terminal anti-hPG monoclonal antibodies MAbs1-4 and 15-20, epitopes comprise at least the following sequences: DAPLG (SEQ ID NO:28), PDAPLG (SEQ ID NO:29), PRSQQPD (SEQ ID NO:30), WKPRSQQPD (SEQ ID NO:31), or WKPRSQQPDAPLG (SEQ ID NO:32), as shown in TABLE 2A below.

TABLE 2A

| MAb# | PG peptide antigen: SWKPRSQQPDAPLG | SEQ ID NO |
|---|---|---|
| MAb2 | WKPRSQQPDAPLG | 32 |
| MAb4 | WKPRSQQPDAPLG | 32 |
| MAb1 | PDAPLG | 29 |
| MAb3 | DAPLG | 28 |
| MAb17 | WKPRSQQPD | 31 |
| MAb18 | WKPRSQQPD | 31 |
| MAb19 | WKPRSQQPD | 31 |
| MAb20 | WKPRSQQPD | 31 |
| MAb15 | PRSQQPD | 30 |
| MAb16 | PRSQQPD | 30 |

For C-terminal anti-hPG monoclonal antibodies MAbs5-7, 9-12, 14 and 21-23, epitopes comprise at least the following sequences: FGRR (SEQ ID NO:33), MDFGR (SEQ ID NO:34), AEDEN (SEQ ID NO:35), and GWMDFGRR (SEQ ID NO:36), as shown in TABLE 2B, below.

TABLE 2B

| MAb# | PG peptide antigen: QGPWLEEEEEAYGWMDFGRRSAEDEN | SEQ ID NO |
|---|---|---|
| MAb14 | GWMDFGRR | 36 |
| MAb11 | MDFGR | 34 |
| MAb5 | FGRR | 33 |
| MAb6 | FGRR | 33 |
| MAb7 | FGRR | 33 |
| MAb9 | FGRR | 33 |
| MAb10 | FGRR..E | 33 |
| MAb12 | FGRR | 33 |
| MAb23 | AEDEN | 35 |

The epitope mapping experiments reveal that anti-hPG MAb2 and MAb4 bind the same epitope; anti-hPG MAb1 and MAb3 bind approximately the same epitope; MAb17, MAb18, MAb19, and MAb20 bind approximately the same epitope; MAb15 and MAb16 bind approximately the same epitope; anti-hPG MAb5, MAb6, MAb7, MAb9, and MAb12 bind the same epitope and bind approximately the same epitope as anti-hPG MAb10; and anti-hPG MAb11 and MAb14 bind approximately the same epitope.

Specific embodiments of N-terminal anti-PG antibodies useful in the methods and kits described herein include antibodies that bind an epitope that includes residues 10 to 14 of hPG (SEQ ID NO:28), residues 9 to 14 of hPG (SEQ ID NO:29), residues 4 to 10 of hPG (SEQ ID NO:30), residues 2 to 10 of hPG (SEQ ID NO:31), or residues 2 to 14 of hPG (SEQ ID NO:32).

Specific embodiments of C-terminal anti-PG antibodies useful in the methods and kits described herein include antibodies that bind an epitope that includes residues 71 to 74 of hPG (SEQ ID NO:33), residues 69 to 73 of hPG (SEQ ID NO:34), residues 76 to 80 of hPG (SEQ ID NO:35), or residues 67 to 74 of hPG (SEQ ID NO:36).

N-terminal and C-terminal anti-hPG antibodies useful in the methods and kits disclosed herein in addition to those provided in TABLES 1A & 1B can be identified in competitive binding assays with exemplary MAbs 1-23, or with other reference antibodies that bind N- or C-terminal epitopes, as will be described in more detail in a later section.

As demonstrated in the Examples, not all anti-hPG antibodies, even those that exhibit a high degree of specificity and affinity for hPG, neutralize the biological activity of hPG. For example, although anti-hPG MAb14 binds hPG with a $K_D$ of about 6 pM, it did not, at least at the concentration tested, inhibit the growth of colorectal cancer cells in an in vitro assay, whereas other anti-hPG monoclonal antibodies, for example MAb1-MAb13 and MAb15-MAb23, exhibited inhibitory activity to varying degrees. While both non-neutralizing and neutralizing antibodies that specifically bind hPG are useful for the diagnostic methods of the present disclosure, anti-hPG antibodies useful for therapeutic methods should exhibit neutralizing activity.

As used herein, a "neutralizing anti-hPG antibody" is an anti-hPG antibody that yields a statistically significant reduction in the number of live colorectal cancer cells in a test sample treated with the anti-hPG antibody as compared to a control sample treated with a non-specific antibody. A specific assay for assessing the capability of any particular anti-hPG antibody to be neutralizing is described in Example 22. Those anti-hPG antibodies that exhibit at least about a 50% reduction in the number of live colorectal cancer cells in this assay are believed to be especially useful in treating colorectal cancer, although anti-hPG antibodies exhibiting lower levels of neutralizing activity, for example, a statistically significant reduction of 40%, 30%, 20%, 15%, or even 10%, in the number of live colorectal cells in this assay are expected to provide therapeutic benefits. Exemplary cells for use in these assays include, but are not limited to, the primary and metastatic colorectal cancer cell lines described herein.

Accordingly, in some embodiments, for example therapeutic embodiments, useful anti-hPG antibodies are neutralizing. As disclosed herein and in the '329 and '041 applications, the ability of an anti-hPG monoclonal antibody to be neutralizing is not epitope-dependent, as both N-terminal and C-terminal anti-hPG monoclonal antibodies exhibited neutralizing activity in assays with colorectal cancer cells. Thus, in some specific embodiments, the neutralizing anti-hPG antibodies are N-terminal neutralizing anti-hPG antibodies. In other embodiments, the neutralizing anti-hPG antibodies are C-terminal neutralizing anti-hPG antibodies.

The affinity of any specific anti-hPG antibody is not critical. However, for some uses, antibodies exhibiting affinities of at least about 1 µM may be preferred. For therapeutic uses, an affinity of at least about 90 nM, 80 nM, 70 nM, 60 nM, 50 nM, 40 nM, 30 nM, 20 nM, 15 nM, 10 nM, 7 nM, 6 nM, 5 nM, 4 nM, 3 nM, 2 nM, 1 nM, 0.1 nM, 0.01 nM, 0.001 nM or even greater, may be desirable. The measured affinities of the anti-hPG monoclonal antibodies identified in TABLES 1A & 1B range from $10^{-6}$ to $10^{-12}$ M, as noted in TABLE 3, below:

TABLE 3

| Monoclonal Antibody | Affinity constant measured KD (M) |
|---|---|
| Anti-hPG MAb 1 | 2.5 µM ($2.5 \times 10^{-6}$M) |
| Anti-hPG MAb 2 | 185 nM ($1.85 \times 10^{-7}$M) |
| Anti-hPG MAb 3 | 6.4 nM ($6.4 \times 10^{-9}$M) |
| Anti-hPG MAb 4 | 3.5 nM ($3.5 \times 10^{-9}$M) |
| Anti-hPG MAb 5 | 13 pM ($1.30 \times 10^{-11}$M) |
| Anti-hPG MAb 6 | 0.6 nM ($6.38 \times 10^{-10}$M) |
| Anti-hPG MAb 7 | 58 pM ($5.84 \times 10^{-11}$M) |
| Anti-hPG MAb 8 | 0.1 nM ($1.08 \times 10^{-10}$M) |
| Anti-hPG MAb 10 | 3.6 nM ($3.62 \times 10^{-9}$M) |
| Anti-hPG MAb 11 | 0.3 nM ($3.12 \times 10^{-10}$M) |
| Anti-hPG MAb 12 | 0.4 nM ($4.43 \times 10^{-10}$M) |
| Anti-hPG MAb 13 | 0.6 nM ($6.12 \times 10^{-10}$M) |
| Anti-hPG MAb 14 | 6.8 pM ($6.86 \times 10^{-12}$M) |

TABLE 3-continued

| Monoclonal Antibody | Affinity constant measured KD (M) |
|---|---|
| Anti-hPG MAb 15 | 0.2 nM ($2.11 \times 10^{-10}$M) |
| Anti-hPG MAb 16 | 0.2 nM ($2.78 \times 10^{-10}$M) |
| Anti-hPG MAb 17 | 8.3 nM ($8.29 \times 10^{-9}$M) |
| Anti-hPG MAb 18 | 1.2 nM ($1.24 \times 10^{-9}$M) |
| Anti-hPG MAb 19 | 0.7 nM ($7.79 \times 10^{-10}$M) |
| Anti-hPG MAb 20 | 0.2 nM ($2.47 \times 10^{-10}$M) |
| Anti-hPG MAb 21 | 3.9 nM ($3.90 \times 10^{-9}$M) |
| Anti-hPG MAb 22 | 5 nM ($4.94 \times 10^{-9}$M) |
| Anti-hPG MAb 23 | 0.4 µM ($3.99 \times 10^{-7}$M) |

An anti-PG monoclonal antibody having an affinity especially suited for a particular desired application can be readily selected from amongst these, or generated or designed using the various immunogens, complementarity determining region (CDR) sequences, variable heavy ($V_H$) and variable light ($V_L$) chain sequences of anti-hPG antibodies described herein. The affinity of any particular anti-PG monoclonal antibody can be determined using techniques well known in the art or described herein, such as for example, ELISA, isothermal titration calorimetry (ITC), BIAcore, or fluorescent polarization assays. A specific assay is provided in Example 23.

As noted in TABLES 1A & 1B, several N-terminal and C-terminal monoclonal anti-hPG antibodies have been identified. All of these antibodies are specific for hPG and all those listed except MAb14 exhibit neutralizing activity. Several of the hybridomas useful for obtaining the antibodies were deposited on Oct. 6, 2010 with the Collection Nationale de Cultures de Microorganismes (CNCM) in accordance with the Treaty of Budapest. The designated names of the hybridomas producing anti-hPG MAbs1-23 and the depository registration numbers of those hybridomas deposited are provided in TABLES 1A & 1B. In addition, for several of the antibodies, the amino acid sequences of their variable heavy chains ($V_H$), variable light chains ($V_L$), $V_L$ complementarity determining regions (CDRs) and $V_H$ CDRs have been determined. These amino acid sequences, and the shorthand nomenclature used to reference them throughout the disclosure, are also provided in TABLES 1A & 1B. Briefly, murine heavy and light chain variable domains are referred to herein as $mV_H$ and $mV_L$ followed by the number of the corresponding monoclonal antibody, for example $mV_H.3$ and $mV_L.3$ for the variable light and variable heavy chains of anti-hPG MAb3, respectively. Similarly, human heavy and light chain variable domains are referred to herein as $hV_H$ and $hV_L$ followed by the number of the corresponding monoclonal antibody. The three variable heavy chain CDRs and three variable light chain CDRs are referred to as $V_H$ CDR 1, 2, or 3, and $V_L$ CDR 1, 2, or 3, respectively, followed by the number of the specific anti-hPG monoclonal antibody. For example, $V_H$ CDR 1 of MAb3 is denoted $V_H$ CDR 1.3 and $V_L$ CDR 1 of MAb3 is denoted $V_L$ CDR 1.3. $V_H$ CDR 2 of MAb3 is denoted $V_H$ CDR 2.3, and $V_L$ CDR 2 of MAb3 is denoted $V_L$ CDR 2.3.

It is expected that corresponding CDRs and/or $V_H$ and $V_L$ chains of anti-hPG monoclonal antibodies that bind approximately the same epitopes could be interchanged to yield new anti-hPG monoclonal antibodies useful in the methods and kits described herein. For example, as noted above, exemplary anti-hPG monoclonal antibodies MAb5 and MAb6 bind the same epitope. An anti-hPG monoclonal antibody can be designed that includes, in its $V_L$ chain, various combinations of the $V_L$ CDRs of these two antibodies, and/or in its $V_H$ chain various combinations of the $V_H$ CDRs of these two antibodies. As a specific non-limiting example to illustrate the various combinations possible, such an antibody could include in its $V_L$ chain, CDRs 1 and 2 of MAb5 ($V_L$ CDR 1.5 and $V_L$ CDR 2.5, respectively) and CDR 3 of MAb6 ($V_L$ CDR 3.6), and in its $V_H$ chain, CDR 1 of MAb6 ($V_H$ CDR 1.6) and CDRs 2 and 3 of MAb5 ($V_H$ CDR 2.5 and $V_H$ CDR 3.5, respectively).

Amino acid sequences of CDRs of antibodies produced by hybridomas that have been deposited can be obtained using conventional means. For example, relevant sequences of the antibodies produced by hybridomas 6B5B11C10 and 20D2C3G2 were determined as follows. Briefly, total RNA was isolated from frozen cell pellets using RNABee reagent, AMSBio catalogue no. CS-104B, used according to manufacturer's instructions. cDNA for V-regions was prepared from mRNA using reverse-transcriptase polymerase chain reaction (RT-PCR), followed by 5' rapid amplification of cDNA ends (RACE). cDNA synthesis was carried out using constant-region-specific primers, after which the first strand product was purified and terminal deoxynucleotide transferase was used to add homopolymeric tails to the 3' ends of the cDNA. The "tailed" cDNA sequences were then amplified by PCR using primer pairs, one primer each for the homopolymeric tail and either the $V_H$ or $V_L$ region, respectively. Heavy and light chain variable region PCR products were then cloned into a "TA" cloning vector (p-GEM-T easy, Promega cat. no A 1360) and sequenced using standard procedures. See FIG. 31A-B (MAb 3), FIG. 31C-D (MAb 4).

Similarly, relevant sequences of antibodies produced by hybridomas 1C10D3B9, 2C6C3C7, 1B3B4F1, and 1E9D9B61 were determined as follows. Total RNA was isolated from frozen cell pellets using RNAqueous®-4PCR kit (Ambion cat. No. AM1914) used according to manufacturer's instructions. Heavy chain V-region mRNA was amplified using a set of six degenerate primer pools (HA to HF) and light chain V-region mRNA was amplified using a set of eight degenerate primer pools, seven for the κ cluster (KA to KG) and one for the λ cluster (LA). cDNA for variable regions was prepared from mRNA using RT-PCR. cDNA synthesis was carried out using constant-region-specific primers, followed by PCR using pools of degenerate primers for 5' murine signal sequences and primers to 3' constant regions for each of IgGVH, IgκVL and IgλVL. (Jones et al., 1991, *Rapid PCR cloning of full-length mouse immunoglobulin variable regions*, Bio/Technology 9:88-89). Heavy and light chain variable region PCR products were then cloned into a "TA" cloning vector (p-GEM-T easy, Promega cat. no A 1360) and sequenced using standard procedures. See FIGS. 31E-F (MAb 8), 31G-H (MAb 13), 31I-J (Mab 16), and 31K-L (Mab 19).

With reference to TABLE 1A, specific embodiments of N-terminal anti-hPG antibodies useful in the methods and kits described herein include, but are not limited to, the following:

(a) antibodies having $V_L$ CDRs that correspond in sequence to the $V_L$ CDRs of MAb1, MAb2, MAb3, MAb4, MAb15, MAb16, MAb17, MAb18, MAb19 or MAb20, and $V_H$ CDRs that correspond in sequence to the $V_H$ CDRs of MAb1, MAb2, MAb3, MAb4, MAb15, MAb16, MAb17, MAb18, MAb19 or MAb20;

(b) antibodies having $V_L$ CDRs and $V_H$ CDRs that correspond in sequence to the $V_L$ and $V_H$ CDRs of MAb1, MAb2, MAb3, MAb4, MAb15, MAb16, MAb17, MAb18, MAb19 or MAb20;

(c) antibodies in which:
(i) $V_L$ CDR 1 is selected from QSIVHSNGNTY ("$V_L$ CDR 1.3"; SEQ ID NO:4), QSLVHSSGVTY ("$V_L$ CDR 1.4"; SEQ ID NO:10), QSLLDSDGKTY ("$V_L$ CDR 1.16"; SEQ ID NO:50), and SQHRTYT ("$V_L$ CDR 1.19"; SEQ ID NO:51);

(ii) $V_L$ CDR2 is selected from KVS ("$V_L$ CDR 2.3" and ("$V_L$ CDR 2.4"; SEQ ID NO:5), LVS ("$V_L$ CDR 2.16"; SEQ ID NO:53), and VKKDGSH ("$V_L$ CDR 2.19"; SEQ ID NO:54);

(iii) $V_L$ CDR3 is selected from FQGSHVPFT ("$V_L$ CDR\3.3"; SEQ ID NO:6), SQSTHVPPT ("$V_L$ CDR 3.4"; SEQ ID NO:11), WQGTHSPYT ("$V_L$ CDR 3.16"; SEQ ID NO:57), and GVGDAIKGQSVFV ("$V_L$ CDR 3.19"; SEQ ID NO:58);

(iv) $V_H$ CDR1 is selected from GYIFTSYW ("$V_H$ CDR 1.3"; SEQ ID NO:1), GYTFSSSW ("$V_H$ CDR 1.4"; SEQ ID NO:7), GYTFTSYY ("$V_H$ CDR 1.16"; SEQ ID NO:39), and GYSITSDYA ("$V_H$ CDR 1.19"; SEQ ID NO:40);

(v) $V_H$ CDR2 is selected from FYPGNSDS ("$V_H$ CDR 2.3"; SEQ ID NO:2), FLPGSGST ("$V_H$ CDR 2.4"; SEQ ID NO:8), INPSNGGT ("$V_H$ CDR 2.16"; SEQ ID NO:43), and ISFSGYT ("$V_H$ CDR 2.19"; SEQ ID NO:44); and (vi) $V_H$ CDR3 is selected from TRRDSPQY ("$V_H$ CDR 3.3"; SEQ ID NO:3), ATDGNYDWFAY ("$V_H$ CDR 3.4" SEQ ID NO:9), TRGGYYPFDY ("$V_H$ CDR 3.16"; SEQ ID NO:47), and AREVNYGDSYHFDY ("$V_H$ CDR 3.19"; SEQ ID NO:48);

(d) antibodies having a $V_L$ that corresponds in sequence to the $V_L$ of MAb1, MAb2, MAb3, MAb4, MAb15, MAb16, MAb17, MAb18, MAb19 or MAb20 and a $V_H$ that corresponds in sequence to the $V_H$ of MAb1, MAb2, MAb3, MAb4, MAb15, MAb16, MAb17, MAb18, MAb19 or MAb20; and (e) antibodies having a $V_L$ and a $V_H$ that corresponds in sequence to the $V_L$ and $V_H$ of MAb1, MAb2, MAb3, MAb4, MAb15, MAb16, MAb17, MAb18, MAb19 or MAb20.

With reference to TABLE 1B, specific embodiments of C-terminal anti-hPG antibodies useful in the methods and kits described herein include, but are not limited to, the following:

(f) antibodies having $V_L$ CDRs that correspond in sequence to the $V_L$ CDRs of MAb5, MAb6, MAb7, MAb8, MAb9, MAb10, MAb11, MAb12, MAb13, MAb14, MAb21, MAb22 or MAb23 and $V_H$ CDRs that correspond in sequence to the $V_H$ CDRs of MAb5, MAb6, MAb7, MAb8, MAb9, MAb10, MAb11, MAb12, MAb13, MAb14, MAb21, MAb22 or MAb23;

(g) antibodies having $V_L$ CDRs and $V_H$ CDRs that correspond in sequence to the $V_L$ and $V_H$ CDRs of MAb5, MAb6, MAb7, MAb8, MAb9, MAb10, MAb11, MAb12, MAb13, MAb14, MAb21, MAb22 or MAb23;

(h) antibodies in which:
(vii) $V_L$ CDR1 is selected from KSLRHTKGITF ("$V_L$ CDR 1.8"; SEQ ID NO:49) and QSLLDSDGKTY ("$V_L$ CDR 1.13"; SEQ ID NO:50);

(viii) $V_L$ CDR2 is selected from QMS ("$V_L$ CDR 2.8"; SEQ ID NO:52) and LVS ("$V_L$ CDR 2.13"; SEQ ID NO:53);

(ix) $V_L$ CDR3 is selected from AQNLELPLT ("$V_L$ CDR 3.8"; SEQ ID NO:55) and WQGTHFPQT ("$V_L$ CDR 3.13"; SEQ ID NO:56);

(x) $V_H$ CDR1 is selected from GFTFTTYA ("$V_H$ CDR 1.8"; SEQ ID NO:37) and GFIFSSYG ("$V_H$ CDR 1.13"; SEQ ID NO:38);

(xi) $V_H$ CDR2 is selected from ISSGGTYT ("$V_H$ CDR 2.8"; SEQ ID NO:41) and INTFGDRT ("$V_H$ CDR 2.13"; SEQ ID NO:42); and (xii) V$_H$ CDR3 is selected from ATQGNYSLDF ("V$_H$ CDR 3.8"; SEQ ID NO:45) and ARGTGTY ("V$_H$ CDR 3.13"; SEQ ID NO:46);

(i) antibodies having a V$_L$ that corresponds in sequence to the V$_L$ of MAb5, MAb6, MAb7, MAb8, MAb9, MAb10, MAb11, MAb12, MAb13, MAb14, MAb21, MAb22 or MAb23 and a V$_H$ that corresponds in sequence to the V$_H$ of MAb5, MAb6, MAb7, MAb8, MAb9, MAb10, MAb11, MAb12, MAb13, MAb14, MAb21, MAb22 or MAb23; and (j) antibodies having a V$_L$ and a V$_H$ that correspond in sequence to the V$_L$ and V$_H$ that correspond in sequence to the V$_L$ and V$_H$ of MAb5, MAb6, MAb7, MAb8, MAb9, MAb10, MAb11, MAb12, MAb13, MAb14, MAb21, MAb22 or MAb23.

As will be appreciated by skilled artisans, anti-hPG antibodies useful in the diagnostic methods can be of any origin, including, for example, mammalian (e.g., human, primate, rodent, goat or rabbit), non-mammalian, or chimeric in nature (derived from more than one species of origin). Antibodies suitable for therapeutic uses in animals, including humans, are preferably derived from the same species intended to be treated, or have been modified or designed to be non-immunogenic or have reduced immunogenicity in the animal being treated. A specific class of anti-hPG antibodies useful for therapeutic uses in humans is the class of humanized antibodies, discussed in more detail, below. Anti-hPG antibodies useful in the methods and kits described herein can also be of, or derived from, any isotype, including, for example, IgA (e.g., IgA1 or IgA2), IgD, IgE, IgG (e.g., IgG1, IgG2, IgG3 or IgG4) or IgM. Anti-hPG antibodies designed for therapeutic uses are preferably of the IgG isotype.

In some embodiments, anti-hPG antibodies useful for therapeutic methods described herein are humanized. In general, humanized antibodies comprise substantially all of at least one, and typically two, variable domains, in which all or substantially all of the CDR regions correspond to those of a non-human immunoglobulin and all or substantially all of the framework regions are those of a human immunoglobulin consensus sequence, and can be referred to as "CDR-grafted." The humanized antibody can also comprise at least a portion of an immunoglobulin constant region (Fc), typically that of a human immunoglobulin consensus sequence. Methods for humanizing antibodies, including methods for designing humanized antibodies, are well-known in the art. See, e.g., Lefranc et al., 2003, Dev. Comp. Immunol. 27:55-77; Lefranc et al., 2009, Nucl. Acids Res. 37:D1006-1012; Lefranc, 2008, Mol. Biotechnol. 40: 101-111; Riechmann et al., 1988, Nature 332:323-7; U.S. Pat. Nos. 5,530,101, 5,585,089, 5,693,761, 5,693,762 and 6,180,370 to Queen et al.; EP239400; PCT publication WO 91/09967; U.S. Pat. No. 5,225,539; EP592106; EP519596; Padlan, 1991, Mol. Immunol. 28:489-498; Studnicka et al., 1994, Prot. Eng. 7:805-814; Roguska et al., 1994, Proc. Natl. Acad. Sci. 91:969-973; and U.S. Pat. No. 5,565,332, the disclosures of which are hereby incorporated by reference in their entireties.

Humanized versions of antibodies having CDR sequences corresponding to the CDRs of non-human anti-hPG antibodies, including by way of example and not limitation, the various N-terminal anti-hPG monoclonal antibodies provided in TABLE 1A and the various C-terminal anti-hPG monoclonal antibodies provided in TABLE 1B, can be obtained using these well-known methods. Projected sequences for humanized V$_L$ and V$_H$ chains of selected anti-hPG antibodies are provided in TABLES 1A and 1B. Specific examples of humanized antibodies include antibodies comprising:

(k) any three V$_L$ CDRs and any three V$_H$ CDRs disclosed herein;

(l) a heavy chain variable region comprising an amino acid sequence corresponding to SEQ ID NO:21 and a light chain variable region comprising an amino acid sequence corresponding to SEQ ID NO:22;

(m) a heavy chain variable region comprising an amino acid sequence corresponding to SEQ ID NO:23 and a light chain variable region comprising an amino acid sequence corresponding to SEQ ID NO:24;

(n) a heavy chain variable region comprising an amino acid sequence selected from the group consisting of SEQ ID NO:75, 77, and 79 and a light chain variable region comprising an amino acid sequence selected from the group consisting of SEQ ID NO:76 and 78;

(o) a heavy chain variable region comprising an amino acid sequence selected from the group consisting of SEQ ID NO:80 and 82 and a light chain variable region comprising an amino acid sequence selected from the group consisting of SEQ ID NO:81 and 83;

(p) a heavy chain variable region comprising an amino acid sequence selected from the group consisting of SEQ ID NO:84, 86, and 88 and a light chain variable region comprising an amino acid sequence selected from the group consisting of SEQ ID NO:85, 87, and 89; and (q) a heavy chain variable region comprising an amino acid sequence selected from the group consisting of SEQ ID NO:90, 92, and 94 and a light chain variable region comprising an amino acid sequence selected from the group consisting of SEQ ID NO:91, 93, and 95.

As will be recognized by skilled artisans, anti-hPG antibodies having specific binding properties, such as the ability to bind a specific epitope of interest, can be readily obtained using the various antigens and immunogens described herein and assessing their ability to compete for binding hPG with a reference antibody of interest. Any of the anti-hPG antibodies described herein can be utilized as a reference antibody in such a competition assay. A specific assay useful for assessing the ability of an antibody to compete for binding hPG with a biotinylated reference anti-hPG antibody of interest is provided in Example 24.

In conducting an antibody competition study between a reference anti-hPG antibody and any test antibody (irrespective of species or isotype), one may first label the reference with a label detectable either directly, such as, for example, a radioisotope or fluorophore, or indirectly, such as, for example biotin (detectable via binding with fluorescently-labeled streptavidin) or an enzyme (detectable via an enzymatic reaction), to enable subsequent identification. In this case, a labeled reference anti-hPG antibody (in fixed or increasing concentrations) is incubated with a known amount of hPG, forming a hPG:labeled anti-hPG antibody complex. The unlabeled test antibody is then added to the complex. The intensity of the complexed label is measured. If the test antibody competes with the labeled reference anti-hPG antibody for hPG by binding to an overlapping epitope, the intensity of the complexed label will be decrease relative to a control experiment carried out in the absence of test antibody.

Numerous methods for carrying out binding competition assays are known and can be adapted to yield results comparable to the assay described above and in Example 24.

An antibody is considered to compete for binding hPG with a reference anti-hPG antibody, and thus considered to bind approximately the same or an overlapping epitope of hPG as the reference anti-hPG antibody, if it reduces binding of the reference anti-hPG antibody to hPG in a competitive binding assay, and specifically the competitive binding assay of Example 24, by at least 50%, at a test antibody concentration in the range of 0.01-100 µg/mL (e.g., 0.01 µg/mL, 0.08 µg/mL, 0.4 µg/mL, 2 µg/mL, 10 µg/mL, 50 µg/mL or 100 µg/mL or other concentration within the stated range), although higher levels of reduction, for example, 60%, 70%, 80%, 90% or even 100%, may be desirable.

Antibodies of the present disclosure can also be derivatized, covalently modified, or conjugated to other molecules to alter their properties or improve their function. For example, but not by way of limitation, derivatized antibodies include antibodies that have been modified, e.g., by glycosylation, fucosylation, acetylation, pegylation, phosphorylation, amidation, formylation, derivatization by known protecting/blocking groups, linkage to a cellular ligand or other protein, etc. Alternatively, specific amino acids in the variable or constant regions can be altered to change or improve function. In one non-limiting example, amino acid residues in the Fc region of an antibody may be altered to increase the serum half-life of the antibody by increasing its binding to FcRn.

Anti-hPG monoclonal antibodies include antibodies labeled with a detectable moiety. Such a label can be conjugated directly or indirectly to an anti-hPG monoclonal antibody of the disclosure. The label can itself be detectable (e.g., radioisotope labels, isotopic labels, or fluorescent labels) or, in the case of an enzymatic label, can catalyze chemical alteration of a substrate compound or composition which is detectable. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions.

Although the various anti-hPG antibodies useful in the methods and kits described herein have been exemplified with full length antibodies, skilled artisans will appreciate that binding fragments, or surrogate antibodies designed or derived from full-length antibodies or binding fragments, may also be used. Suitable fragments, surrogates, etc., include, but are not limited to, Fab', F(ab')$_2$, Fab, Fv, vIgG, scFv fragments and surrobodies, rIgG, disulfide-stabilized Fv antibodies (dsFv), diabodies, triabodies, and single domain antibodies, such as a camelized antibody or nanobody.

Antibodies of the present disclosure can be produced according to any way known to those of ordinarily skill in the art. In one non-limiting example, antibodies may be obtained from natural sources, including from any species capable of producing antibodies, such as antibodies derived from humans, simians, chicken, goats, rabbits, and rodents (e.g., rats, mice, and hamsters). Other species are also possible. Antibodies may also be generated and isolated from systems that utilize genetic engineering or recombinant DNA technology, such as, but not limited to, expression of recombinant antibodies in yeast cells, bacterial cells, and mammalian cells in culture, such as CHO cells. Antibodies may also be fully or partially synthetic.

Monoclonal antibodies (MAb) of the present disclosure are not limited to antibodies produced through hybridoma technology. A monoclonal antibody is derived from a single clone, including any eukaryotic, prokaryotic, or phage clone, by any means available or known in the art. Monoclonal antibodies can be prepared using a wide variety of techniques known in the art including the use of hybridoma, recombinant, and phage display technologies, or a combination thereof.

Conventional Treatments for Metastatic Colorectal Cancer

Metastatic colorectal cancer may be treated with biological therapy, targeted therapy, antibody therapy, radiation therapy, chemotherapy, surgery, cryosurgery, or a combination of these. Other treatments for metastatic colorectal cancer are also possible.

Biological therapy is treatment to boost or restore the ability of the immune system to fight cancer. Agents used in biological therapy include biological response modifiers, such as interferons, interleukins, colony-stimulating factors, monoclonal antibodies, vaccines, gene therapy, and nonspecific immunomodulating agents. Some of these agents may also have a direct antitumor effect. Targeted cancer therapies are drugs or other substances that block the growth and spread of cancer by interfering with specific molecules involved in tumor growth and progression.

Antibody therapy involves administration of an antibody, including but not limited to monoclonal antibodies, that directly or indirectly kill, slow or stop the growth of metastatic colorectal cancer cells. Such antibodies can function through a variety of distinct mechanisms. For example, certain antibodies can mark cancer cells for attack by the patient's immune system via antibody-dependent cell-mediated cytotoxicity (ADCC) or other mechanisms. Other antibodies bind to and alter or inhibit the function of antigens that cancer cells require for survival or growth. A number of antibodies are believed to function this way, including, for example, bevacizumab (Avastin®), which binds to the growth factor VEGF. Other mechanisms are also possible, and particular antibodies may be able to work via one or more mechanisms of action. Yet other antibodies can be conjugated to radioactive or chemotoxic moieties and target them to cancer cells which preferentially express antigens specifically recognized by the antibodies. Bevacizumab, cetuximab and panitumumab, are specific examples of antibodies useful in treating metastatic colorectal cancer.

Radiation therapy is the use of high-energy radiation from x-rays, gamma rays, neutrons, protons, and other sources to kill cancer cells and shrink tumors. Radiation may come from a machine outside the body (external-beam radiation therapy), or it may come from radioactive material placed in the body near cancer cells (internal radiation therapy, or brachytherapy). Systemic radiation therapy uses a radioactive substance, such as a radiolabeled monoclonal antibody, that travels in the blood to tissues throughout the body. Radiation therapy may also be called irradiation and radiotherapy. Other radiation therapies include three-dimensional conformal radiation therapy (3D-CRT) and intensity modulated radiation therapy (IMRT). Other radiation therapies are also possible.

Chemotherapy is the use of small organic molecule drugs that kill (cytotoxic or cytocidal) or prevent the growth (cytostatic) of cancer cells. Many chemotherapeutic agents, which mediate their anti-tumor effect through a variety of mechanisms, are available for treatment of metastatic colorectal cancer.

Exemplary chemotherapeutic agents include the following: folate antagonists, including methotrexate and pemetrexed; purine antagonists, including cladribine, clofarabine, fludarabine, 6-mercaptopurine, nelarabine, pentostatin; pyrimidine antagonists, including capecitabine, cytarabine, 5-fluorouracil, gemcitabine, hydroxyurea; bleomycin; DNA alkylating agents, including nitrosureas, carmustine, lomustine; DNA cross-linking drugs and alkylating agents, including bendamustine, chlorambucil, cyclophosphamide, ifosfamide, mechlorethamine (nitrogen mustard), melphalan, dacarbazine, temozolomide, procarbazine; asparaginase; antibiotics, including mitomycin; platinum complexes, including carboplatin, cisplatin, oxaliplatin; proteosome inhibitors, including bortezomib; spindle poisons, such as the taxanes (including docetaxel, paclitaxel) and the vincas (including vinblastine, vincristine, vinorelbine); topoisomerase inhibitors, such as the anthracyclines (including daunorubicin, daunomycin, doxorubicin, epirubicin), the camptothecines, (including irinotecan and topotecan), the podophyllotoxins (including etoposide, teniposide and mitoxantrone). Other chemotherapeutic agents are also possible.

Metastatic colorectal cancer is often treated using chemotherapy agents in combination with each other and/or antibodies. Examples of such combinations include 5-fluorouracil (5FU) combined with leucovorin (folinic acid or LV); tegafur combined with uracil (UFT) and leucovorin; oxaliplatin combined with 5FU, or in further combination with capecitabine; irinotecan combined with capecitabine; mitomycin C combined with 5FU, irinotecan or capecitabine; FOLFOX (leucovorin (folinic acid), 5-FU, and oxaliplatin) by itself, or combined with bevacizumab or cetuximab; FOLFIRI (leucovorin, 5-FU, and irinotecan) by itself, or combined with bevacizumab or cetuximab; CapeOX (capecitabine and oxaliplatin) by itself, or combined with bevacizumab or cetuximab; 5-FU and leucovorin, combined with bevacizumab; capecitabine combined with bevacizumab; FOLFOXIRI (leucovorin, 5-FU, oxaliplatin, and irinotecan); irinotecan combined with cetuximab. Other combination regimens include 5FU Mayo, 5FU Roswell Park, LVFU2, FOLFOX4, FOLFOX6, bFOL, FUFOX, IFL, XELOX, XELIRI, and CAPIRI, which are described in further detail in Chau, I., and Cunningham, D., *Br. J. Cancer* 100 (2009) 1704-19; and Field, K. and Lipton, L., *World J. Gastroenterol.* 13 (2007) 3806-15, which are incorporated by reference. Other combinations of chemotherapy agents and other therapeutic agents are also possible.

Therapeutic Methods Using Anti-PG Antibodies

The present disclosure provides for therapeutic methods comprising administering an anti-PG antibody in a composition to a subject for purposes of treating and preventing metastatic colorectal cancer, preventing recurrence of colorectal cancer and preventing growth of colorectal cancer stem cells. In certain embodiments the antibodies are specific for human progastrin ("hPG") and in other embodiments such antibodies are monoclonal antibodies.

According to certain of these embodiments, anti-PG antibodies as disclosed herein are administered in a composition to a subject in need of treatment for metastatic colorectal cancer in a therapeutically effective amount as a monotherapy or as a combination therapy. Such subjects include, but are not limited to those diagnosed with metastatic colorectal cancer. In certain embodiments of these methods, the antibodies are anti-hPG monoclonal antibodies.

According to other embodiments, anti-PG antibodies as disclosed herein are administered in a composition to a subject in need of prevention of metastatic colorectal cancer in a therapeutically effective amount as a monotherapy or as a combination therapy. Such subjects include, but are not limited to those determined to have primary colorectal cancer but in whom the cancer is not known to have spread to distant tissues or organs. In certain embodiments of these methods, the antibodies are anti-hPG monoclonal antibodies.

According to yet other embodiments, anti-PG antibodies as disclosed herein are administered in a composition to a subject in need of prevention for recurrence of metastatic colorectal cancer in a therapeutically effective amount as a monotherapy or as a combination therapy. Such subjects include, but are not limited to those who were previously treated for primary or metastatic colorectal cancer, after which treatment such cancer apparently disappeared. In certain embodiments of these methods, the antibodies are anti-hPG monoclonal antibodies.

According to other embodiments, anti-PG antibodies as disclosed herein are administered in a composition to a subject in need of inhibition of the growth of colorectal cancer stem cells in a therapeutically effective amount as a monotherapy or as a combination therapy. Such subjects include, but are not limited to those having a colorectal cancer the growth or metastasis of which is at least partly attributable to the presence within it of cancer stem cells. Other embodiments provide for methods of preventing or inhibiting the growth of colorectal cancer stem cells by contacting such stem cells with an amount of an anti-PG antibody composition effective to prevent or inhibit the growth of such cells. Such methods can be carried out in vitro or in vivo. In certain embodiments of these methods, the antibodies are anti-hPG monoclonal antibodies.

Neutralizing anti-PG antibodies will be the primary active agents in therapeutic antibody compositions, although non-neutralizing anti-PG antibodies may be present if their presence does not substantially inhibit the therapeutic efficacy of the neutralizing antibodies.

The subject to whom anti-PG antibody compositions can be administered may be a mammal such as a non-primate (e.g., cow, pig, horse, cat, dog, rat, etc.) or a primate (e.g., monkey, chimpanzee, ape or human). The subject can be a human, such as an adult patient or a pediatric patient.

For purposes of treating or preventing metastatic colorectal cancer or preventing colorectal cancer recurrence, anti-PG antibody compositions can be administered alone to subjects as a monotherapy, or as an adjunct to one or more primary therapies effective to treat or prevent metastatic colorectal cancer or to prevent colorectal cancer recurrence.

Thus, in certain embodiments of the present disclosure, anti-hPG antibody compositions can be administered to a subject in need of treating or preventing metastatic colorectal cancer as an adjunct to chemotherapy, as an adjunct to radiation therapy, as an adjunct to biological therapy, as an adjunct to surgical therapy, or as an adjunct to other types of antibody therapy effective to treat or prevent metastatic colorectal cancer. In yet other embodiments, anti-hPG antibody compositions can be administered to a subject in need of preventing recurrence of colorectal cancer as an adjunct to other therapies effective for preventing such recurrence.

As an adjunctive therapy, anti-hPG antibody compositions can be administered concurrently, successively, or separately with the primary therapy.

Anti-hPG antibody compositions and the primary therapy are administered concurrently when administered at the same time, even where the respective administrations overlap, but begin or end at different times. Non-limiting examples of concurrent administration is administration of an anti-hPG antibody composition at the same time a subject is receiving chemotherapy for metastatic colorectal cancer or undergoing surgical resection of a primary colorectal tumor.

Anti-hPG antibody compositions and the primary therapy are administered successively when administered to a subject on the same day, for example during the same clinic visit, but not concurrently. Successive administration can occur 1, 2, 3, 4, 5, 6, 7, 8 or more hours apart. The primary therapy may be administered first, followed by administration of the anti-hPG antibody composition. In an alternative embodiment, the anti-hPG antibody composition may be administered first, followed by the primary therapy.

Anti-hPG antibody compositions and the primary therapy are administered separately when they are administered to a subject on different days. In certain embodiments, the anti-hPG antibody composition and primary therapy can be administered in an interval of 1-day, 2-days, 3-days, 4-days, 5-days, 6-days, one-week, 2-weeks, 3-weeks or a month or more. As with successive administration, administration of the anti-hPG antibody composition can precede or follow the separate administration of the primary therapy.

In certain other embodiments of the present disclosure, an anti-hPG antibody composition and the primary therapy can be administered repeatedly in an alternating pattern, whether administered successively or separately.

In certain embodiments, administering an anti-hPG antibody composition as an adjunct to a primary therapy may yield a greater than additive, or synergistic, effect providing therapeutic benefit where neither therapy could alone be administered in an amount that would be therapeutically effective without incurring unacceptable side effects. Under these circumstances, the anti-hPG antibody composition and/or primary therapy can be administered in lower amounts, thereby reducing the possibility or severity of adverse effects. However, a synergistic effect is not required for adjunctive therapy with an anti-hPG antibody composition to be therapeutically effective.

7.7. Methods of Monitoring the Efficacy of Metastatic Colorectal Cancer Treatment As noted above, patients with primary and/or metastatic colorectal cancer have elevated plasma and/or serum levels of PG whereas the baseline level of PG in healthy individuals is negligible. PG plasma and/or serum levels in subjects with primary and/or metastatic colorectal cancer are measureable and are about 25 pM or greater. Based on this observation, plasma and/or serum levels of PG can be used to, among other things, monitor the effectiveness of treatments for primary or metastatic colorectal cancer, detect and diagnose the presence of primary or metastatic colorectal cancer, and select subjects that might benefit from treatment with anti-PG antibodies.

Thus, the present disclosure provides methods of monitoring a subject being treated for colorectal metastatic cancer to determine the effectiveness of a prior round of therapy for metastatic colorectal cancer. These methods can be used for any type of therapy against metastatic colorectal cancer, used alone, or in combination with others, including but not limited to administration of an anti-hPG antibody composition, therapy with other types of antibodies, chemotherapy, radiation therapy, biological therapy and others. After a round of therapy is complete, the treatment team responsible for a subject's care needs to ascertain if it was effective to determine whether or not to administer a new round of treatment and make other clinical decisions.

In some embodiments of the monitoring methods, the concentration of PG in one or more bodily fluids, such as blood, plasma, serum or others, can be measured before a treatment for metastatic colorectal cancer is started and then compared to the level of PG measured in the same type of bodily fluid some time after treatment is complete. In other embodiments, PG levels in a tissue of interest, such as biopsies of a colorectal cancer, are measured.

A reduction in PG concentration is indicative of efficacy. Typically, the greater the extent of reduction in PG treatment post-treatment, the more efficacious was the therapy. Without wishing to be bound by any particular theory of operation, it is believed that as the number and/or size of metastases in a patient is reduced as a result of an efficacious treatment, the total amount of PG produced by the metastases also declines. By contrast, a lack of reduction or a rise in PG levels after treatment is complete may indicate that the therapy was not effective. Based on this information, the treatment team can decide whether to initiate a new round of therapy.

Suitable intervals after a round of therapy is complete before which time samples are taken for monitoring are readily determined by those of ordinary skill in the art, and depend on such variables as the type of therapy under consideration, gender and age of the subject and others. Exemplary intervals include 1, 2, 3, 4, 5, 6, 7, 8, 9, 10 or 11 weeks and 3, 4, 5 or 6 months after a round of therapy is complete before samples are taken for use in the monitoring methods of the present disclosure. Other intervals are also possible. In other embodiments, multiple measurements at different intervals after completion of therapy may be taken, and then graphed to determine if a trend exists. In a non-limiting example, PG levels can be determined weekly or monthly for the first six months after a round of therapy is concluded. Other intervals are also possible.

PG concentration levels in bodily fluids can be measured using analytical techniques familiar to those of ordinary skill in the art, such as, but not limited to, RIA and ELISA. Assay methods, such as these, that rely on antibodies specific for hPG can be carried out using non-neutralizing or neutralizing antibodies, such as those disclosed herein, in accordance with the knowledge of those of ordinary skill in the art.

In a specific embodiment, PG levels may be measured using a sandwich ELISA with one anti-PG antibody targeting the N-terminus of progastrin and a second anti-PG antibody targeting the C-terminus of progastrin. Exemplary N- and C-terminal anti-PG antibodies useful for such a sandwich assay are described in a later section. In such an assay, surface, such as the wells in a 96-well plate, is prepared to which a known quantity of a first, "capture," N-terminal or C-terminal anti-PG antibody is bound. A test sample is then applied to the surface followed by an incubation period. The surface is then washed to remove unbound antigen and a solution containing a second, "detection," anti-PG antibody is applied, where the detection antibody binds a different epitope of PG (for example, if the capture antibody is a C-terminal anti-PG antibody, an N-terminal anti-PG antibody is used as the detection antibody, and vice versa). PG levels are then measured either directly (if, for example, the detection antibody is conjugated to a detectable label) or indirectly (through a labeled secondary antibody that binds the detection anti-PG antibody). A specific sandwich assay for measuring plasma and/or serum PG levels is provided in Example 20.

In an alternative embodiment of the methods of the present disclosure, the efficacy of administration of an anti-hPG antibody composition to a subject in reducing PG levels in a bodily fluid of interest may be monitored. In these methods, samples may be taken over time and PG concentrations graphed to assess trends. Where residual anti-hPG antibodies are present, the data may show a reduction in PG levels due to sequestration of PG by the antibodies, followed by a rise as this effect abates, followed by a subsequent decline if the treatment was effective to treat metastatic colorectal cancer.

According to other embodiments of the methods of the present disclosure, a blood, serum or plasma PG concentration below a predetermined threshold of less than about 50 pM, 40 pM, 30 pM, 20 pM, 10 pM, 5 pM, 2 pM, 1 pM or less is indicative of efficacy for treating metastatic colorectal cancer. Other PG concentration thresholds indicative of efficacy are also possible and are readily determined by those of ordinary skill in the art.

7.8. Methods of Determining the Presence of Colorectal Cancer

The present disclosure also provides certain embodiments according to which subjects may be tested to determine if they have elevated PG levels in a bodily fluid, such as blood, plasma, serum, or others, compared to an appropriate baseline, for purposes of detecting the presence of primary or metastatic colorectal cancer or recurrence of colorectal cancer after treatment.

In certain embodiments of the methods of the present disclosure, the subject may be one for whom it is desired to be determined whether colorectal cancer, primary or metastatic, is present in the subject. In such subjects, elevated PG levels relative to baseline indicates that colorectal cancer is present. Without wishing to be bound by any particular theory of operation, it is believed that as the size and/or extent of colorectal cancer in a subject increases, systemic and/or localized PG levels also increase in the subject.

In other embodiments, the subject may be one previously treated for primary colorectal cancer for whom it is desired to be determined whether the colorectal cancer has metastasized to distant tissues or organs. In such subjects, elevated PG levels relative to baseline indicates that metastatic colorectal cancer is present. For such subjects as well, the methods of the present disclosure are useful, among other things, for determining whether or not a treatment intended to prevent metastatic colorectal cancer was effective. Without wishing to be bound by any particular theory of operation, it is believed that as the number and/or size of metastases in a subject increases, systemic and/or localized PG levels also increase in the subject.

According to yet other embodiments, the subject may be one previously treated for colorectal cancer, primary or metastatic, in whom the cancer apparently disappeared and in whom it is desired to be determined whether colorectal cancer has recurred or come back. In such subjects, elevated PG levels relative to baseline indicates that colorectal cancer has recurred. Without wishing to be bound by any particular theory of operation, it is believed that as the size and/or extent of recurrent colorectal cancer in a subject increases, systemic and/or localized PG levels also increase in the subject.

In view of the discoveries described herein that metastatic colorectal cancers secrete PG and are PG-sensitive, the present disclosure also provides methods of selecting subjects that may benefit from therapy by administering anti-PG antibodies. Thus, subjects may be screened by care providers to detect if they have elevated plasma and/or serum PG levels relative to a baseline. Once such subjects are identified, care providers can order additional tests to confirm the presence of metastatic colorectal cancer in the subject. If metastatic colorectal cancer is confirmed then treatment, including administration of anti-hPG antibodies, can be commenced.

In certain embodiments of the methods for selecting subjects, screening may be performed as part of a routine check up by the subject's primary care physician or as part of public health initiatives that target larger populations of subjects. In other embodiments, the subjects to be screened are members of particular subpopulations with higher then average risk of developing metastatic colorectal cancer. Such groups include, but are not limited to, subjects having close relatives (parents, brothers, sisters, or children) who have had colorectal cancer, subjects having a history of colorectal polyps, subjects that are obese, subjects that smoke and subjects that are physically inactive. Other such subjects are those diagnosed with ulcerative colitis, Crohn's disease, or familial adenomatous polyposis (FAP), or those having mutations in the HNPCC gene, mutations in the APC gene, or other genes associated with increased risk of colorectal cancer. Yet other groups include subjects formerly diagnosed and successfully treated for colorectal cancer.

PG concentrations can be measured using techniques familiar to those of ordinary skill, such as, but not limited to, RIA and ELISA. Assay methods, such as these, that rely on antibodies specific for hPG can be carried out using non-neutralizing or neutralizing antibodies, such as those disclosed herein, in accordance with the knowledge of those of ordinary skill in the art.

Based on the detection of elevated PG levels using the methods of the present disclosure, the treatment team can then decide whether to undertake additional tests to confirm the presence of colorectal cancer or recurrence of colorectal cancer after treatment, or proceed directly to treating the subject.

Different baselines may be used against which to compare PG levels measured in a subject. In some embodiments of the methods of the present disclosure, the baseline is established by measuring PG levels in a bodily fluid of interest sampled from the same subject at prior times. Such samples may be taken, and PG levels measured, at predetermined intervals. In a non-limiting example, PG levels are measured weekly or monthly for the first six months after the end of a treatment, then once every three months until the second anniversary of the end of the treatment, and then every six months or year thereafter. Other predetermined intervals are also possible.

In other embodiments of the methods of the present disclosure, the baseline can be established from average PG levels in a population of individuals with characteristics similar to those of the subject undergoing sampling for detection of colorectal cancer metastasis or recurrence. Such characteristics may include but are not necessarily limited to sex, age, stage of the primary colorectal tumor, prior exposure to certain treatments, combinations of these or other factors. In yet other embodiments, both a subject-specific baseline, as well as a population-derived baseline can be used in assessing the condition of a subject.

In accordance with the knowledge of those ordinarily skilled in the art, PG levels in samples from a subject that exceed a certain threshold relative to a baseline are concluded as having colorectal cancer or colorectal cancer that has recurred after treatment. The treatment team may then undertake confirmatory tests to confirm presence of colorectal cancer. Non-limiting examples of such tests include exploratory surgery to detect colorectal cancer, a medical imaging test to detect colorectal cancer, a test of the subject's stool to detect occult blood, a colonoscopy, a test of a sample obtained from a subject for the presence of gene mutations, such as in the HNPCC gene or APC gene, that are indicative of increased risk colorectal cancer, and a test of a sample obtained from a subject for the presence of biological factor, such as carcinoembryonic antigen (CEA), that is indicative of colorectal cancer.

Because eating usually increases gastrin synthesis and secretion, eating may result in transient increases in blood PG levels which may interfere with the accurate measurement of PG produced by colorectal cancer metastases or recurrent colorectal cancer. To avoid this effect, particularly where PG levels in plasma and/or serum is to be determined, samples can be taken from subjects after fasting for sufficient time, as can readily be determined by those of ordinary skill in the art.

7.9. Pharmaceutical Compositions

Anti-hPG antibodies for use in the methods of the present disclosure can be formulated as compositions. Optionally, the compositions can comprise one or more additional therapeutic agents, such as chemotherapeutic agents or other antibodies with therapeutic efficacy against metastatic colorectal cancer or colorectal cancer recurrence. The compositions will usually be supplied as part of a sterile, pharmaceutical composition that will normally include a pharmaceutically acceptable carrier. This composition can be in any suitable form depending upon the desired method of administering it to a patient.

The anti-PG antibodies can be administered to a subject by a variety of routes, typically parenterally, for example, via subcutaneous, intravenous, intraperitoneal or intramuscular injection. Administration can be effected as one or more bolus injections, or as one or more infusions. Other routes of administration are also possible in accordance with the knowledge of those ordinarily skilled in the art. The most suitable route for administration in any given case may depend on the particular composition to be administered and characteristics of the subject, such as age or sex.

Pharmaceutical compositions can be conveniently presented in unit dose forms containing a predetermined amount of an anti-hPG antibody of the disclosure per dose. Such a unit can contain for example but without limitation 5 mg to 5 g, for example 10 mg to 1 g, or 20 to 50 mg. Pharmaceutically acceptable carriers for use in the disclosure can take a wide variety of forms depending, e.g., on the route of administration.

Pharmaceutical compositions of the disclosure can be prepared for storage as lyophilized formulations or aqueous solutions by mixing the antibody having the desired degree of purity with optional pharmaceutically acceptable carriers, excipients or stabilizers typically employed in the art (all of which are referred to herein as "carriers"), i.e., buffering agents, stabilizing agents, preservatives, isotonifiers, nonionic detergents, antioxidants, and other miscellaneous additives. See, *Remington's Pharmaceutical Sciences,* 16th edition (Osol, ed. 1980). Such additives must be nontoxic to the recipients at the dosages and concentrations employed.

Buffering agents help to maintain the pH in the range which approximates physiological conditions. They can be present at concentration ranging from about 2 mM to about 50 mM. Suitable buffering agents for use with the present disclosure include both organic and inorganic acids and salts thereof such as citrate buffers (e.g., monosodium citrate-disodium citrate mixture, citric acid-trisodium citrate mixture, citric acid-monosodium citrate mixture, etc.), succinate buffers (e.g., succinic acid-monosodium succinate mixture, succinic acid-sodium hydroxide mixture, succinic acid-disodium succinate mixture, etc.), tartrate buffers (e.g., tartaric acid-sodium tartrate mixture, tartaric acid-potassium tartrate mixture, tartaric acid-sodium hydroxide mixture, etc.), fumarate buffers (e.g., fumaric acid-monosodium fumarate mixture, fumaric acid-disodium fumarate mixture, monosodium fumarate-disodium fumarate mixture, etc.), gluconate buffers (e.g., gluconic acid-sodium glyconate mixture, gluconic acid-sodium hydroxide mixture, gluconic acid-potassium glyuconate mixture, etc.), oxalate buffer (e.g., oxalic acid-sodium oxalate mixture, oxalic acid-sodium hydroxide mixture, oxalic acid-potassium oxalate mixture, etc.), lactate buffers (e.g., lactic acid-sodium lactate mixture, lactic acid-sodium hydroxide mixture, lactic acid-potassium lactate mixture, etc.) and acetate buffers (e.g., acetic acid-sodium acetate mixture, acetic acid-sodium hydroxide mixture, etc.). Additionally, phosphate buffers, histidine buffers and trimethylamine salts such as Tris can be used.

Preservatives can be added to retard microbial growth, and can be added in amounts ranging from 0.2%-4% (w/v). Suitable preservatives for use with the present disclosure include phenol, benzyl alcohol, meta-cresol, methyl paraben, propyl paraben, octadecyldimethylbenzyl ammonium chloride, benzalconium halides (e.g., chloride, bromide, and iodide), hexamethonium chloride, and alkyl parabens such as methyl or propyl paraben, catechol, resorcinol, cyclohexanol, and 3-pentanol. Isotonicifiers sometimes known as "stabilizers" can be added to ensure isotonicity of liquid compositions of the present disclosure and include polhydric sugar alcohols, for example trihydric or higher sugar alcohols, such as glycerin, erythritol, arabitol, xylitol, sorbitol and mannitol. Stabilizers refer to a broad category of excipients which can range in function from a bulking agent to an additive which solubilizes the therapeutic agent or helps to prevent denaturation or adherence to the container wall. Typical stabilizers can be polyhydric sugar alcohols (enumerated above); amino acids such as arginine, lysine, glycine, glutamine, asparagine, histidine, alanine, ornithine, L-leucine, 2-phenylalanine, glutamic acid, threonine, etc., organic sugars or sugar alcohols, such as lactose, trehalose, stachyose, mannitol, sorbitol, xylitol, ribitol, myoinisitol, galactitol, glycerol and the like, including cyclitols such as inositol; polyethylene glycol; amino acid polymers; sulfur containing reducing agents, such as urea, glutathione, thioctic acid, sodium thioglycolate, thioglycerol, α-monothioglycerol and sodium thio sulfate; low molecular weight polypeptides (e.g., peptides of 10 residues or fewer); proteins such as human serum albumin, bovine serum albumin, gelatin or immunoglobulins; hydrophilic polymers, such as polyvinylpyrrolidone monosaccharides, such as xylose, mannose, fructose, glucose; disaccharides such as lactose, maltose, sucrose and trisaccacharides such as raffinose; and polysaccharides such as dextran. Stabilizers can be present in the range from 0.1 to 10,000 weights per part of weight active protein.

Non-ionic surfactants or detergents (also known as "wetting agents") can be added to help solubilize the therapeutic agent as well as to protect the therapeutic protein against agitation-induced aggregation, which also permits the formulation to be exposed to shear surface stressed without causing denaturation of the protein. Suitable non-ionic surfactants include polysorbates (20, 80, etc.), polyoxamers (184, 188, etc.), Pluronic polyols, polyoxyethylene sorbitan monoethers (TWEEN®-20, TWEEN®-80, etc.). Non-ionic surfactants can be present in a range of about 0.05 mg/ml to about 1.0 mg/ml, for example about 0.07 mg/ml to about 0.2 mg/ml. Surfactants have a tendency, however, to bind to antibodies, and can compromise their conformations. Therefore, when used, stabilizing concentrations should be low and discerned experimentally.

Additional miscellaneous excipients can include chelating agents (e.g., EDTA), antioxidants (e.g., ascorbic acid, methionine, vitamin E), and cosolvents.

Anti-hPG antibodies can be administered singly or as mixtures of one or more anti-hPG antibodies alone, or in mixture or combination with other agents useful for preventing colorectal cancer metastasis or recurrence, including but not limited to chemotherapeutic agents, biological therapy agents, and antibody therapy agents (e.g., bevacizumab).

7.10. Pharmaceutical Kits

In certain embodiments, the invention provides for pharmaceutical kits for use by clinicians or others. The pharmaceutical kit is a package comprising an anti-hPG antibody of the disclosure (e.g., either in lyophilized form or as an aqueous solution) and one or more of the following: at least a second therapeutic agent as described elsewhere in this disclosure; a device for administering the anti-hPG antibody, e.g., a needle and/or syringe; and pharmaceutical grade water or buffer to resuspend or dilute the antibody if the antibody is in lyophilized or concentrated form. Kits may also include instructions for preparing the antibody composition and/or administering the composition to a patient.

Each unit dose of the anti-hPG antibody composition can be packaged separately, and a kit can contain one or more unit doses (e.g., two unit doses, three unit doses, four unit doses, five unit doses, seven unit doses, eight unit doses, ten unit doses, or more). In one embodiment, the one or more unit doses are each housed in a syringe, and in another embodiment, the one or more unit doses are each contained in a bag or similar receptacle suitable for connecting to an I.V. line.

7.11. Effective Dosages

Compositions comprising neutralizing anti-hPG antibodies of the present disclosure are generally to be administered to a subject in need of treating or preventing colorectal cancer metastasis or preventing recurrence of colorectal cancer in a dosage effective to achieve, at least partially, the desired outcome.

With respect to treating colorectal cancer metastasis, therapeutic benefit means, among other things, any amelioration of metastatic colorectal cancer, halting or slowing the growth of colorectal cancer metastases, reducing the number and/or size of such metastases within a subject, reducing blood flow to colorectal cancer metastases, reducing the metabolism of colorectal cancer metastases, reducing the severity of colorectal cancer metastatic cancer, inhibiting the proliferation of or increasing apoptosis of metastatic colorectal cancer cells, halting or delaying aggravation of the symptoms or signs associated with metastatic colorectal cancer in a subject, allowing surgical resection of colorectal cancer metastases where such resection would not have been possible before treatment, increasing the life expectancy, comfort or quality of life of a subject having metastatic colorectal cancer, or reducing pain in such a subject. A complete cure of metastatic colorectal cancer, while desirable, is not required for therapeutic benefit to exist.

Therapeutic benefit can also be measured in terms of progression-free survival (PFS). In this context, one measures how long it takes for a subject initially having Stage II, III or IV colorectal cancer to progress to a more advanced stage of the disease. An increase in PFS of 3, 4, 5, 6, 7, 8, 9, 10 or more months is considered to provide therapeutic benefit.

Metastatic colorectal cancer tumor size, number and metabolism can be measured using various scanning techniques, including, but not limited to, CT, MRI, functional MRI, SPECT and PET, as well as other methods known to those of ordinary skill in the art.

Therapeutic benefit can also be correlated with one or more surrogate end points. By way of example, not limitation, production of certain proteins or other factors by metastatic colorectal cancers, such as progastrin or carcinoembryonic antigen (CEA), can be measured in a subject over time with a reduction in levels of the factor being indicative of therapeutic benefit.

With respect to preventing colorectal cancer metastasis, an effective dosage is one that is effective to at least partially prevent metastatic colorectal cancer, as evidenced by, among other things, absence of colorectal cancer metastases, delaying, halting or slowing the growth of colorectal cancer metastases, reducing the number and/or size of any colorectal metastases that ultimately might occur, and inhibition of or interference with any of the mechanistic steps by which metastatic colorectal cancer cells are able to spread from the primary tumor. Complete prevention of colorectal cancer metastasis, while desirable, is not required for efficacy to exist.

With respect to preventing colorectal cancer recurrence, an effective dosage is one that is effective to at least partially prevent recurrence of colorectal cancer, as evidenced by, among other things, absence of colorectal cancer recurrence, maintaining remission of colorectal cancer, or delaying, halting or slowing the reappearance or regrowth of colorectal cancer, or growth of a new colorectal tumor, in a subject after treatment where the initial colorectal cancer became undetectable or apparently disappeared. Efficacy for preventing recurrence of colorectal cancer is also evidenced by, among other things, the killing of colorectal cancer stem cells, delaying, halting, inhibiting or slowing the growth or proliferation of colorectal cancer stem cells, increasing colorectal cancer stem cell apoptosis, or causing the differentiation of colorectal cancer stem cells into cells not capable of contributing to the formation or growth of colorectal cancer. As described elsewhere herein, colorectal cancer stem cells are identifiable as having one or more phenotypic attributes characteristic of such cells including, but not limited to, expression of certain cell markers, ability to grow as spheroids under low adherence culture conditions and the ability to initiate new tumor growth after transplantation. Complete prevention of recurrence of colorectal cancer, while desirable, is not required for efficacy to exist.

Binding all progastrin is not necessarily required to achieve therapeutic efficacy. Rather, reducing the concentration of progastrin within a tumor, systemically, in particular body fluids, such as ascites fluid, fluid from pleural effusions, cerebrospinal fluid, lymph, blood, plasma, serum, or elsewhere, may also be effective.

In accordance with the knowledge of those ordinarily skilled in the art, the dose of an anti-hPG antibody composition can be titrated in a patient so as to reduce the free hPG concentration in a tissue or body fluid of interest at a predetermined time after administration at least about 10%, 20%, 30%, 40%, 50%, 60%, 70%, 80%, 90, or 100%, or about 5%-10%, about 10%-15%, about 15%-20%, about 20%-25%, about 25%-30%, about 30%-35%, about 35%-40%, about 40%-45%, about 45%-50%, about 50%-55%, about 55%-60%, about 60%-65%, about 65%-70%, about 70%-75%, about 75%-80%, about 80%-85%, about 85%-90%, or about 90%-95%, or a percentage reduction in free hPG concentration ranging between any of the foregoing values.

The amount of anti-hPG antibody administered will depend on a variety of factors, including the size and weight of the subject to be treated, the form, route and site of administration, the therapeutic regimen (e.g., whether a second therapeutic agent is used), the age and condition of the particular subject being treated, the level of PG detected in the blood of said subject prior to treatment, the sensitivity of the subject being treated with anti-PG antibodies. The appropriate dosage can be readily determined by a person skilled in the art. Ultimately, a clinician will determine appropriate dosages to be used. This dosage can be repeated as often as appropriate. If side effects develop the amount and/or frequency of the dosage can be altered or reduced, in accordance with normal clinical practice. The proper dosage and treatment regimen can be established by monitoring the progress of therapy using the methods of the present disclosure or other methods known to those of ordinary skill in the art.

Effective dosages can be estimated initially from in vitro assays. For example, an initial dose for use in animals may be formulated to achieve a circulating blood or serum concentration of anti-hPG antibody that is at or above the binding affinity of the antibody for progastrin as measured in vitro. Calculating dosages to achieve such circulating blood or serum concentrations taking into account the bioavailability of the particular antibody is well within the capabilities of skilled artisans. For guidance, the reader is referred to Part 1: General Principles in "*Goodman and Gilman's The Pharma-* cological Basis of Therapeutics," 11th Ed., Hardman, J. G., et al., Eds., McGraw-Hill Professional, and the references cited therein. Initial dosages can also be estimated from in vivo data, such as animal models. Ordinarily skilled artisans can routinely adapt such information to determine dosages suitable for human administration.

In specific embodiments, an i.v. dose may be determined for an individual subject by measuring the serum or plasma PG concentration of the individual a few times a few days to a few weeks prior to treatment and calculating an amount of anti-PG antibody that would be saturating, i.e., an amount that would be sufficient to bind all of the PG. As will be appreciated by skilled artisans, the amount of any specific antibody necessary to achieve saturation for a given serum or plasma concentration of PG will depend, in part, on the affinity constant of the particular antibody. Methods for calculating saturating quantities for specific anti-PG antibodies of interest are well-known.

To insure saturation, an amount that is greater than the calculated saturating amount may be administered, for example, at least 2-, 3-, 4-, 5-, 6-, 7-, 8-, 9- or even 10-fold greater than the calculated saturating amount may be administered. For modes of administration other than i.v., the amount can be adjusted based upon pharmacokinetic and bioavailability, as is well known in the art.

The effective dose of an anti-hPG antibody composition can range from about 0.001 mg/kg to about 250 mg/kg per single (e.g., bolus) administration, multiple administrations or continuous (e.g., infusion) administration, or any effective range or value therein depending on the type of cancer the recurrence of which is sought to be prevented, the route of administration and the age, weight and condition of the subject. In certain embodiments, each dose can range from about 0.1 mg/kg to about 0.5 mg/kg; about 0.25 mg/kg to about 0.75 mg/kg; about 0.5 mg/kg to about 1 mg/kg; about 2 mg/kg; about 1.5 mg/kg to about 2.5 mg/kg; about 2 mg/kg to about 3 mg/kg; about 2.5 mg/kg to about 3.5 mg/kg; about 3 mg/kg to about 4 mg/kg; about 3.5 mg/kg to about 4.5 mg/kg; about 4 mg/kg to about 5 mg/kg; about 5 mg/kg to about 7 mg/kg; about 6 mg/kg to about 8 mg/kg; about 7 mg/kg to about 9 mg/kg; about 8 mg/kg to about 10 mg/kg; about 10 mg/kg to about 15 mg/kg; about 12.5 mg/kg to about 17.5 mg/kg; about 15 mg/kg to about 20 mg/kg; about 17.5 mg/kg to about 22.5 mg/kg; about 20 mg/kg to about 25 mg/kg; about 22.5 mg/kg to about 27.5 mg/kg; about 25 mg/kg to about 30 mg/kg; about 30 mg/kg to about 40 mg/kg; about 35 mg/kg to about 45 mg/kg; about 40 mg/kg to about 50 mg/kg; about 45 mg/kg to about 55 mg/kg; about 50 mg/kg to about 60 mg/kg; about 55 mg/kg to about 65 mg/kg; about 60 mg/kg to about 70 mg/kg; about 65 mg/kg to about 75 mg/kg; about 70 mg/kg to about 80 mg/kg; about 75 mg/kg to about 85 mg/kg; about 80 mg/kg to about 90 mg/kg; about 85 mg/kg to about 95 mg/kg; about 90 mg/kg to about 100 mg/kg; about 95 mg/kg to about 105 mg/kg; about 100 mg/kg to about 150 mg/kg; about 125 mg/kg to about 175 mg/kg; about 150 mg/kg to about 200 mg/kg; about 175 mg/kg to about 225 mg/kg; about 200 mg/kg to about 250 mg/kg. Other dosage ranges are also possible.

Amount, frequency, and duration of administration will depend on a variety of factors, such as the patient's age, weight, and disease condition. Thus, in non-limiting examples, a therapeutic regimen for administration can continue for 1 day or more, 2 days or more, 3 days or more, 4 days or more, 5 days or more, 6 days or more, 1 week or more, 2 weeks to indefinitely, for 2 weeks to 6 months, from 3 months to 5 years, from 6 months to 1 or 2 years, from 8 months to 18 months, or the like. Optionally, the therapeutic regimen provides for repeated administration, e.g., once daily, twice daily, every two days, three days, five days, one week, two weeks, or one month. The repeated administration can be at the same dose or at a different dose. The administration can be repeated once, twice, three times, four times, five times, six times, seven times, eight times, nine times, ten times, or more. A therapeutically effective amount of anti-hPG antibody can be administered as a single dose or over the course of a therapeutic regimen, e.g., over the course of a week, two weeks, three weeks, one month, three months, six months, one year, or longer.

8. EXAMPLES

Example 1

Expression of Gastrin Gene in Metastatic Colorectal Cancer Cells

This example describes the expression of the gastrin (GAST) gene in the human primary colorectal cancer cell lines HT29, HCT116, RKO, SW480, and DLD1, and the metastatic colorectal cancer cell lines SW620 and T84. Cells isolated from a biopsy sample from a human primary colorectal tumor were also tested (CRC1). SW620 cells were originally derived from a lymph node metastasis of a patient diagnosed with Dukes' Stage C colorectal adenocarcinoma. T84 cells were originally derived from a lung metastasis of a patient diagnosed with colorectal carcinoma.

A. Methods

Using standard techniques, expression of the GAST mRNA was quantified using quantitative RT-PCR from RNA preparations of HT29, HCT116, RKO, SW480, DLD1, SW620 and T84 cell lines. Data is expressed in comparison with the gastrin mRNA expression level found in the RKO primary colorectal cancer cell line. RKO cells normally express low levels of progastrin. Note that relative gastrin mRNA levels are reported on a logarithmic scale.

B. Results

The gastrin gene expression levels measured by quantitative RT-PCR are shown in FIG. 1. All primary and metastatic colorectal cancer cells examined expressed the gastrin gene, but at variable levels. Through post-translational processing, the gastrin gene product may be converted into progastrin.

A similar experiment was performed using the metastatic colorectal cancer cell line Colo-205, but the results were not repeatable.

Example 2

Expression of Gastrin Gene in Primary and Metastatic Colorectal Tumors Surgically Removed from Patients This example describes the expression of the gastrin (GAST) gene in matched primary and metastatic colorectal tumors surgically removed from patients.

A. Methods

Primary and metastatic colorectal tumors were surgically resected from patients in accordance with applicable ethical guidelines. Using standard techniques, RNA was prepared from tumor tissue samples and gastrin mRNA was measured by quantitative RT-PCR. Expression of gastrin mRNA in the metastatic tumor was normalized relative to the level of expression in the matched primary tumor taken from the same patient.

B. Results

Levels of gastrin mRNA expressed in metastatic colorectal tumors from 11 patients relative to expression in matched primary tumors from the same patients is shown in FIG. 2. Although all primary and metastatic colorectal tumors studied expressed the gastrin gene, the expression level in metastatic tumors relative to the matched primary tumor varied extensively among the different patients.

Example 3

Secretion of Progastrin by Metastatic Cancer Cells

This example describes quantification of secretion of progastrin by three different metastatic colorectal cancer cells.

A. Methods

Cells were grown in regular plastic 75 cm$^2$ flasks until 60% confluence. Medium was then removed and cells rinsed once with PBS. Twenty ml of M11 medium (without phenol red) was then added to the flasks, and the cells incubated for an additional 48 hours. Medium was then collected, centrifuged at 1,000 g for 5 minutes to remove cell debris, and frozen at −80° C. Cells were then trypsinized and counted.

To measure secreted progastrin, the frozen growth medium was slowly thawed on ice, and then concentrated 40-fold to a volume of 500 µl using protein concentrators (Icon, Pierce) by centrifugation at 2,500 g for 45 minutes. Progastrin concentration was then measured using a sandwich ELISA technique.

B. Results

FIG. 3 shows the concentration of progastrin in medium conditioned by three metastatic colorectal cancer cell lines. Data is expressed as progastrin concentration of in pM per million cells per 48 hours of growth. In this experiment, the Colo-205 cells did not produce PG within the limits of detection of the assay used.

Example 4

Plasma or Serum Progastrin Concentrations in Patients Diagnosed with Primary and Metastatic Colorectal Cancer This example describes quantification of plasma or serum levels of progastrin in patients with primary colorectal cancer and no metastases, patients with metastatic colorectal cancer and patients with metastatic colorectal cancer from whom the primary tumor was surgically removed C. Methods Plasma or serum progastrin concentrations were measured in healthy individuals, as a control, and in patients with colorectal cancer. Healthy control samples (n=104) were obtained from a blood bank. Colorectal cancer patients comprised three groups. First, patients diagnosed at the time of sampling with primary cancer without metastases (T+M−; n=16). Second, patients diagnosed at the time of sampling with metastatic disease (T+M+; n=24). And, third, patients whom at the time of sampling were diagnosed with metastatic disease but from whom the primary tumor had been removed surgically (T−M+; n=46). A majority of patients with metastatic disease, i.e., 15 of 24 T+M+ patients, and 41 of 46 T−M+ patients, were undergoing or had just undergone chemotherapy at the time of sampling.

Quantification of plasma or serum progastrin levels was performed using a progastrin-specific sandwich ELISA technique similar to the one described prophetically below.

The wells of Nunc MaxiSORP 96-well plates are coated with a first progastrin-specific antibody as follows. Anti-progastrin polyclonal antibodies specific for the carboxy-terminal region of progastrin are diluted to a concentration of 3 µg/ml in a solution of 50 mM, pH 9.6 sodium carbonate/bicarbonate buffer in MilliQ water. A total of 100 µl of the antibody solution is then added to each well of the 96-well plates, and incubated overnight at 4° C. After binding, the antibody solution is removed from the wells, which are then washed three times with 100 µl wash buffer (1×PBS/0.1% Tween-20). A total of 100 µl blocking buffer (1×PBS/0.1% Tween-20/0.1% BSA) is then added to each well and incubated for 2 hours at 22° C. Blocking buffer is then removed and the wells washed three times with wash buffer. Plasma or serum samples isolated from patients is then added to the wells in a volume of 100 µl in a dilution series, typically 1:1, 1:2, 1:5 and 1:10 dilutions, and is then incubated for 2 hours at 22° C. Plasma or serum samples are analyzed in duplicate.

Assays also include two standard curves. The first standard curve is prepared using dilutions of recombinant progastrin to a final amount of 1 ng, 0.5 ng, 0.25 ng, 0.1 ng, 0.05 ng, 0.01 ng, and 0 ng per well. The second standard curve, which serves as a negative control, is prepared from progastrin-negative human serum diluted in blocking buffer at the same dilutions as the test samples, i.e., 1:1, 1:2, 1:5 and 1:10. Alternatively, when plasma samples are being assayed, the second standard curve, which serves as a negative control, is prepared from progastrin-negative human plasma diluted in blocking buffer at the same dilutions as the test samples, i.e., 1:1, 1:2, 1:5 and 1:10.

After incubation with the plasma or serum samples is complete, the well contents are removed and the wells are washed three times with wash buffer, 100 µl/well, after which progastrin bound to the first antibody is detected using a second antibody specific for progastrin, as follows.

Biotin-coupled anti-progastrin polyclonal or monoclonal antibodies specific for the amino-terminal region of progastrin are diluted in blocking buffer to a concentration of 0.1 to 10 µg/ml, depending on the antibody. A total of 100 µl of the antibody solution is then added to each well, and incubated for 1 hour at 22° C.

After secondary antibody binding is complete, the plates are washed three times with wash buffer, 100 µl/well, after which 100 µl of a solution of streptavidin-HRP (25 ng/ml in blocking buffer) is added to each well and incubated for 1 hour at 22° C. After incubation with the streptavidin-HRP solution is complete, the plates are washed three times with wash buffer, 100 µl/well. Thereafter, 100 µl of chemiluminescent substrate prepared using a Pierce SuperSignal ELISA Femto Maximum Sensitivity Chemiluminescent Substrate kit, is added per well, incubated for 5 min at room temperature in the dark, and then read on a luminometer.

Based on the luminometer readings, linear regression analysis is used to derive the equation of the lines corresponding to the standard curve data. Using this equation, the concentration of progastrin in the various patient samples is then calculated.

D. Results

The box plots of FIG. 4 show the 25$^{th}$ percentile, median, and 75$^{th}$ percentile plasma of serum progastrin concentrations in the three groups of colorectal cancer patients assayed, compared to healthy controls. The whiskers indicate the 5th and 95th percentiles of plasma or serum progastrin concentrations. T+ or T− indicate that the primary tumor is still in place or has been resected, respectively; M+ or M− indicate that metastases were, or were not detected in patients, respectively. Table 4 contains a summary of the statistical analysis of the raw data.

This data demonstrates that patients with both primary and metastatic colorectal cancer had elevated levels of progastrin in their plasma or serum compared to healthy individuals. In addition, progastrin levels remain elevated in patients with metastatic colorectal cancer from whom the primary tumor was surgically removed. This suggests that colorectal metastases produce progastrin in such patients.

TABLE 4

| Table Analyzed Kruskal-Wallis test | PG in CRC patients | | |
|---|---|---|---|
| P value | <0.0001 | | |
| Exact or approximate P value? | Gaussian Approximation | | |
| P value summary | *** | | |
| Do the medians vary signif. (P < 0.05) | Yes | | |
| Number of groups | 4 | | |
| Kruskal-Wallis statistic | 33.86 | | |
| Dunn's Multiple Comparison Test | Difference in rank sum | Significant? P < 0.05? | Summary |
| T+M− patients vs Controls (blood bank) | 51.45 | Yes | *** |
| T+M+ patients vs Controls (blood bank) | 50.41 | Yes | *** |
| T−M+ patients vs Controls (blood bank) | 37.42 | Yes | *** |

Example 5

Effect of Anti-Progastrin Polyclonal Antibodies on Growth of SW620 Metastatic Colorectal Cancer Cells in Culture This example describes the effect of anti-hPG polyclonal antibodies on the growth of the SW620 human metastatic colorectal cancer cell line in culture.

A. Methods

SW620 cells were seeded into 6-well plates, serum-starved overnight, then treated in every 12 hours with PBS, 3 microgram/ml control antibody (polyclonal rabbit anti-human IgG, Affinity BioReagents, Ref #SA1-600) or anti-PG polyclonal antibodies. The experiment was carried out in duplicate, and the technician was blinded as to the contents of the treatment solutions. Seventy-two hours after the start of the treatments the number of surviving cells in each well were counted three times.

B. Results

As shown in FIG. 5, treatment with anti-PG polyclonal antibodies caused a 43.5% decrease in growth of SW620 cells over a 72 hour period (p=0.0294, Mann Whitney test; n=2). The results of this experiment demonstrate that the polyclonal antibodies against PG are effective to reduce the growth of metastatic colorectal cancer cells in vitro.

Example 6

Effect of Anti-Progastrin Monoclonal Antibodies on Growth of SW620 Metastatic Colorectal Cancer Cells in Culture This example describes the effect of anti-hPG monoclonal antibodies on the growth of the SW620 human metastatic colorectal cancer cell line in culture.

A. Methods

SW620 cells were seeded into 6-well plates, serum-starved overnight, then treated every 12 hours with PBS, 3 microgram/ml control antibody (Mouse anti-human IgG1, Calbiochem, Ref #411451) or four different anti-PG monoclonal antibodies, MAb3, MAb4, MAb2, and MAb1. The experiment was carried out in duplicate, and the technician was blinded as to the contents of the treatment solutions. Forty-eight hours after the start of the treatments the number of surviving cells in each well were counted six times and averaged.

In a separate experiment, SW620 cells were seeded into 6-well plates (100,000 cells per well) and treated similarly above with 5 µg/ml of anti-hPG monoclonal antibodies 5-23 (i.e., MAb5-MAb23) or 5 µg/ml control antibody. After 48 hours the number of viable cells were counted from which the number of cells at the beginning of the experiment (i.e., T0) were subtracted. The number of surviving cells in the specific antibody treated wells was then expressed as a percentage of the control.

B. Results

The results, shown in FIG. 6A, of treating SW620 cells with MAb1-MAb4 were calculated as the average number of cells per well at the end of the experiment minus the number of cells seeded at the beginning of the experiment. The raw numbers and statistics (Mann Whitney Test) are shown in Table 5. The results of this experiment demonstrate that different monoclonal antibodies against PG are effective to reduce the growth of SW620 metastatic colorectal cancer cells in vitro, compared to a control antibody. The results also show that while all the monoclonal antibodies against PG were effective to reduce growth of the cells compared to the control antibody, two of the antibodies, MAb3 and MAb4, were more effective than the others.

TABLE 5

| Antibody Treatment | Cell numbers | p-value (treated vs CTMab) |
|---|---|---|
| CT antibody-T0 | 158556 | |
| MAb3-T0 | 50056 | 0.0009 |
| MAb4-T0 | 52984 | 0.0014 |
| MAb2-T0 | 115056 | 0.0156 |
| MAb1-T0 | 108056 | 0.0009 |

The results of treating SW620 cells with MAb5-MAb23, each of which are capable of specifically binding hPG, are shown in FIG. 6B. As the results demonstrate, compared to a non-specific control antibody, the anti-hPG monoclonal antibodies tested exhibit a range of effectiveness for inhibiting the growth of the SW620 metastatic colorectal cancer cell line in culture.

A related experiment to determine the effect on growth of treating Colo-205 metastatic colorectal cancer cells with MAb3 was performed, but the results were not repeatable.

Example 7

Effect of Anti-Progastrin Monoclonal Antibodies on Growth of T84 Metastatic Colorectal Cancer Cells in Culture This example describes the effect of anti-hPG monoclonal antibodies on the growth of the T84 human metastatic colorectal cancer cell line in culture.

A. Methods

The methods employed for this experiment were similar to those used to measure the effect of anti-progastrin monoclonal antibodies on SW620 cells, except that the anti-progastrin antibody used was anti-hPG MAb3.

B. Results

The results, shown in FIG. 7, were calculated as the average number of cells per well at the end of the experiment minus the number of cells seeded at the beginning of the experiment. A summary of the statistical analysis is shown in Table 6. The results of this experiment demonstrate that the anti-hPG MAb3 is effective to reduce the growth of T84 metastatic colorectal cancer cells in vitro, compared to a control antibody.

TABLE 6

| Table Analyzed | T84 cells |
| Column E | CT MAb-T0 |
| vs | vs |
| Column F | Anti-hPG MAb3-T0 |
| Mann Whitney test | |
| | |
| P value | 0.0370 |
| Exact or approximate P value? | Gaussian Approximation |
| P value summary | * |
| Are medians signif. different? (P < 0.05) | Yes |
| One-or two-tailed P value? | Two-tailed |
| Sum of ranks in column E, F | 52.50, 25.50 |
| Mann-Whitney U | 4.500 |

A related experiment to determine the effect on growth of treating Colo-205 metastatic colorectal cancer cells with MAb3 was performed, but the results were not repeatable.

Example 8

Effect of Anti-Progastrin Polyclonal Antibodies on Formation in Nude Mice of Hepatic Metastases by SW620 Cell Xenografts This example describes the effect of anti-PG polyclonal antibodies on the ability of SW620 cells to form liver metastases after transplantation into nude mice.

A. Methods

A total of $5 \times 10^6$ SW620 cells were injected into the spleen of each of 31 BALBc/nude mice at age 6 weeks old. Two minutes after injection of the cells, the spleens were surgically removed. After four days of recovery, mice were randomly divided into three groups, each of which was subjected to one of three different treatments. Specifically, eleven mice were injected with PBS, ten were injected with a control antibody diluted in PBS, and ten mice were injected with anti-PG polyclonal antibodies, also diluted in PBS. The dose of antibodies was 8 mg/kg in a volume of 150 microliters. Injections were made intraperitoneally twice per week for six weeks. Six weeks later, after the course of injections was finished, the mice were euthanized with carbon dioxide and the livers were removed and the number of visible metastases present was counted. Livers and metastases were also prepared for paraffin embedding and immunohistochemistry analysis.

B. Results

A photograph of liver without visible metastases from a mouse treated with anti-hPG polyclonal antibodies is shown in FIG. 8A. Photographs of livers with visible metastases from mice treated with a control polyclonal antibody are shown in FIG. 8B. Table 7 shows the number of metastases counted in each liver from mice treated with anti-hPG polyclonal antibodies. Table 8 shows the number of metastases counted in each liver from mice treated with control polyclonal antibody. Table 9 shows the number of metastases counted in each liver from mice treated with PBS. FIG. 9 is a graphical representation of the number of metastases versus treatment arms.

TABLE 7

| Mouse | Weight (g) | No. Liver Met |
|---|---|---|
| 0 | 20.1 | 0 |
| 1 | 17.7 | 2 |
| 2 | 17.3 | 0 |
| 3 | 21.2 | 0 |
| 4 | 19.9 | 0 |
| 5 | 19.9 | 3 |
| 6 | 17.0 | 0 |
| 7 | 18.1 | 0 |
| 8 | 16.7 | 2 |
| 9 | 16.6 | 1 |

TABLE 8

| Mouse | Weight (g) | No. Liver Met |
|---|---|---|
| 10 | 17.0 | 0 |
| 11 | 18.0 | 2 |
| 12 | 19.9 | 1 |
| 13 | 17.2 | 0 |
| 14 | 18.2 | 1 |
| 15 | 17.8 | 3 |
| 16 | 17.9 | 10 |
| 17 | 17.9 | 0 |
| 18 | 17.0 | 1 |
| 19 | 16.0 | 1 |

TABLE 9

| Mouse | Weight (g) | No. Liver Met |
|---|---|---|
| 20 | 20.1 | 7 |
| 21 | 19.3 | 0 |
| 22 | 19.2 | 0 |
| 23 | 18.7 | 1 |
| 24 | 18.8 | 1 |
| 25 | 16.5 | 0 |
| 26 | 19.3 | 0 |
| 27 | 19.1 | 1 |
| 28 | 18.0 | 0 |
| 29 | 18.8 | 5 |
| 30 | 17.8 | 3 |

Histological analysis revealed the presence of micrometastases in liver sections from both control groups, which were not present in sections obtained form the livers of animals treated with anti-hPG antibodies. An example of a micrometastasis detected in a blood vessel within the liver of a control animal is shown in the photomicrograph depicted in FIG. 10.

The results in this example demonstrates that treatment with anti-hPG antibodies of nude mice transplanted with SW620 cells, a colorectal cancer metastatic cell line, reduced the total number of visible liver metastases compared to mice that received control antibody or vehicle alone. Although the extent of the reduction did not reach statistical significance, the trend in the numerical data, as well as the absence of micrometastases in the liver of anti-hPG antibody treated mice, suggests that PG antibodies are effective at reducing the incidence of metastasis of colorectal cancer in this model system.

Example 9

Effect of Anti-Progastrin Monoclonal Antibodies on Formation in Nude Mice of Hepatic Metastases by SW620 Cell Xenografts This example describes the effect of anti-PG monoclonal antibodies on the ability of SW620 cells to form liver metastases after transplantation into nude mice.

A. Methods

A total of $5\times10^6$ SW620 cells were injected into the spleen of each of 20 BALBc/nude mice at age 5 weeks old. Two minutes after injection of the cells, the spleens were surgically removed. After recovery, mice were randomly divided into two groups, each of which was subjected to one of two different treatments. Specifically, 10 mice were injected with a control antibody (anti-human IgG1Fc) diluted in PBS, and 10 mice were injected with anti-hPG monoclonal antibody MAb3, also diluted in PBS. The dose of antibodies was 8 mg/kg in a volume of 150 microliters. Injections were made intraperitoneally twice per week for six weeks. Once per week each mouse was weighed. Six weeks later, after the course of injections was finished, the mice were euthanized with carbon dioxide and the livers were removed and the number of visible metastases present was counted.

B. Results

The results are shown in FIG. 11. The mean number of metastases was 7.3 in mice administered control antibody and 4.3 in mice treated with anti-hPG monoclonal antibody MAb3. This corresponds to a decrease of 41%, and is statistically significant at a p=0.0372. The statistical analysis is shown in Table 10, below. The mean weight of liver metastases in the treated mice also decreased to 96 mg, compared to 167 mg in the control mice, although this difference was not calculated to be reach statistical significance.

TABLE 10

| Table Analyzed | Number of Metastases |
| --- | --- |
| Column A | CtrlMab |
| vs | vs |
| Column B | MAb3 |
| Mann Whitney test | |
| | |
| P value | 0.0372 |
| Exact or approximate P value? | Gaussian Approximation |
| P value summary | * |
| Are medians signif. different? (P < 0.05) | Yes |
| One-or two-tailed P value? | One-tailed |
| Sum of ranks in column A, B | 129, 81 |
| Mann-Whitney U | 26.00 |

Example 10

Expression of LGR5 in Colorectal Cancer Cells is Increased by Growth Under Low Adherence Culture Conditions This example describes the effect on expression of the colon stem cell surface marker LGR5 on colorectal cancer cell lines of growth under low adherence culture conditions. Cells tested included cells from primary colorectal cancer and metastatic colorectal cancer cell lines, cells from a biopsy sample obtained from human primary colorectal cancer. Low adherence culture conditions can enrich for the growth of cancer stem cells as spheroids and provide a useful assay tool for colorectal cancer stem cells.

A. Methods

Cells tested were from the primary colorectal cancer cell lines HT29 and HCT116, and the metastatic colorectal cancer cell lines SW620 and T84.

Cells isolated from a biopsy sample from a human primary colorectal tumor were also tested (CRC1) as follows. Biopsy samples were rinsed several times in sterile Hanks Balanced Salts (HBSS), then placed for 30 min at room temperature in a 0.4% sodium hypochlorite solution in HBSS. After several further rinses in HBSS, biopsies were cut into 1 mm pieces using scalpel blades and rinsed. Pieces were then incubated for 1 h at 37° C. in a 50% Accumax solution in M11 medium containing strong antibiotics and glucose (DMEM/F12 with 20 ng/ml EGF, 10 ng/ml FGF, 20 µg/ml insulin, N2 supplement, 2 µg/ml cyproflaxin, 5 µg/ml gentamycin and 3 µg/ml glucose), with gentle shaking once every 20 min. The Accumax solution containing these digested samples was then filtered on 100 micrometer sieves. Viability was determined on a small aliquot of the filtered solution using the Trypan blue technique. The solution was then centrifuged at 200 g for 10 min and the pellet was resuspended in 2 ml M11 medium containing 10% FBS in order to stop the Accumax reaction. Cells were then incubated in Corning ultra low adherence flasks for several days then transferred into M11 medium without FBS for further amplification. Cells from the CRC1 sample were amplified for several weeks and frozen/thawed once before the experiment was performed.

Cells were grown under two different culture conditions. First, cells were grown in standard plastic cultureware for growth of mammalian cells, which promotes cellular attachment to the surface. Specifically, 200,000 cells were seeded into 75 cm² flasks (Corning) in DMEM+5% Fetal Bovine Serum (FBS)+100 U/ml penicillin+100 U/ml streptomycin.

Second, cells were grown in low adherence cultureware to which mammalian cells typically attach poorly or not at all. Specifically, 30,000 cells were grown in ultra low adherent 75 cm² flasks (Corning) in M11 medium (DMEM/F12 with 20 ng/ml EGF, 10 ng/ml FGF, 20 µg/ml insulin, N2 supplement, 2 µg/ml cyproflaxin, 5 µg/ml gentamycin and 3 µg/ml glucose). After a period of growth, cells were resuspended and disaggregated into a single cell suspension using Accumax (Innovative Cell Technologies, Inc.) for 45 minutes at 37° C. prior to FACS analysis. Using standard techniques, cells were thereafter stained with an antibody to the N-terminal region of the cell surface marker LGR5 (Abgent, Inc.), and sorted by FACS to determine the percentage of cells expressing the marker. All experiments were performed three times.

B. Results

The relative percentages of LGR5 expressing colorectal cancer cells resulting from growth of the cells under the two culture conditions are shown in FIG. 12. For all the cell lines tested, the percentage of LGR5 expressing cells was greater when the cells were grown as spheroids under low adherence culture conditions (black bars) compared to growth under conventional conditions (gray bars). The pattern was similar for cells derived from primary colorectal cancer cell lines (HT29 and HCT116), as well as metastatic colorectal cancer cell lines (SW620 and T84).

CRC1 cells, obtained from a biopsy of human primary colorectal cancer, also expressed LGR5 when grown under low adherence culture conditions. Because in this particular experiment the CRC1 cells did not grow well under conventional adherent conditions, however, it was not possible to directly compare the level of LGR5 expression when the cells were grown under adherent versus non-adherent conditions.

Example 11

Expression of the Gastrin Gene is Increased by Growth of Colorectal Cancer Cells Under Low Adherence Culture Conditions This example describes the effect on the expression of the gastrin gene in primary and metastatic colorectal cancer cell lines, as well as cells from a biopsy sample obtained from human primary colorectal cancer, grown under low adherence culture conditions. Such growth conditions enrich for cancer stem cells.

A. Methods

Cells tested were from the primary colorectal cancer cell lines HT29, HCT116, RKO, SW480, and DLD1, and the metastatic colorectal cancer cell lines SW620 and T84. Cells isolated from a biopsy sample from a human primary colorectal tumor were also tested (CRC1). Cells were grown under two different culture conditions. First, cells were grown in conventional cultureware for growth of mammalian cells, which promotes cellular attachment to the plastic surface, as described above. Second, cells were also grown in low adherence cultureware to which mammalian cells typically poorly attach, as described above. After a period of growth, cells were resuspended and lysed, and mRNA isolated using standard techniques. Expression of the gastrin gene was then measured using quantitative RT-PCR according to standard techniques. Each experiment was repeated three times.

B. Results

The relative levels of gastrin mRNA expressed in the different cells tested under conventional and low adherence culture conditions is reported in FIG. 13. Levels were normalized relative to the amount of gastrin mRNA expressed in the RKO primary colorectal cancer cell line. RKO cells normally express low levels of progastrin. Note that relative gastrin mRNA levels are reported on a logarithmic scale. For all the cell lines tested, except the RKO cells, gastrin gene expression was higher, sometimes many fold higher, when the cells were grown under low adherence culture conditions (black bars) compared to growth under conventional conditions (gray bars). The pattern was similar for cells derived from primary colorectal cancer cell lines, as well as metastatic colorectal cancer cell lines.

Example 12

Colorectal Cancer Cells Grown in Low Adherence Culture Conditions Express Progastrin Protein This example describes the expression of progastrin protein by primary and metastatic colorectal cancer cell lines, as well as cells from a biopsy sample obtained from human primary colorectal cancer, grown under low adherence culture conditions. Such growth conditions enrich for cancer stem cells.

A. Methods

Cells tested were from the primary colorectal cancer cell line HT29, and the metastatic colorectal cancer cell lines SW620 and T84. Cells isolated from a biopsy sample from a human primary colorectal tumor were also tested (CRC1). Cells were grown in low adherence cultureware in M11 medium (without phenol red). After 48 hours, the medium was collected, centrifuged at 1,000 g for 5 minutes to remove cell debris, and frozen at −80° C. Cells were disaggregated using Accumax and counted. To measure secreted progastrin, the frozen medium was thawed on ice, and then concentrated 40-fold to a volume of 500 µl by centrifugation at 2,500 g for 45 minutes using protein concentrators (Icon, Pierce). Progastrin concentration was then measured using a sandwich ELISA technique. Each experiment was repeated twice.

B. Results

The concentration of progastrin secreted into the growth medium by colorectal cancer cells after 48 hours of growth under low adherence culture conditions is shown in FIG. 14. All the cells tested, including one primary colorectal cancer cell line, two metastatic colorectal cancer cell lines, and cells from a biopsy sample obtained from human primary colorectal cancer secreted progastrin when grown as spheroids in low adherence culture conditions. However, the SW620 cells secreted substantially less progastrin than the other cell lines under study. Data is expressed as progastrin concentration in pM per million cells per 48 hours of growth.

Example 13

Effect of Anti-Progastrin Polyclonal Antibodies on Growth of Primary Colorectal Cancer Cells as Spheroids Under Low Adherence Culture Conditions This example describes the effect of anti-progastrin polyclonal antibodies on the growth as spheroids of primary colorectal cancer cell lines, as well as cells from a biopsy sample obtained from human primary colorectal cancer, grown under low adherence culture conditions. Such growth conditions enrich for cancer stem cells.

A. Methods

Cells tested were from the primary colorectal cancer cell lines HT29 and HCT116, as well as cells isolated from a biopsy sample from a human primary colorectal tumor (CRC1). Cells were seeded into wells of low adherence 96-well plates (Corning) in M11 medium (DMEM/F12 with 20 ng/ml EGF, 10 ng/ml FGF, 20 µg/ml insulin, N2 supplement, 2 µg/ml cyproflaxin, 5 µg/ml gentamycin and 3 µg/ml glucose). For HT29 and HCT116 cells, a total of 500 cells in 100 µl were added to each of 3 wells per treatment condition, whereas for CRC1 cells, a total of 500 cells in 100 µl were added to each of 10 wells per treatment condition. Every 24 hours, cells were treated with 3 µg/ml of polyclonal anti-progastrin antibodies, or control antibody (Polyclonal Rabbit anti-human IgG, Affinity BioReagents, Ref #SA1-600). After 10 days of treatment for HT29 and HCT116 cells, and 14 days of treatment for CRC1 cells, the number of cell spheroids in each well was counted, and the average per well calculated. The technician performing the experiments was blinded as to the contents of the antibody solutions being tested. Each experiment was repeated twice.

B. Results

As shown in FIG. 15-17, compared to a control antibody, anti-progastrin polyclonal antibodies substantially reduced the number of cell spheroids formed by primary colorectal cancer cells grown under low adherence culture conditions.

Example 14

Effect of Anti-Progastrin Monoclonal Antibodies on Growth of Primary Colorectal Cancer Cells as Spheroids Under Low Adherence Culture Conditions This example describes the effect of anti-progastrin monoclonal antibodies on the growth as spheroids of LGR5 positive cells from two primary colorectal cancer cell lines when such cells were grown under low adherence culture conditions. Such growth conditions enrich for cancer stem cells.

A. Methods

Cells tested were from the primary colorectal cancer cell lines HT29 and HCT116. Cells were first sorted by FACS (FACSaria, BD Biosciences) to isolate those expressing the cancer stem cell marker LGR5. For FACS, $2\times10^6$ HT29 cells were sorted, and $1\times10^6$ HCT116 cells were sorted. Cells were labeled with 2 mg/$1\times10^6$ cells of an antibody specific for the N-terminus of LGR5 (Abgent, Inc., No. AP2745A). After FACS, LGR5 positive cells were plated into 30 wells of low adherence 96 well-plates at a density of 10 cells per well in 100 µl M11 medium (DMEM/F12 with 20 ng/ml EGF, 10 ng/ml FGF, 20 µg/ml insulin, N2 supplement, 2 µg/ml cyproflaxin, 5 µg/ml gentamycin and 3 µg/ml glucose). Every 24 hours for 14 days, cells were treated with 0.3 µg/ml of one of two different anti-progastrin monoclonal antibodies (MAb2 and MAb3), or a control monoclonal antibody (monoclonal mouse anti-human IgG1, Calbiochem, Ref #411451). At the conclusion of treatment, the number of cell spheroids formed in the presence of each antibody type was counted. Cells were then allowed to grow an additional 17 days, during which the medium was refreshed weekly without further antibody treatment. The technician performing the experiments was blinded as to the contents of the antibody solutions being tested.

B. Results

As shown in FIG. 18A and FIG. 19A, respectively, the ability of LGR5 positive cells from two primary colorectal cancer cell lines, HCT116 and HT29, to grow as spheroids over 14 days in low adherence culture was reduced by treatment with two separate monoclonal antibodies against progastrin, compared to a control monoclonal antibody.

Further, as shown in FIG. 18B and FIG. 19B, the number of spheroids did not increase after further incubation of the HCT116 and HT29 cells for 17 days in culture in the absence of exogenously added antibodies. This data means that suppression of sphere formation by the anti-hPG antibodies was continuing even after the specific antibodies were removed.

Example 15

Effect of Anti-Progastrin Monoclonal Antibodies on Growth of Primary Colorectal Cancer Cells as Spheroids Under Low Adherence Culture Conditions This example describes the effect of four different anti-progastrin monoclonal antibodies on the growth as spheroids of CRC1 cells when such cells were grown under low adherence culture conditions. Such growth conditions enrich for cancer stem cells.

A. Methods

CRC1 cells were obtained from a human colon carcinoma biopsy according to standard procedures. After being dissociated in Accumax (Sigma) for 45 minutes at 37° C., cells were plated in low adherence 96 well-plates (Corning) at a density of 100 cells per well in M11 medium (DMEM/F12 with 20 ng/ml EGF, 10 ng/ml FGF, 20 µg/ml insulin, N2 supplement, 2 µg/ml cyproflaxin, 5 µg/ml gentamycin and 3 mg/ml glucose). For each treatment arm, 10 wells were used.

Starting on the first day, cells were treated twice daily with one of four different anti-progastrin monoclonal antibodies, MAb5, MAb8, MAb13 or MAb16 (3 µg/ml) or the same concentration of monoclonal antibody P3X63Ag8 (ATCC, Ref TIB-9) or medium with no antibody added as controls. Thereafter, treatment was performed once daily for 8 days. Spheres were photographed daily for subsequent counting. All experiments were carried out in blinded fashion. After the conclusion of the experiment, the number of spheres from each treatment art was counted.

B. Results

Results are shown in FIG. 20. Each of the anti-hPG monoclonal antibodies tested was effective to reduce the number spheroids formed by the primary colorectal cancer cells in low adherence culture conditions. Compared to a non-specific monoclonal antibody and medium alone, the inhibitory effect for all antibodies tested was statistically significant at $p<0.05$ using the one-way ANOVA with Bonferroni post-hoc test. MAb5, MAb8 and MAb13 all recognize C-terminal epitopes of hPG, whereas MAb16 binds to an N-terminal epitope of hPG.

Example 16

Effect of an Anti-Progastrin Monoclonal Antibody on Growth of Metastatic Colorectal Cancer Cells as Spheroids Under Low Adherence Culture Conditions This example describes the effect of an anti-progastrin monoclonal antibody on the growth as spheroids of ALDH1 positive cells from a metastatic colorectal cancer cell line when such cells were grown under low adherence culture conditions.

A. Methods

Cells tested were from the metastatic colorectal cancer cell line T84. Cells were first sorted by FACS (FACSaria, BD Biosciences) to isolate those expressing the cancer stem cell marker ALDH1 using an ALDEFLUOR kit (Stemcell Technologies). After FACS, ALDH1 positive cells (i.e., those exhibiting detectable ALDH1 enzyme activity) were plated into wells of low adherence 96 well-plates at a density of 100 cells per well in 100 µl M11 medium (DMEM/F12 with 20 ng/ml EGF, 10 ng/ml FGF, 20 µg/ml insulin, N2 supplement, 2 µg/ml cyproflaxin, 5 µg/ml gentamycin and 3 µg/ml glucose). Every 24 hours for 11 days, cells were treated with one of three different concentrations (0.01 µg/ml, 0.1 µg/ml or 1 µg/ml) of an anti-progastrin monoclonal antibody (MAb3), or 1 µg/ml of a control monoclonal antibody (monoclonal mouse anti-human IgG1, Calbiochem, Ref #411451). At the conclusion of treatment, the number of cell spheroids formed in the presence of each antibody was counted. The technician performing the experiments was blinded as to the contents of the antibody solutions being tested.

B. Results

As shown in FIG. 21, the ability of ALDH1 positive cells from the T84 metastatic colorectal cancer cell line to grow as spheroids in low adherence culture was reduced in a dose dependent manner by treatment with a monoclonal antibody against progastrin, compared to a control monoclonal antibody.

Example 17

Effect of Pre-Treatment with Anti-Progastrin Monoclonal Antibodies on Growth of Primary Colorectal Cancer Cells as Spheroids Under Low Adherence Culture Conditions This example describes the effect of pretreatment using four different anti-progastrin monoclonal antibodies on the growth ALDH1 positive CRC1 cells under conventional culture conditions and growth as spheroids of when the cells were transferred to low adherence culture conditions.

A. Methods

CRC1 cells were obtained from a human colon carcinoma biopsy according to standard procedures. After being dissociated in Accumax (Sigma) for 45 minutes at 37° C., CRC1 cells (100,000 cells/well) were grown under conventional adherent culture conditions in serum free DMEM medium for 72 hours in the presence or absence of anti-hPG monoclonal antibodies MAb5, MAb8, MAb13 or MAb16. Experiments were carried out in blinded fashion.

At the end of the treatment period, two different assays were performed on the cells. First, the percentage of cells expressing ALDH1, a marker of colorectal cancer stem cells, was determined by FACS. In the second assay, for each treatment group, 200 cells/well were plated in six wells of a low adherence 24-well plate in 500 µl of serum-free M11 medium supplemented with bFGF and EGF, and grown for 7 days without further treatment. At the end of this period, photographs were taken and the number of spheres per well was counted, and sphere surface area measured.

B. Results

Results are shown in FIG. 22 and FIG. 23. Each of the four anti-hPG monoclonal antibodies tested was effective after three days in conventional adherent culture to reduce the number CRC1 primary colorectal cancer cells expressing ALDH1 compared to a control. Each of these antibodies was also effective to reduce the number of spheroids formed by the primary colorectal cancer cells in low adherence culture conditions after the antibodies were removed and the cells grown for an additional 7 days. Compared to control, the inhibitory effect of MAb5, MAb8 and MAb16 was statistically significant at $p<0.05$ using the one-way ANOVA with Bonferroni post-hoc test. Although MAb13 also reduced the number of spheroids compared to control, the effect did not reach statistical significance.

Example 18

Effect of Pre-Treatment with an Anti-Progastrin Monoclonal Antibody on Growth of Metastatic Colorectal Cancer Cells as Spheroids Under Low Adherence Culture Conditions This example describes the effect of pretreatment using an anti-progastrin monoclonal antibody on the growth as spheroids of ALDH1 positive cells from two metastatic colorectal cancer cell line when such cells were grown under low adherence culture conditions.

A. Methods

Cells tested were from the metastatic colorectal cancer cell lines T84 and SW620. Cells were first grown in conventional adherent cultureware for 72 hours in the presence of the anti-progastrin monoclonal antibody MAb3 (1 µg/ml), a control monoclonal antibody, the chemotherapeutic agent 5-fluorouracil (5FU 10 µM), or the solvent dimethylsulfoxide (DMSO). After treatment, cells were subjected to two assays. In the first, the percentage of cells positive for the cancer stem cell marker ALDH1 were determined using an ALDEFLUOR kit (Stemcell Technologies). In the second assay, for each treatment group, cells were plated into six wells of low adherence 96 well-plates at a density of 500 cells per well in 100 µl of serum-free medium containing bFGF and EGF and grown for 11 days without further treatment. After the end of this period, the number of spheroids per well was then counted.

B. Results

As shown in FIG. 24 and FIG. 25, respectively, the number of ALDH1 positive T84 and SW620 metastatic colorectal cancer cells was reduced as a result of pre-treatment for 72 hours with the anti-progastrin monoclonal antibody MAb3, compared to treatment with a control monoclonal antibody.

As shown in FIG. 26 and FIG. 27, respectively, the ability of T84 and SW620 metastatic colorectal cancer cells to grow as spheroids in low adherence culture was reduced by pretreatment for 72 hours with a monoclonal antibody against progastrin compared to a control monoclonal antibody.

Example 19

Anti-Progastrin Antibodies Reduce Initiation of New Tumors In Vivo

This example describes the effect of monoclonal antibodies specific for human progastrin on the ability of cells isolated from human metastatic colorectal cancer growing in nude mice to form new tumors after transplantation.

A. Methods

Using standard techniques, immunodeficient BALBc/nude mice were given intra-splenic injections of human metastatic SW620 colorectal cancer cells. The mice were then administered the anti-hPG monoclonal antibody MAb3 or a control monoclonal antibody twice per week for a total of six weeks. For each antibody, the dose was 8 mg/kg. At the end of the treatment period tissue was dissected from metastases from both treated and control mice. Tumor cells were disaggregated by treatment of the dissected tissue with Accumax, filtered and counted. A total of 23,800 viable tumor cells were obtained from metastatic tissue from the mice treated with MAb3, and 36,400 were obtained from control mice.

The isolated cells were then tested to determine if they exhibited phenotypic characteristics of cancer stem cells by testing if the cells could grow as spheroids under low adherence culture conditions and if they could initiate new tumors when transplanted into new hosts. For the spheroid test, for each of the treated and control cells, 2,000 cells/well were seeded into five wells of low adherence cultureware in M11 medium supplemented with bFGF and EGF. Cells were grown for seven days, and then the number of spheroids that formed in each well was counted. For the transplantation test, spheroids developing from cells isolated from treated and control metastases were pooled, disaggregated and counted. A total of 20,000 cells were obtained from spheroids derived from treated metastases, and 110,000 cells were obtained from spheroids derived from control metastases. Two new BALBc/nude mice were then transplanted with an equal number of treated or control cells. Specifically, 6,500 tumor cells derived from treated metastases were injected subcutaneously into the left thighs of the mice, whereas the same number of control cells were injected subcutaneously into the right thighs. In this manner, each mouse served as its own control. Tumor volume was then calculated through time in both animals.

B. Results

As shown in FIG. 28, growth as spheroids in low adherence culture of human metastatic colorectal cancer cells isolated from in vivo metastases was reduced by treating the animals with the anti-progastrin monoclonal antibody MAb3 as compared to treatment with the same dose of a control monoclonal antibody.

As shown in FIG. 29, the ability to initiate new tumor growth after transplantation of metastatic colorectal cancer cells isolated from in vivo metastases was also reduced by treating the cells with the anti-progastrin monoclonal antibody MAb3, as compared to treatment with the same dose of a control monoclonal antibody. In the graph, the Y-axis corresponds to tumor volume in $mm^3$. The filled squares represent tumor volume data points for one of the nude mice injected subcutaneously with metastatic colorectal cancer cells derived from metastases that grew in mice treated with a control monoclonal antibody. Conversely, the open squares represent data points for the same mouse injected in the opposite thigh with metastatic colorectal cancer cells derived from metastases that grew in mice treated with the MAb3 anti-progastrin monoclonal antibody. The filled and open diamonds correspond to similar data collected from the second nude mouse used in the experiment.

Example 20

Quantification of Plasma or Serum PG Levels

Plasma and/or serum levels of PG can be conveniently determined using the following assay. 96-well microtiter plates are coated with between 0.5 and 10 µg/mL of a C-terminal anti-hPG antibody, for example, a rabbit C-terminal anti-hPG polyclonal antibody, or a C-terminal anti-hPG antibody described herein, and then incubated overnight. Plates are then washed three times in PBS-Tween (0.05%) and blocked with 2% (w/v) nonfat dried milk in PBS-Tween (0.05%). Separately, test samples, control samples (blank or PG-negative plasma or serum samples), and between about 5 pM ($0.5 \times 10^{-11}$ M) and about 0.1 nM ($1 \times 10^{-10}$ M) of an hPG reference standard (lyophilized hPG diluted in PG-negative plasma or serum) are prepared in an appropriate diluent (e.g., PBS-Tween 0.05%). Samples are incubated on the coated plates for between 2 and 4 hours at 37° C., or alternatively between 12 and 16 hours at 21° C. After incubation, plates are washed three times with PBS-Tween (0.05%) and incubated with between 0.001 and 0.1 µg/mL of an N-terminal anti-hPG antibody, for example, a polyclonal N-terminal anti-hPG antibody or an N-terminal monoclonal anti-hPG antibody as described herein, coupled to horseradish peroxidase (HRP) ((see, Nakane et al., 1974, J. Histochem. Cytochem. 22(12): 1084-1091)) for 30 minutes at 21° C. Plates are then washed three times in PBS-Tween (0.05%) and HRP substrate is added for 15 minutes at 21° C. The reaction is stopped by added 100 µL of 0.5M sulfuric acid and an optical density measurement is taken at 405 nm. Test sample hPG levels are determined by comparison to a standard curve constructed from the measurements derived from the hPG reference standard.

Example 21

ELISA Assay for Assessing Specificity of Anti-hPG Antibodies

Specificity of anti-hPG antibodies can be conveniently determined using an ELISA assays as follows. 96-well plates are incubated overnight at 4° C. with appropriate concentration(s) of test polypeptide (e.g., 25 and 50 ng recombinant human PG, and 50 and 250 ng CTFP or other gastrin-derived gene products) in Phosphate-Buffered Saline (PBS), after which the wells are washed three times with wash solution (PBS and 0.1% Tween-20), and then incubated for 2 hours at 22° C. with 100 µL blocking solution (PBS, 0.1% Tween-20, 0.1% Bovine Serum Albumin or casein hydrolysate) per well. After blocking, the wells are washed three times and the antibody to be assayed (test antibody) is added. 100 µL of the test antibody (at 0.3 to 1 ng/mL) in PBS and 0.1% Tween-20 are added to each well. Plates are then incubated for 2 hours at 22° C., after which the test antibody solution is discarded and replaced, after a wash step (3×100 µL wash solution, as noted above), with blocking solution containing a secondary antibody, a goat anti-mouse IgG (Fc) antibody coupled to horseradish peroxidase. After a 1-hour incubation with secondary antibody, 100 µL of substrate solution (e.g. Fast OPD, or O-Phenylenediamine dihydrochloride, available from Sigma-Aldrich Co., prepared according to manufacturer's directions) is added to each well and incubated in the dark for 20 minutes at 22° C. The reaction is stopped by adding 50 µL of 4N sulfuric acid and the amount of substrate catalyzed determined by measuring the optical density (O.D.) at 492 nm. Substrate conversion is proportional to the amount of primary (test) antibody bound to the antigen. Experiments are run in duplicate and OD measurements plotted as a function of antigen concentration. Test antibodies are scored as specific for PG if the measured O.D. is between 0.2 and 1.5 for hPG and there is no statistically significant signal above background with CTFP or any of the other gastrin-gene derived peptides, where the background is the average signal from control wells containing only PBS.

Example 22

Assay for Assessing Neutralizing Activity of Anti-hPG Antibodies

A specific test for assessing whether a specific anti-hPG antibody is neutralizing can be performed as follows. Colorectal cancer cells are seeded in a 6-well plate, at approximately 50,000 to 100,000 cells per well. Cells are then treated at 12 hour intervals for 48 hours with the test anti-hPG antibody or a control antibody, at antibody concentrations of about 5 µg/mL. A test antibody is defined as neutralizing in the assay if the number of cells treated with the test antibody shows a statistically significant reduction of at least 10% in the number of surviving cells compared to the number of cells treated with a control, non-specific antibody, using a two-tailed Mann-Whitney test (with differences considered as significant when $p<0.05$). Total cell numbers are corrected for the number of cells at the start of the treatment period, referred to as $T_0$. Exemplary colorectal cancer cells for use in this assay include, but are not limited to, the primary and metastatic colorectal cancer cell lines disclosed herein.

Example 23

Assay for Assessing Affinity of an Anti-hPG Antibody

Affinity constants of anti-hPG antibodies can be measured using the Proteon Technique (BioRad), according to Nahshol et al., 2008, Analytical Biochemistry 383:52-60, hereby incorporated by reference in its entirety. Briefly, for murine anti-PG antibodies, an anti-mouse IgG antibody (50 µg/ml) is first coated on a sensor chip, making sure that the signal detected by the chip after injection of the antibody falls between 10,000 and 11,500 response units (RU). The murine anti-hPG antibody of interest (test antibody) is then injected (at a typical concentration of 30 µg/ml). If the test antibody binds sufficiently, and additional signal of at least 500 RU will be observed. A time-course of binding between test antibody and hPG is then obtained by injecting varying concentrations of hPG, for example 200 nM, 100 nM, 50 nM, 25 nM, and 12.5 nM, and detecting the level of association. Typically, several channels are available to test multiple antibodies in parallel in a single experiment, making it possible to assay binding of a single test antibody at different concentrations of hPG in parallel. One channel should be injected with a murine monoclonal antibody that is not specific to hPG as a control for non-specific binding and another channel should be injected with dilution buffer alone as a baseline for the background signal. Generally, no binding is detectable in the channel injected with non-specific murine antibody. Antibodies displaying a high level of association in this setting, which may result in saturation of the trapped monoclonal antibody by hPG, can be tested against lower hPG concentrations (50 nM, 25 nM, 12.5 nM, 6.25 nM and 3.125 nM), allowing for a more refined measurement.

Affinity constants ($K_D$) are calculated as the ratio between the dissociation constant ($k_d$) and the association constant ($k_a$). Experimental values can be validated by analyzing the statistically relevant similarity between experimental curves based on binding measurements and theoretical profiles.

Affinity constants of non-murine anti-hPG antibodies can be assessed in a similar format using an IgG specific for the species of origin of the anti-hPG test antibody.

Example 24

Assay for Assessing Competitive Binding with a Reference Anti-hPG Antibody

A specific assay for assessing whether an antibody of interest (test antibody) competes for binding hPG with a biotinylated reference anti-hPG antibody can be performed as follows. 96-well plates are coated with a capture anti-hPG antibody (polyclonal or monoclonal antibody recognizing an N- or C-terminal region of hPG that differs from the epitope recognized by the biotinylated reference anti-hPG antibody), at a concentration to be chosen within the range of 1-10 µg/ml, overnight at 4° C. (0.1 to 1 µg/well). After blocking with blocking buffer (0.1% Tween-20, 0.1% BSA in PBS) for 2 hr at 22° C., recombinant hPG is added at a concentration ranging between 10 pM to 1 nM (10 to 1000 pg/well) and incubated for 2 hr at 22° C. Thereafter, the biotinylated reference anti-hPG antibody (or a mixture containing the biotinylated reference anti-hPG antibody) is added, along with increasing concentrations of unlabeled test antibody, and incubated for 1 hr at 22° C. After washing to remove unbound antibodies, detection of bound labeled reference anti-hPG antibody is performed by incubating the mixture with 50 ng/ml steptavidin-HRP for 1 hr at 22° C., followed by incubation with a fluorogenic substrate for horseradish peroxidase and then quantifying the relative light units (RLU) in a luminometer. Assays are performed in duplicate.

Antibodies that compete with a reference anti-hPG antibody inhibit the binding of the reference antibody to hPG. An antibody that binds to substantially the same epitope, or with an overlapping epitope, as the reference antibody significantly reduces (for example, by at least 50%) the amount of reference anti-hPG antibody bound, as evidenced by a reduction observed RLUs.

A high control value is obtained from a control experiment carried out by incubating the labeled reference antibody with recombinant hPG without test antibody. A low control value is obtained from a control experiment carried out by incubating the labeled reference antibody with recombinant hPG in the presence of excess concentrations of the unlabeled reference antibody (the unlabeled reference antibody thus competing with the labeled antibody for binding to hPG). The capacity of test antibodies to compete with the reference anti-hPG antibody is then determined by incubating the labeled reference antibody with recombinant hPG in the presence of increasing concentrations of the unlabeled test antibody.

In a test assay, a significant reduction in the observed RLUs in the presence of a test antibody indicates that the test antibody recognizes substantially the same epitope as the reference anti-hPG antibody.

The inhibition of binding can be expressed as an inhibition constant, or $K_i$, which is calculated according to the following formula:

$$K_i = IC_{50}/(1+([\text{reference anti-hPG Ab concentration}]/K_D^{\text{reference anti-hPG Ab}}))$$

where "$IC_{50}$" is the concentration of test antibody that yields a 50% reduction in binding of the reference antibody and $K_D^{\text{reference anti-hPG Ab}}$ is the dissociation constant of the reference anti-hPG antibody, a measure of its affinity for hPG. Useful test antibodies that compete with a reference anti-hPG antibody (for example, one of the anti-hPG antibodies described herein) will typically have $K_i$s ranging from 10 pM to 100 nM under assay conditions described herein.

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention(s).

What is claimed is:

1. A method for treating metastatic colorectal cancer, comprising the step of administering to a human patient in need of treatment for metastatic colorectal cancer a therapeutically effective amount of a composition comprising an anti-hPG antibody, wherein said anti-hPG antibody is a monoclonal antibody that binds to human progastrin polypeptide (hPG) having an amino acid sequence of SEQ ID NO:101 but does not detectably bind to an amidated gastrin 17 consisting of SEQ ID NO:104, a glycine-extended gastrin 17 consisting of SEQ ID NO:105, or C-terminal Flanking Peptide (CTFP) consisting of SEQ ID NO:106, in which the anti-hPG antibody is a C-terminal anti-hPG antibody.

2. The method of claim 1 in which the C-terminal anti-hPG monoclonal antibody is raised against an immunogen comprising a peptide having the sequence QGPWLEEEEEAYG-WMDFGRRSAEDEN (SEQ ID NO:27).

3. The method of claim 1 in which the C-terminal anti-hPG monoclonal antibody competes for binding to hPG with a reference antibody selected from:
   (a) a monoclonal antibody comprising a heavy chain variable domain sequence of SEQ ID NO:59 and a light chain variable domain sequence of SEQ ID NO:63;
   (b) a monoclonal antibody comprising a heavy chain variable domain sequence of SEQ ID NO:60 and a light chain variable domain sequence of SEQ ID NO:64.

4. The method of claim 1, wherein the C-terminal anti-hPG antibody binds an epitope in a C-terminal epitope region of hPG comprising the amino acid sequence of SEQ ID NO:33.

5. The method of claim 1, wherein the C-terminal anti-hPG antibody binds an epitope in a C-terminal epitope region of hPG comprising the amino acid sequence of SEQ ID NO:34.

6. The method of claim 1, wherein the C-terminal anti-hPG antibody binds an epitope in a C-terminal epitope region of hPG comprising the amino acid sequence of SEQ ID NO:35.

7. The method of claim 1, wherein the C-terminal anti-hPG antibody binds an epitope in a C-terminal epitope region of hPG comprising the amino acid sequence of SEQ ID NO:36.

8. The method of claim 1, wherein said anti-hPG monoclonal antibody comprises a heavy chain variable region in which CDR1 comprises the amino acid sequence of $V_H$ CDR 1.8 (SEQ ID NO:37), CDR2 comprises the amino acid sequence of $V_H$ CDR 2.8 (SEQ ID NO:41), and CDR3 comprises the amino acid sequence of $V_H$ CDR 3.8 (SEQ ID NO:45), and a light chain variable region in which CDR1 comprises the amino acid sequence of $V_L$ CDR 1.8 (SEQ ID NO:49), CDR2 comprises the amino acid sequence of $V_L$ CDR 2.8 (SEQ ID NO:52), and CDR3 comprises the amino acid sequence of $V_L$ CDR 3.8 (SEQ ID NO:55).

9. The method of claim 1, wherein said anti-hPG monoclonal antibody comprises a heavy chain variable region in which CDR1 comprises the amino acid sequence of $V_H$ CDR 1.13 (SEQ ID NO:38), CDR2 comprises the amino acid sequence of $V_H$ CDR 2.13 (SEQ ID NO:42), and CDR3 comprises the amino acid sequence of $V_H$ CDR 3.13 (SEQ ID NO:46), and a light chain variable region in which CDR1 comprises the amino acid sequence of $V_L$ CDR 1.13 (SEQ ID NO:50), CDR2 comprises the amino acid sequence of $V_L$ CDR 2.13 (SEQ ID NO:53), and CDR3 comprises the amino acid sequence of $V_L$ CDR 3.13 (SEQ ID NO:56).

* * * * *

SEQUENCE LISTING

<160> NUMBER OF SEQ ID NOS: 106

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Tyr Ile Phe Thr Ser Tyr Trp
1               5

<210> SEQ ID NO 2
<211> LENGTH: 8

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Phe Tyr Pro Gly Asn Ser Asp Ser
1               5

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Thr Arg Arg Asp Ser Pro Gln Tyr
1               5

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gln Ser Ile Val His Ser Asn Gly Asn Thr Tyr
1               5                   10

<210> SEQ ID NO 5
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Lys Val Ser
1

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Phe Gln Gly Ser His Val Pro Phe Thr
1               5

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gly Tyr Thr Phe Ser Ser Ser Trp
```

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Phe Leu Pro Gly Ser Gly Ser Thr
1               5

<210> SEQ ID NO 9
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ala Thr Asp Gly Asn Tyr Asp Trp Phe Ala Tyr
1               5                   10

<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gln Ser Leu Val His Ser Ser Gly Val Thr Tyr
1               5                   10

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ser Gln Ser Thr His Val Pro Pro Thr
1               5

<210> SEQ ID NO 12
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Glu Val Gln Leu Gln Gln Ser Gly Thr Val Leu Ala Arg Pro Gly Ala
1               5                   10                  15

Ser Val Lys Met Ser Cys Lys Ala Ser Gly Tyr Ile Phe Thr Ser Tyr
            20                  25                  30

Trp Val His Trp Val Lys Gln Arg Pro Gly Gln Gly Leu Glu Trp Ile
        35                  40                  45

Gly Gly Phe Tyr Pro Gly Asn Ser Asp Ser Arg Tyr Asn Gln Lys Phe

```
                50                  55                  60
Lys Gly Lys Ala Thr Leu Thr Ala Val Thr Ser Ala Ser Thr Ala Tyr
 65                  70                  75                  80

Met Asp Leu Ser Ser Leu Thr Asn Glu Asp Ser Ala Val Tyr Phe Cys
                 85                  90                  95

Thr Arg Arg Asp Ser Pro Gln Tyr Trp Gly Gln Gly Thr Thr Leu Thr
                100                 105                 110

Val Ser Ser
        115

<210> SEQ ID NO 13
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Asp Val Leu Met Thr Gln Thr Pro Leu Ser Leu Pro Val Ser Leu Gly
  1               5                  10                  15

Asp Gln Ala Ser Ile Ser Cys Arg Ser Ser Gln Ser Ile Val His Ser
                 20                  25                  30

Asn Gly Asn Thr Tyr Leu Glu Trp Tyr Leu Gln Lys Pro Gly Gln Ser
             35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Leu Glu Ala Glu Asp Leu Gly Val Tyr Tyr Cys Phe Gln Gly
                 85                  90                  95

Ser His Val Pro Phe Thr Phe Gly Gly Gly Thr Lys Leu Glu Ile Lys
                100                 105                 110

<210> SEQ ID NO 14
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Gln Val Gln Leu Gln Gln Ser Gly Ala Glu Leu Met Lys Pro Gly Ala
  1               5                  10                  15

Ser Val Lys Ile Ser Cys Lys Ala Thr Gly Tyr Thr Phe Ser Ser Ser
                 20                  25                  30

Trp Ile Glu Trp Leu Lys Gln Arg Pro Gly His Gly Leu Glu Trp Ile
             35                  40                  45

Gly Glu Phe Leu Pro Gly Ser Gly Ser Thr Asp Tyr Asn Glu Lys Phe
 50                  55                  60

Lys Gly Lys Ala Thr Phe Thr Ala Asp Thr Ser Ser Asp Thr Ala Tyr
 65                  70                  75                  80

Met Leu Leu Ser Ser Leu Thr Ser Glu Asp Ser Ala Val Tyr Tyr Cys
                 85                  90                  95

Ala Thr Asp Gly Asn Tyr Asp Trp Phe Ala Tyr Trp Gly Gln Gly Thr
                100                 105                 110

Leu Val Thr Val Ser Ala
```

<210> SEQ ID NO 15
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 15

```
Asp Leu Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Ser Gly Val Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Pro Thr Phe Gly Ser Gly Thr Lys Leu Glu Ile Lys
            100                 105                 110
```

<210> SEQ ID NO 16
<211> LENGTH: 345
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: CDS
<222> LOCATION: (1)..(345)

<400> SEQUENCE: 16

```
gag gtt cag ctc cag cag tct ggg act gtg ctg gca agg cct ggg gct      48
Glu Val Gln Leu Gln Gln Ser Gly Thr Val Leu Ala Arg Pro Gly Ala
1               5                   10                  15 tcc gtg aag atg tcc tgc aag gct tct ggc tac atc ttt acc agc tac      96
Ser Val Lys Met Ser Cys Lys Ala Ser Gly Tyr Ile Phe Thr Ser Tyr
            20                  25                  30 tgg gta cac tgg gtt aaa cag agg cct gga cag ggt cta gaa tgg att     144
Trp Val His Trp Val Lys Gln Arg Pro Gly Gln Gly Leu Glu Trp Ile
        35                  40                  45 ggt ggt ttt tat cct gga aat agt gat tct agg tac aac cag aaa ttc     192
Gly Gly Phe Tyr Pro Gly Asn Ser Asp Ser Arg Tyr Asn Gln Lys Phe
    50                  55                  60 aag ggc aag gcc aca ctg act gca gtc aca tcc gcc agt act gcc tac     240
Lys Gly Lys Ala Thr Leu Thr Ala Val Thr Ser Ala Ser Thr Ala Tyr
65                  70                  75                  80 atg gac ctc agc agc ctg aca aat gag gac tct gcg gtc tat ttc tgt     288
Met Asp Leu Ser Ser Leu Thr Asn Glu Asp Ser Ala Val Tyr Phe Cys
                85                  90                  95 aca aga aga gat agt ccc cag tac tgg ggc caa ggc acc act ctc aca     336
Thr Arg Arg Asp Ser Pro Gln Tyr Trp Gly Gln Gly Thr Thr Leu Thr
            100                 105                 110 gtc tcc tca                                                          345
Val Ser Ser
        115
```

<210> SEQ ID NO 17
<211> LENGTH: 336
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: CDS
<222> LOCATION: (1)..(336)

<400> SEQUENCE: 17

```
gat gtt ttg atg acc caa act cca ctc tcc ctg cct gtc agt ctt gga      48
Asp Val Leu Met Thr Gln Thr Pro Leu Ser Leu Pro Val Ser Leu Gly
1               5                   10                  15 gat caa gcc tcc atc tct tgc aga tct agt cag agc att gta cat agt      96
Asp Gln Ala Ser Ile Ser Cys Arg Ser Ser Gln Ser Ile Val His Ser
            20                  25                  30 aat gga aac acc tat tta gaa tgg tac ctg cag aaa cca ggc cag tct     144
Asn Gly Asn Thr Tyr Leu Glu Trp Tyr Leu Gln Lys Pro Gly Gln Ser
        35                  40                  45 cca aag ctc ctg atc tac aaa gtt tcc aac cga ttt tct ggg gtc cca     192
Pro Lys Leu Leu Ile Tyr Lys Val Ser Asn Arg Phe Ser Gly Val Pro
    50                  55                  60 gac agg ttc agt ggc agt gga tca ggg aca gat ttc aca ctc aag atc     240
Asp Arg Phe Ser Gly Ser Gly Ser Gly Thr Asp Phe Thr Leu Lys Ile
65                  70                  75                  80 agc aga ctg gag gct gag gat ctg gga gtt tat tac tgc ttt caa ggt     288
Ser Arg Leu Glu Ala Glu Asp Leu Gly Val Tyr Tyr Cys Phe Gln Gly
                85                  90                  95 tca cat gtt ccg ttc acg ttc gga ggg ggg acc aag ctg gaa ata aaa     336
Ser His Val Pro Phe Thr Phe Gly Gly Gly Thr Lys Leu Glu Ile Lys
            100                 105                 110
```

<210> SEQ ID NO 18
<211> LENGTH: 354
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: CDS
<222> LOCATION: (1)..(354)

<400> SEQUENCE: 18

```
cag gtt cag ttg cag cag tct gga gct gag ctg atg aag cca ggg gcc      48
Gln Val Gln Leu Gln Gln Ser Gly Ala Glu Leu Met Lys Pro Gly Ala
1               5                   10                  15 tca gtg aag ata tcc tgc aag gct act ggc tac aca ttc agt agc tcc      96
Ser Val Lys Ile Ser Cys Lys Ala Thr Gly Tyr Thr Phe Ser Ser Ser
            20                  25                  30 tgg ata gag tgg tta aaa cag agg cct gga cat ggc ctt gag tgg att     144
Trp Ile Glu Trp Leu Lys Gln Arg Pro Gly His Gly Leu Glu Trp Ile
        35                  40                  45 gga gag ttt tta cct gga agt ggt agt aca gac tac aat gag aag ttc     192
Gly Glu Phe Leu Pro Gly Ser Gly Ser Thr Asp Tyr Asn Glu Lys Phe
    50                  55                  60 aag ggc aag gcc aca ttc act gca gac aca tcc tcc gac aca gcc tac     240
Lys Gly Lys Ala Thr Phe Thr Ala Asp Thr Ser Ser Asp Thr Ala Tyr
65                  70                  75                  80 atg cta ctc agc agc ctg aca tct gag gac tct gcc gtc tat tac tgt     288
Met Leu Leu Ser Ser Leu Thr Ser Glu Asp Ser Ala Val Tyr Tyr Cys
```

```
                    85                  90                  95
gca act gat ggt aat tat gac tgg ttt gct tac tgg ggc caa ggg act        336
Ala Thr Asp Gly Asn Tyr Asp Trp Phe Ala Tyr Trp Gly Gln Gly Thr
            100                 105                 110 ctg gtc act gtc tct gca                                                354
Leu Val Thr Val Ser Ala
        115

<210> SEQ ID NO 19
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(336)

<400> SEQUENCE: 19 gat ctt gtg atg acc caa act cca ctc tcc ctg cct gtc agt ctt gga        48
Asp Leu Val Met Thr Gln Thr Pro Leu Ser Leu Pro Val Ser Leu Gly
1               5                   10                  15 gat caa gcc tcc atc tct tgc aga tct agt cag agc ctt gta cac agt        96
Asp Gln Ala Ser Ile Ser Cys Arg Ser Ser Gln Ser Leu Val His Ser
            20                  25                  30 agt gga gtc acc tat tta cat tgg tac ctg cag aag cca ggc cag tct       144
Ser Gly Val Thr Tyr Leu His Trp Tyr Leu Gln Lys Pro Gly Gln Ser
        35                  40                  45 cca aag ctc ctg atc tac aaa gtt tcc aac cga ttt tct ggg gtc cca       192
Pro Lys Leu Leu Ile Tyr Lys Val Ser Asn Arg Phe Ser Gly Val Pro
    50                  55                  60 gac agg ttc agt ggc agt gga tca ggg aca gat ttc aca ctc aag atc       240
Asp Arg Phe Ser Gly Ser Gly Ser Gly Thr Asp Phe Thr Leu Lys Ile
65                  70                  75                  80 agc aga gtg gag gct gag gat ctg gga gtt tat ttc tgc tct caa agt       288
Ser Arg Val Glu Ala Glu Asp Leu Gly Val Tyr Phe Cys Ser Gln Ser
                85                  90                  95 aca cat gtt cct ccc acg ttc ggc tcg ggg aca aag ttg gaa ata aaa       336
Thr His Val Pro Pro Thr Phe Gly Ser Gly Thr Lys Leu Glu Ile Lys
            100                 105                 110

<210> SEQ ID NO 20
<211> LENGTH: 80
<212> TYPE: PRT
<213> ORGANISM: Homo sapiens

<400> SEQUENCE: 20

Ser Trp Lys Pro Arg Ser Gln Gln Pro Asp Ala Pro Leu Gly Thr Gly
1               5                   10                  15

Ala Asn Arg Asp Leu Glu Leu Pro Trp Leu Glu Gln Gly Pro Ala
            20                  25                  30

Ser His His Arg Arg Gln Leu Gly Pro Gln Gly Pro Pro His Leu Val
        35                  40                  45

Ala Asp Pro Ser Lys Lys Gln Gly Pro Trp Leu Glu Glu Glu Glu
    50                  55                  60

Ala Tyr Gly Trp Met Asp Phe Gly Arg Arg Ser Ala Glu Asp Glu Asn
65                  70                  75                  80

<210> SEQ ID NO 21
<211> LENGTH: 115
<212> TYPE: PRT
```

<213> ORGANISM: Artificial Sequence
<220> FEATURE:
<223> OTHER INFORMATION: Description of Artificial Sequence: Synthetic polypeptide

<400> SEQUENCE: 21

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Ser Tyr
            20                  25                  30

Trp Val His Trp Val Arg Gln Ala Pro Gly Gln Arg Leu Glu Trp Met
        35                  40                  45

Gly Gly Phe Tyr Pro Gly Asn Ser Asp Ser Arg Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Arg Asp Ser Pro Gln Tyr Trp Gly Gln Gly Thr Leu Val Thr
            100                 105                 110

Val Ser Ser
        115
```

<210> SEQ ID NO 22
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 22

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Val His Ser
            20                  25                  30

Asn Gly Asn Thr Tyr Leu Glu Trp Phe Gln Gln Arg Pro Gly Gln Ser
        35                  40                  45

Pro Arg Arg Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Phe Thr Phe Gly Gly Gly Thr Lys Val Glu Ile Lys
            100                 105                 110
```

<210> SEQ ID NO 23
<211> LENGTH: 118
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 23

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Ser Ser
            20                  25                  30
```

```
Trp Met His Trp Val Arg Gln Ala Pro Gly Gln Gly Leu Glu Trp Met
            35                  40                  45

Gly Ile Phe Leu Pro Gly Ser Gly Ser Thr Asp Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Thr Asp Gly Asn Tyr Asp Trp Phe Ala Tyr Trp Gly Gln Gly Thr
            100                 105                 110

Leu Val Thr Val Ser Ser
        115

<210> SEQ ID NO 24
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Val His Ser
            20                  25                  30

Ser Gly Val Thr Tyr Leu Tyr Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Pro Thr Phe Gly Gln Gly Thr Lys Leu Glu Ile Lys
            100                 105                 110

<210> SEQ ID NO 25
<211> LENGTH: 14
<212> TYPE: PRT
<213> ORGANISM: Homo sapiens

<400> SEQUENCE: 25

Ser Trp Lys Pro Arg Ser Gln Gln Pro Asp Ala Pro Leu Gly
1               5                   10

<210> SEQ ID NO 26
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)
<223> OTHER INFORMATION: Ahx

<400> SEQUENCE: 26

Ser Trp Lys Pro Arg Ser Gln Gln Pro Asp Ala Pro Leu Gly Xaa Cys
1               5                   10                  15
```

```
<210> SEQ ID NO 27
<211> LENGTH: 26
<212> TYPE: PRT
<213> ORGANISM: Homo sapiens

<400> SEQUENCE: 27

Gln Gly Pro Trp Leu Glu Glu Glu Glu Ala Tyr Gly Trp Met Asp
1               5                   10                  15

Phe Gly Arg Arg Ser Ala Glu Asp Glu Asn
            20                  25

<210> SEQ ID NO 28
<211> LENGTH: 5
<212> TYPE: PRT
<213> ORGANISM: Homo sapiens

<400> SEQUENCE: 28

Asp Ala Pro Leu Gly
1               5

<210> SEQ ID NO 29
<211> LENGTH: 6
<212> TYPE: PRT
<213> ORGANISM: Homo sapiens

<400> SEQUENCE: 29

Pro Asp Ala Pro Leu Gly
1               5

<210> SEQ ID NO 30
<211> LENGTH: 7
<212> TYPE: PRT
<213> ORGANISM: Homo sapiens

<400> SEQUENCE: 30

Pro Arg Ser Gln Gln Pro Asp
1               5

<210> SEQ ID NO 31
<211> LENGTH: 9
<212> TYPE: PRT
<213> ORGANISM: Homo sapiens

<400> SEQUENCE: 31

Trp Lys Pro Arg Ser Gln Gln Pro Asp
1               5

<210> SEQ ID NO 32
<211> LENGTH: 13
<212> TYPE: PRT
<213> ORGANISM: Homo sapiens

<400> SEQUENCE: 32

Trp Lys Pro Arg Ser Gln Gln Pro Asp Ala Pro Leu Gly
1               5                   10

<210> SEQ ID NO 33
<211> LENGTH: 4
<212> TYPE: PRT
<213> ORGANISM: Homo sapiens

<400> SEQUENCE: 33

Phe Gly Arg Arg
```

```
<210> SEQ ID NO 34
<211> LENGTH: 5
<212> TYPE: PRT
<213> ORGANISM: Homo sapiens

<400> SEQUENCE: 34

Met Asp Phe Gly Arg
1               5

<210> SEQ ID NO 35
<211> LENGTH: 5
<212> TYPE: PRT
<213> ORGANISM: Homo sapiens

<400> SEQUENCE: 35

Ala Glu Asp Glu Asn
1               5

<210> SEQ ID NO 36
<211> LENGTH: 8
<212> TYPE: PRT
<213> ORGANISM: Homo sapiens

<400> SEQUENCE: 36

Gly Trp Met Asp Phe Gly Arg Arg
1               5

<210> SEQ ID NO 37
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gly Phe Thr Phe Thr Thr Tyr Ala
1               5

<210> SEQ ID NO 38
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gly Phe Ile Phe Ser Ser Tyr Gly
1               5

<210> SEQ ID NO 39
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Gly Tyr Thr Phe Thr Ser Tyr Tyr
1               5

<210> SEQ ID NO 40
```

-continued

<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gly Tyr Ser Ile Thr Ser Asp Tyr Ala
1               5

<210> SEQ ID NO 41
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Ile Ser Ser Gly Gly Thr Tyr Thr
1               5

<210> SEQ ID NO 42
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Ile Asn Thr Phe Gly Asp Arg Thr
1               5

<210> SEQ ID NO 43
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Ile Asn Pro Ser Asn Gly Gly Thr
1               5

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Ile Ser Phe Ser Gly Tyr Thr
1               5

<210> SEQ ID NO 45
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

```
Ala Thr Gln Gly Asn Tyr Ser Leu Asp Phe
1               5                   10
```

<210> SEQ ID NO 46
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

```
Ala Arg Gly Thr Gly Thr Tyr
1               5
```

<210> SEQ ID NO 47
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

```
Thr Arg Gly Gly Tyr Tyr Pro Phe Asp Tyr
1               5                   10
```

<210> SEQ ID NO 48
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

```
Ala Arg Glu Val Asn Tyr Gly Asp Ser Tyr His Phe Asp Tyr
1               5                   10
```

<210> SEQ ID NO 49
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

```
Lys Ser Leu Arg His Thr Lys Gly Ile Thr Phe
1               5                   10
```

<210> SEQ ID NO 50
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

```
Gln Ser Leu Leu Asp Ser Asp Gly Lys Thr Tyr
1               5                   10
```

<210> SEQ ID NO 51
<211> LENGTH: 7
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 51

Ser Gln His Arg Thr Tyr Thr
1               5

<210> SEQ ID NO 52
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Gln Met Ser
1

<210> SEQ ID NO 53
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Leu Val Ser
1

<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Val Lys Lys Asp Gly Ser His
1               5

<210> SEQ ID NO 55
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Ala Gln Asn Leu Glu Leu Pro Leu Thr
1               5

<210> SEQ ID NO 56
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Trp Gln Gly Thr His Phe Pro Gln Thr
1               5

```
<210> SEQ ID NO 57
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Trp Gln Gly Thr His Ser Pro Tyr Thr
1               5

<210> SEQ ID NO 58
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Gly Val Gly Asp Ala Ile Lys Gly Gln Ser Val Phe Val
1               5                   10

<210> SEQ ID NO 59
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Thr Thr Tyr
            20                  25                  30

Ala Met Ser Trp Val Arg Gln Thr Pro Glu Lys Arg Leu Glu Trp Val
        35                  40                  45

Ala Thr Ile Ser Ser Gly Gly Thr Tyr Thr Tyr Tyr Pro Asp Ser Val
    50                  55                  60

Lys Gly Arg Phe Thr Ile Ser Arg Asp Asn Ala Lys Asn Ala Leu Tyr
65                  70                  75                  80

Leu Gln Met Ser Ser Leu Arg Ser Glu Asp Thr Ala Met Tyr Tyr Cys
                85                  90                  95

Ala Thr Gln Gly Asn Tyr Ser Leu Asp Phe Trp Gly Gln Gly Thr Ser
            100                 105                 110

Leu Thr Val Ser Ser
        115

<210> SEQ ID NO 60
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Ile Phe Ser Ser Tyr
            20                  25                  30
```

Gly Met Ser Trp Val Arg Gln Ser Pro Asp Arg Arg Leu Glu Leu Val
             35                  40                  45

Ala Ser Ile Asn Thr Phe Gly Asp Arg Thr Tyr Tyr Pro Asp Ser Val
 50                  55                  60

Lys Gly Arg Phe Thr Ile Ser Arg Asp Asn Ala Lys Asn Thr Leu Tyr
 65                  70                  75                  80

Leu Gln Met Thr Ser Leu Lys Ser Glu Asp Thr Ala Ile Tyr Tyr Cys
                 85                  90                  95

Ala Arg Gly Thr Gly Thr Tyr Trp Gly Gln Gly Thr Thr Leu Thr Val
            100                 105                 110

Ser Ser

<210> SEQ ID NO 61
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Gln Val Gln Leu Gln Gln Ser Gly Ala Glu Leu Val Lys Pro Gly Ala
 1               5                  10                  15

Ser Val Lys Leu Ser Cys Lys Ala Ser Gly Tyr Thr Phe Thr Ser Tyr
             20                  25                  30

Tyr Met Tyr Trp Val Lys Gln Arg Pro Gly Gln Gly Leu Glu Trp Ile
             35                  40                  45

Gly Glu Ile Asn Pro Ser Asn Gly Gly Thr Asn Phe Asn Glu Lys Phe
 50                  55                  60

Lys Ser Lys Ala Thr Leu Thr Val Asp Lys Ser Ser Ser Thr Ala Tyr
 65                  70                  75                  80

Met Gln Leu Ser Ser Leu Thr Ser Glu Asp Ser Ala Val Tyr Tyr Cys
                 85                  90                  95

Thr Arg Gly Gly Tyr Tyr Pro Phe Asp Tyr Trp Gly Gln Gly Thr Thr
            100                 105                 110

Leu Thr Val Ser Ser
        115

<210> SEQ ID NO 62
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Asp Val Gln Leu Gln Glu Ser Gly Pro Gly Leu Val Lys Pro Ser Gln
 1               5                  10                  15

Ser Leu Ser Leu Thr Cys Thr Val Thr Gly Tyr Ser Ile Thr Ser Asp
             20                  25                  30

Tyr Ala Trp Asn Trp Ile Arg Gln Phe Pro Gly Asn Lys Leu Glu Trp
             35                  40                  45

Met Gly Tyr Ile Ser Phe Ser Gly Tyr Thr Ser Tyr Asn Pro Ser Leu
 50                  55                  60

Lys Ser Arg Ile Ser Val Thr Arg Asp Thr Ser Arg Asn Gln Phe Phe
 65                  70                  75                  80

Leu Gln Leu Thr Ser Val Thr Thr Glu Asp Thr Ala Thr Tyr Tyr Cys

```
            85                  90                  95
Ala Arg Glu Val Asn Tyr Gly Asp Ser Tyr His Phe Asp Tyr Trp Gly
            100                 105                 110

Gln Gly Thr Ile Val Thr Val Ser Ser
        115                 120

<210> SEQ ID NO 63
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Asp Ile Val Met Thr Gln Ala Ala Ser Ser Asn Pro Val Thr Leu Gly
1               5                   10                  15

Thr Ser Ala Ser Ile Ser Cys Arg Ser Ser Lys Ser Leu Arg His Thr
            20                  25                  30

Lys Gly Ile Thr Phe Leu Tyr Trp Tyr Leu Gln Lys Pro Gly Gln Ser
        35                  40                  45

Pro Gln Leu Leu Ile Tyr Gln Met Ser Asn Leu Ala Ser Gly Val Pro
    50                  55                  60

Asp Arg Phe Ser Ser Ser Gly Ser Gly Thr Asp Phe Thr Leu Arg Ile
65                  70                  75                  80

Ser Arg Val Glu Ala Glu Asp Leu Gly Val Tyr Tyr Cys Ala Gln Asn
                85                  90                  95

Leu Glu Leu Pro Leu Thr Phe Gly Ala Gly Thr Lys Leu Glu Leu Lys
            100                 105                 110

<210> SEQ ID NO 64
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Asp Val Val Leu Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Gln Thr Phe Gly Gly Gly Thr Lys Leu Glu Ile Lys
            100                 105                 110

<210> SEQ ID NO 65
<211> LENGTH: 112
<212> TYPE: PRT
<213> ORGANISM: Artificial Sequence
<220> FEATURE:
<223> OTHER INFORMATION: Description of Artificial Sequence: Synthetic
```

-continued polypeptide

<400> SEQUENCE: 65

Asp Val Val Met Thr Gln Thr Pro Leu Thr Leu Ser Val Thr Ile Gly
1               5                   10                  15

Arg Pro Ala Ser Ile Ser Cys Lys Ser Ser Gln Ser Leu Leu Asp Ser
            20                  25                  30

Asp Gly Lys Thr Tyr Leu Tyr Trp Leu Leu Gln Arg Pro Gly Gln Ser
        35                  40                  45

Pro Lys Arg Leu Ile Tyr Leu Val Ser Glu Leu Asp Ser Gly Val Pro
    50                  55                  60

Asp Arg Ile Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Ser Pro Tyr Thr Phe Gly Gly Gly Thr Lys Leu Glu Ile Lys
            100                 105                 110

<210> SEQ ID NO 66
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Gln Leu Ala Leu Thr Gln Ser Ser Ser Ala Ser Phe Ser Leu Gly Ala
1               5                   10                  15

Ser Ala Lys Leu Thr Cys Thr Leu Ser Ser Gln His Arg Thr Tyr Thr
            20                  25                  30

Ile Glu Trp Tyr Gln Gln Gln Ser Leu Lys Pro Pro Lys Tyr Val Met
        35                  40                  45

Glu Val Lys Lys Asp Gly Ser His Ser Thr Gly His Gly Ile Pro Asp
    50                  55                  60

Arg Phe Ser Gly Ser Ser Ser Gly Ala Asp Arg Tyr Leu Ser Ile Ser
65                  70                  75                  80

Asn Ile Gln Pro Glu Asp Glu Ala Ile Tyr Ile Cys Gly Val Gly Asp
                85                  90                  95

Ala Ile Lys Gly Gln Ser Val Phe Val Phe Gly Gly Gly Thr Lys Val
            100                 105                 110

Thr Val Leu
        115

<210> SEQ ID NO 67
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(351)

<400> SEQUENCE: 67 gaa gtg cag ctg gtg gag tct ggg gga ggc tta gtg aag cct gga ggg       48
Glu Val Gln Leu Val Glu Ser Gly Gly Gly Leu Val Lys Pro Gly Gly
1               5                   10                  15 tcc ctg aaa ctc tcc tgt gca gcc tct gga ttc act ttc act acc tat       96

```
Ser Leu Lys Leu Ser Cys Ala Ala Ser Gly Phe Thr Phe Thr Thr Tyr
         20                  25                  30 gcc atg tct tgg gtt cgc cag act ccg gag aag agg ctg gag tgg gtc    144
Ala Met Ser Trp Val Arg Gln Thr Pro Glu Lys Arg Leu Glu Trp Val
         35                  40                  45 gca acc att agt agt ggt ggt act tac acc tac tat cca gac agt gtg    192
Ala Thr Ile Ser Ser Gly Gly Thr Tyr Thr Tyr Tyr Pro Asp Ser Val
 50                  55                  60 aag ggt cga ttc acc atc tcc aga gac aat gcc aag aac gcc cta tac    240
Lys Gly Arg Phe Thr Ile Ser Arg Asp Asn Ala Lys Asn Ala Leu Tyr
 65                  70                  75                  80 ctg caa atg agc agt ctg agg tct gag gac acg gcc atg tat tac tgt    288
Leu Gln Met Ser Ser Leu Arg Ser Glu Asp Thr Ala Met Tyr Tyr Cys
             85                  90                  95 gca aca cag ggg aat tac tct ttg gac ttc tgg ggc caa ggc acc tct    336
Ala Thr Gln Gly Asn Tyr Ser Leu Asp Phe Trp Gly Gln Gly Thr Ser
            100                 105                 110 ctc aca gtc tcc tca                                                351
Leu Thr Val Ser Ser
            115

<210> SEQ ID NO 68
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(342)

<400> SEQUENCE: 68 gag gtg cag ctg gtg gag tct ggg gga ggc ttg gtg cag cct gga ggg    48
Glu Val Gln Leu Val Glu Ser Gly Gly Gly Leu Val Gln Pro Gly Gly
 1               5                  10                  15 tcc ctg aaa ctc tcc tgt gca gcc tct gga ttc att ttc agt agc tat    96
Ser Leu Lys Leu Ser Cys Ala Ala Ser Gly Phe Ile Phe Ser Ser Tyr
             20                  25                  30 ggc atg tct tgg gtt cgc cag tct cca gac agg agg ctg gag ttg gtc    144
Gly Met Ser Trp Val Arg Gln Ser Pro Asp Arg Arg Leu Glu Leu Val
         35                  40                  45 gca agt att aat act ttt ggt gat aga acc tat tat cca gac agt gtg    192
Ala Ser Ile Asn Thr Phe Gly Asp Arg Thr Tyr Tyr Pro Asp Ser Val
 50                  55                  60 aag ggc cga ttc acc atc tcc aga gac aat gcc aag aac acc ctg tac    240
Lys Gly Arg Phe Thr Ile Ser Arg Asp Asn Ala Lys Asn Thr Leu Tyr
 65                  70                  75                  80 ctg caa atg acc agt ctg aag tct gag gac aca gcc att tat tac tgt    288
Leu Gln Met Thr Ser Leu Lys Ser Glu Asp Thr Ala Ile Tyr Tyr Cys
             85                  90                  95 gca aga ggg acc gga acc tac tgg ggc caa ggc acc act ctc aca gtc    336
Ala Arg Gly Thr Gly Thr Tyr Trp Gly Gln Gly Thr Thr Leu Thr Val
            100                 105                 110 tcc tca                                                            342
Ser Ser

<210> SEQ ID NO 69
<211> LENGTH: 351
<212> TYPE: DNA
<213> ORGANISM: Artificial Sequence
<220> FEATURE:
<223> OTHER INFORMATION: Description of Artificial Sequence: Synthetic
```

```
           polynucleotide
<220> FEATURE:
<221> NAME/KEY: CDS
<222> LOCATION: (1)..(351)

<400> SEQUENCE: 69 cag gtc caa ctg cag cag tct ggg gct gaa ctg gtg aag cct ggg gct      48
Gln Val Gln Leu Gln Gln Ser Gly Ala Glu Leu Val Lys Pro Gly Ala
1               5                   10                  15 tca gtg aag ttg tcc tgc aag gct tct ggc tac acc ttc acc agc tac      96
Ser Val Lys Leu Ser Cys Lys Ala Ser Gly Tyr Thr Phe Thr Ser Tyr
            20                  25                  30 tat atg tac tgg gtg aag cag agg cct gga caa ggc ctt gag tgg att     144
Tyr Met Tyr Trp Val Lys Gln Arg Pro Gly Gln Gly Leu Glu Trp Ile
        35                  40                  45 gga gag att aat cct agc aat ggt ggt act aac ttc aat gag aag ttc     192
Gly Glu Ile Asn Pro Ser Asn Gly Gly Thr Asn Phe Asn Glu Lys Phe
    50                  55                  60 aag agc aag gcc aca ctg act gta gac aaa tcc tcc agc aca gca tac     240
Lys Ser Lys Ala Thr Leu Thr Val Asp Lys Ser Ser Ser Thr Ala Tyr
65                  70                  75                  80 atg caa ctc agc agc ctg aca tct gag gac tct gcg gtc tat tac tgt     288
Met Gln Leu Ser Ser Leu Thr Ser Glu Asp Ser Ala Val Tyr Tyr Cys
                85                  90                  95 aca aga ggc ggt tac tac ccc ttt gac tac tgg ggc caa ggc acc act     336
Thr Arg Gly Gly Tyr Tyr Pro Phe Asp Tyr Trp Gly Gln Gly Thr Thr
            100                 105                 110 ctc aca gtc tcc tca                                                 351
Leu Thr Val Ser Ser
        115

<210> SEQ ID NO 70
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(363)

<400> SEQUENCE: 70 gat gtg cag ctt cag gag tcg gga cct ggc ctg gtg aaa cct tct cag      48
Asp Val Gln Leu Gln Glu Ser Gly Pro Gly Leu Val Lys Pro Ser Gln
1               5                   10                  15 tct ctg tcc ctc aca tgc act gtc act ggc tac tca atc acc agt gat      96
Ser Leu Ser Leu Thr Cys Thr Val Thr Gly Tyr Ser Ile Thr Ser Asp
            20                  25                  30 tat gcc tgg aat tgg atc cgg cag ttt cca gga aac aaa ctg gag tgg     144
Tyr Ala Trp Asn Trp Ile Arg Gln Phe Pro Gly Asn Lys Leu Glu Trp
        35                  40                  45 atg ggc tac ata agc ttc agt ggt tac act agt tac aac cca tct ctc     192
Met Gly Tyr Ile Ser Phe Ser Gly Tyr Thr Ser Tyr Asn Pro Ser Leu
    50                  55                  60 aaa agt cga atc tct gtc act cgg gac aca tcc agg aac caa ttc ttc     240
Lys Ser Arg Ile Ser Val Thr Arg Asp Thr Ser Arg Asn Gln Phe Phe
65                  70                  75                  80 ctc cag ttg act tct gtg act act gag gac aca gcc aca tat tac tgt     288
Leu Gln Leu Thr Ser Val Thr Thr Glu Asp Thr Ala Thr Tyr Tyr Cys
                85                  90                  95 gca aga gag gtc aac tat ggg gac tcc tac cac ttt gac tac tgg ggc     336
Ala Arg Glu Val Asn Tyr Gly Asp Ser Tyr His Phe Asp Tyr Trp Gly
```

```
                       100                 105                 110
caa ggc acc att gtc aca gtc tcc tca                                         363
Gln Gly Thr Ile Val Thr Val Ser Ser
        115                 120

<210> SEQ ID NO 71
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(336)

<400> SEQUENCE: 71 gac att gtg atg acg cag gct gca tcc tct aat cca gtc act ctt gga             48
Asp Ile Val Met Thr Gln Ala Ala Ser Ser Asn Pro Val Thr Leu Gly
1               5                   10                  15 aca tcc gct tcc atc tcc tgc agg tct agt aag agt ctc cga cat act             96
Thr Ser Ala Ser Ile Ser Cys Arg Ser Ser Lys Ser Leu Arg His Thr
            20                  25                  30 aaa ggc atc act ttt ttg tat tgg tat ctg cag aag cca ggc cag tct            144
Lys Gly Ile Thr Phe Leu Tyr Trp Tyr Leu Gln Lys Pro Gly Gln Ser
        35                  40                  45 cct cag ctc ctg att tat cag atg tcc aac ctt gcc tca gga gtc cca            192
Pro Gln Leu Leu Ile Tyr Gln Met Ser Asn Leu Ala Ser Gly Val Pro
    50                  55                  60 gac agg ttc agt agc agt ggg tca gga act gat ttc aca ctg aga atc            240
Asp Arg Phe Ser Ser Ser Gly Ser Gly Thr Asp Phe Thr Leu Arg Ile
65                  70                  75                  80 agc aga gtg gag gct gag gat ttg ggt gtt tat tac tgt gct caa aat            288
Ser Arg Val Glu Ala Glu Asp Leu Gly Val Tyr Tyr Cys Ala Gln Asn
                85                  90                  95 cta gaa ctt ccg ctc acg ttc ggt gct ggg acc aag ctg gag ctg aaa            336
Leu Glu Leu Pro Leu Thr Phe Gly Ala Gly Thr Lys Leu Glu Leu Lys
            100                 105                 110

<210> SEQ ID NO 72
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(336)

<400> SEQUENCE: 72 gat gtt gtg ctg acc cag act cca ctc act ttg tcg gtt acc att gga             48
Asp Val Val Leu Thr Gln Thr Pro Leu Thr Leu Ser Val Thr Ile Gly
1               5                   10                  15 caa cca gcc tcc atc tcc tgc aag tca agt cag agc ctc tta gat agt             96
Gln Pro Ala Ser Ile Ser Cys Lys Ser Ser Gln Ser Leu Leu Asp Ser
            20                  25                  30 gat gga aag aca tat ttg aat tgg ttg tta cag agg cca ggc cag tct            144
Asp Gly Lys Thr Tyr Leu Asn Trp Leu Leu Gln Arg Pro Gly Gln Ser
        35                  40                  45 cca aag cgc cta atc tat ctg gtg tct aaa ctg gac tct gga gtc cct            192
Pro Lys Arg Leu Ile Tyr Leu Val Ser Lys Leu Asp Ser Gly Val Pro
    50                  55                  60 gac agg ttc act ggc agt gga tca ggg aca gat ttc aca ctg aaa atc            240
```

| | | | | | | | | | | | | | | | | |
|---|---|---|---|---|---|---|---|---|---|---|---|---|---|---|---|---|
|Asp|Arg|Phe|Thr|Gly|Ser|Gly|Ser|Gly|Thr|Asp|Phe|Thr|Leu|Lys|Ile| |
|65| | | |70| | | |75| | | |  |  |80|  | |

```
agc aga gtg gag gct gag gat ttg gga gtt tat tat tgc tgg caa ggt       288
Ser Arg Val Glu Ala Glu Asp Leu Gly Val Tyr Tyr Cys Trp Gln Gly
                85                  90                  95 aca cat ttt cct cag acg ttc ggt gga ggc acc aag ctg gaa atc aaa       336
Thr His Phe Pro Gln Thr Phe Gly Gly Gly Thr Lys Leu Glu Ile Lys
            100                 105                 110
```

<210> SEQ ID NO 73
<211> LENGTH: 336
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: CDS
<222> LOCATION: (1)..(336)

<400> SEQUENCE: 73

```
gat gtt gtg atg acc cag act cca ctc act ttg tcg gtt acc att ggg        48
Asp Val Val Met Thr Gln Thr Pro Leu Thr Leu Ser Val Thr Ile Gly
1               5                   10                  15 cgc cca gcc tcc atc tct tgc aag tca agt cag agc ctc tta gac agt        96
Arg Pro Ala Ser Ile Ser Cys Lys Ser Ser Gln Ser Leu Leu Asp Ser
                20                  25                  30 gat gga aag aca tat ttg tat tgg ttg tta cag agg cca ggc cag tct       144
Asp Gly Lys Thr Tyr Leu Tyr Trp Leu Leu Gln Arg Pro Gly Gln Ser
            35                  40                  45 cca aag cgc cta atc tat ctg gtg tct gag ctg gac tct gga gtc cct       192
Pro Lys Arg Leu Ile Tyr Leu Val Ser Glu Leu Asp Ser Gly Val Pro
        50                  55                  60 gac agg atc act ggc agt ggg tcg ggg aca gat ttc aca ctg aag atc       240
Asp Arg Ile Thr Gly Ser Gly Ser Gly Thr Asp Phe Thr Leu Lys Ile
65                  70                  75                  80 agc aga gtg gag gct gag gat ttg gga gtt tat tat tgc tgg caa gga       288
Ser Arg Val Glu Ala Glu Asp Leu Gly Val Tyr Tyr Cys Trp Gln Gly
                85                  90                  95 aca cat tct ccg tac acg ttc gga ggg ggg acc aag ctg gaa ata aaa       336
Thr His Ser Pro Tyr Thr Phe Gly Gly Gly Thr Lys Leu Glu Ile Lys
            100                 105                 110
```

<210> SEQ ID NO 74
<211> LENGTH: 345
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: CDS
<222> LOCATION: (1)..(345)

<400> SEQUENCE: 74

```
caa ctt gcg ctc act cag tca tct tca gcc tct ttc tcc ctg gga gcc        48
Gln Leu Ala Leu Thr Gln Ser Ser Ser Ala Ser Phe Ser Leu Gly Ala
1               5                   10                  15 tca gca aaa cta acg tgc act ttg agt agt caa cac aga acg tac acc        96
Ser Ala Lys Leu Thr Cys Thr Leu Ser Ser Gln His Arg Thr Tyr Thr
                20                  25                  30 att gaa tgg tat cag caa cag tca ctc aag cct cct aag tat gtg atg       144
Ile Glu Trp Tyr Gln Gln Gln Ser Leu Lys Pro Pro Lys Tyr Val Met
            35                  40                  45
```

```
gag gtt aag aaa gat gga agc cac agc aca ggt cat ggg att cct gat      192
Glu Val Lys Lys Asp Gly Ser His Ser Thr Gly His Gly Ile Pro Asp
 50                  55                  60 cgc ttc tct gga tcc agt tct ggt gct gat cgc tac ctc agc att tcc      240
Arg Phe Ser Gly Ser Ser Ser Gly Ala Asp Arg Tyr Leu Ser Ile Ser
 65                  70                  75                  80 aac atc cag cct gaa gat gaa gca ata tac atc tgt ggt gtg ggt gat      288
Asn Ile Gln Pro Glu Asp Glu Ala Ile Tyr Ile Cys Gly Val Gly Asp
                 85                  90                  95 gca att aag gga caa tct gtg ttt gtt ttc ggc ggt ggc acc aag gtc      336
Ala Ile Lys Gly Gln Ser Val Phe Val Phe Gly Gly Gly Thr Lys Val
            100                 105                 110 act gtc cta                                                          345
Thr Val Leu
        115
```

<210> SEQ ID NO 75
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

```
Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Thr Thr Tyr
            20                  25                  30

Ala Met Ser Trp Val Arg Gln Ala Pro Gly Lys Gly Leu Glu Trp Val
        35                  40                  45

Ser Ser Ile Ser Ser Gly Gly Thr Tyr Thr Tyr Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Thr Gln Gly Asn Tyr Ser Leu Asp Phe Trp Gly Gln Gly Thr Thr
            100                 105                 110

Val Thr Val Ser Ser
        115
```

<210> SEQ ID NO 76
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

```
Asp Ile Val Met Thr Gln Ser Pro Leu Ser Leu Pro Val Thr Pro Gly
 1               5                  10                  15

Glu Pro Ala Ser Ile Ser Cys Arg Ser Ser Lys Ser Leu Arg His Thr
            20                  25                  30

Lys Gly Ile Thr Phe Leu Tyr Trp Tyr Leu Gln Lys Pro Gly Gln Ser
        35                  40                  45

Pro Gln Leu Leu Ile Tyr Gln Met Ser Asn Arg Ala Ser Gly Val Pro
 50                  55                  60

Asp Arg Phe Ser Gly Ser Gly Ser Gly Thr Asp Phe Thr Leu Lys Ile
```

```
                65                  70                  75                  80
Ser Arg Val Glu Ala Glu Asp Val Gly Val Tyr Tyr Cys Ala Gln Asn
                    85                  90                  95

Leu Glu Leu Pro Leu Thr Phe Gly Gly Gly Thr Lys Val Glu Ile Lys
            100                 105                 110

<210> SEQ ID NO 77
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Thr Thr Tyr
            20                  25                  30

Ala Met Asn Trp Val Arg Gln Ala Pro Gly Lys Gly Leu Glu Trp Val
        35                  40                  45

Ser Ser Ile Ser Ser Gly Gly Thr Tyr Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Thr Gln Gly Asn Tyr Ser Leu Asp Phe Trp Gly Gln Gly Thr Thr
            100                 105                 110

Val Thr Val Ser Ser
        115

<210> SEQ ID NO 78
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Arg His Thr
            20                  25                  30

Lys Gly Ile Thr Phe Leu Asp Trp Tyr Leu Gln Lys Pro Gly Gln Ser
        35                  40                  45

Pro Gln Leu Leu Ile Tyr Gln Met Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Leu Thr Phe Gly Gly Gly Thr Lys Val Glu Ile Lys
            100                 105                 110

<210> SEQ ID NO 79
<211> LENGTH: 117
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 79

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Thr Thr Tyr
            20                  25                  30

Ala Met Ser Trp Val Arg Gln Ala Pro Gly Lys Gly Leu Glu Trp Val
        35                  40                  45

Ser Thr Ile Ser Ser Gly Gly Thr Tyr Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Thr Gln Gly Asn Tyr Ser Leu Asp Phe Trp Gly Gln Gly Thr Thr
            100                 105                 110

Val Thr Val Ser Ser
        115

<210> SEQ ID NO 80
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ile Phe Ser Ser Tyr
            20                  25                  30

Gly Met Ser Trp Val Arg Gln Ala Pro Gly Lys Gly Leu Glu Trp Val
        35                  40                  45

Ala Asn Ile Asn Thr Phe Gly Asp Arg Thr Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Thr Gly Thr Tyr Trp Gly Gln Gly Thr Leu Val Thr Val
            100                 105                 110

Ser Ser

<210> SEQ ID NO 81
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Asp Val Val Met Thr Gln Ser Pro Leu Ser Leu Pro Val Thr Leu Gly
1               5                   10                  15
```

Gln Pro Ala Ser Ile Ser Cys Arg Ser Ser Gln Ser Leu Leu Asp Ser
                20                  25                  30

Asp Gly Lys Thr Tyr Leu Asn Trp Phe Gln Gln Arg Pro Gly Gln Ser
            35                  40                  45

Pro Arg Arg Leu Ile Tyr Leu Val Ser Asn Arg Asp Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Gln Thr Phe Gly Gly Gly Thr Lys Val Glu Ile Lys
            100                 105                 110

<210> SEQ ID NO 82
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ile Phe Ser Ser Tyr
                20                  25                  30

Gly Met Ser Trp Val Arg Gln Ala Pro Gly Lys Gly Leu Glu Trp Val
            35                  40                  45

Ala Ser Ile Asn Thr Phe Gly Asp Arg Thr Tyr Tyr Val Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Thr Gly Thr Tyr Trp Gly Gln Gly Thr Leu Val Thr Val
            100                 105                 110

Ser Ser

<210> SEQ ID NO 83
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu Asp Ser
                20                  25                  30

Asp Gly Lys Thr Tyr Leu Asn Trp Phe Gln Gln Arg Pro Gly Gln Ser
            35                  40                  45

Pro Arg Arg Leu Ile Tyr Leu Val Ser Lys Arg Asp Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly

```
                   85                  90                  95

Thr His Phe Pro Gln Thr Phe Gly Gly Gly Thr Lys Val Glu Ile Lys
               100                 105                 110

<210> SEQ ID NO 84
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met Tyr Trp Val Arg Gln Ala Pro Gly Gln Gly Leu Glu Trp Met
        35                  40                  45

Gly Ile Ile Asn Pro Ser Asn Gly Gly Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Thr Arg Gly Gly Tyr Tyr Pro Phe Asp Tyr Trp Gly Gln Gly Thr Thr
               100                 105                 110

Val Thr Val Ser Ser
        115

<210> SEQ ID NO 85
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu Asp Ser
            20                  25                  30

Asp Gly Lys Thr Tyr Leu Tyr Trp Phe Gln Gln Arg Pro Gly Gln Ser
        35                  40                  45

Pro Arg Arg Leu Ile Tyr Leu Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Ser Pro Tyr Thr Phe Gly Gln Gly Thr Lys Leu Glu Ile Lys
               100                 105                 110

<210> SEQ ID NO 86
<211> LENGTH: 117
<212> TYPE: PRT
<213> ORGANISM: Artificial Sequence
<220> FEATURE:
<223> OTHER INFORMATION: Description of Artificial Sequence: Synthetic
```

-continued

```
      polypeptide

<400> SEQUENCE: 86

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Asn Gly Gly Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Thr Arg Gly Gly Tyr Tyr Pro Phe Asp Tyr Trp Gly Gln Gly Thr Thr
            100                 105                 110

Val Thr Val Ser Ser
        115

<210> SEQ ID NO 87
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu Asp Ser
            20                  25                  30

Asp Gly Lys Thr Tyr Leu Asn Trp Phe Gln Gln Arg Pro Gly Gln Ser
        35                  40                  45

Pro Arg Arg Leu Ile Tyr Leu Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Ser Pro Tyr Thr Phe Gly Gln Gly Thr Lys Leu Glu Ile Lys
            100                 105                 110

<210> SEQ ID NO 88
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met Tyr Trp Val Arg Gln Ala Pro Gly Gln Gly Leu Glu Trp Met
        35                  40                  45
```

```
Gly Glu Ile Asn Pro Ser Asn Gly Gly Thr Asn Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Thr Arg Gly Gly Tyr Tyr Pro Phe Asp Tyr Trp Gly Gln Gly Thr Thr
            100                 105                 110

Val Thr Val Ser Ser
        115
```

```
<210> SEQ ID NO 89
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu Asp Ser
            20                  25                  30

Asp Gly Lys Thr Tyr Leu Tyr Trp Phe Gln Gln Arg Pro Gly Gln Ser
        35                  40                  45

Pro Arg Arg Leu Ile Tyr Leu Val Ser Glu Arg Asp Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Ser Pro Tyr Thr Phe Gly Gln Gly Thr Lys Leu Glu Ile Lys
            100                 105                 110
```

```
<210> SEQ ID NO 90
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Asp
            20                  25                  30

Tyr Ala Trp Asn Trp Ile Arg Gln His Pro Gly Lys Gly Leu Glu Trp
        35                  40                  45

Ile Gly Tyr Ile Ser Phe Ser Gly Tyr Thr Tyr Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Glu Val Asn Tyr Gly Asp Ser Tyr His Phe Asp Tyr Trp Gly
            100                 105                 110
```

```
Gln Gly Thr Leu Val Thr Val Ser Ser
        115                 120

<210> SEQ ID NO 91
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Gln Leu Val Leu Thr Gln Ser Pro Ser Ala Ser Ala Ser Leu Gly Ala
1               5                   10                  15

Ser Val Lys Leu Thr Cys Thr Leu Ser Ser Gln His Arg Thr Tyr Thr
                20                  25                  30

Ile Glu Trp His Gln Gln Pro Glu Lys Gly Pro Arg Tyr Leu Met
            35                  40                  45

Lys Val Lys Lys Asp Gly Ser His Ser Lys Gly Asp Gly Ile Pro Asp
50                  55                  60

Arg Phe Ser Gly Ser Ser Ser Gly Ala Glu Arg Tyr Leu Thr Ile Ser
65                  70                  75                  80

Ser Leu Gln Ser Glu Asp Glu Ala Asp Tyr Tyr Cys Gly Val Gly Asp
                85                  90                  95

Ala Ile Lys Gly Gln Ser Val Phe Val Phe Gly Gly Thr Lys Val
            100                 105                 110

Glu Ile Lys
        115

<210> SEQ ID NO 92
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Asp
                20                  25                  30

Tyr Ala Trp Ser Trp Ile Arg Gln His Pro Gly Lys Gly Leu Glu Trp
            35                  40                  45

Ile Gly Tyr Ile Ser Phe Ser Gly Tyr Thr Tyr Tyr Asn Pro Ser Leu
50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Glu Val Asn Tyr Gly Asp Ser Tyr His Phe Asp Tyr Trp Gly
            100                 105                 110

Gln Gly Thr Leu Val Thr Val Ser Ser
        115                 120

<210> SEQ ID NO 93
<211> LENGTH: 115
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 93

Gln Leu Val Leu Thr Gln Ser Pro Ser Ala Ser Ala Ser Leu Gly Ala
1               5                   10                  15

Ser Val Lys Leu Thr Cys Thr Leu Ser Ser Gln His Arg Thr Tyr Thr
            20                  25                  30

Ile Ala Trp His Gln Gln Pro Glu Lys Gly Pro Arg Tyr Leu Met
        35                  40                  45

Lys Val Lys Lys Asp Gly Ser His Ser Lys Gly Asp Gly Ile Pro Asp
50                  55                  60

Arg Phe Ser Gly Ser Ser Ser Gly Ala Glu Arg Tyr Leu Thr Ile Ser
65                  70                  75                  80

Ser Leu Gln Ser Glu Asp Glu Ala Asp Tyr Tyr Cys Gly Val Gly Asp
                85                  90                  95

Ala Ile Lys Gly Gln Ser Val Phe Val Phe Gly Gly Thr Lys Val
            100                 105                 110

Glu Ile Lys
        115

<210> SEQ ID NO 94
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Asp
            20                  25                  30

Tyr Ala Trp Asn Trp Ile Arg Gln His Pro Gly Lys Gly Leu Glu Trp
        35                  40                  45

Ile Gly Tyr Ile Ser Phe Ser Gly Tyr Thr Ser Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Glu Val Asn Tyr Gly Asp Ser Tyr His Phe Asp Tyr Trp Gly
            100                 105                 110

Gln Gly Thr Leu Val Thr Val Ser Ser
        115                 120

<210> SEQ ID NO 95
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Gln Leu Val Leu Thr Gln Ser Pro Ser Ala Ser Ala Ser Leu Gly Ala
1               5                   10                  15
```

-continued

```
Ser Val Lys Leu Thr Cys Thr Leu Ser Ser Gln His Arg Thr Tyr Thr
            20                  25                  30

Ile Glu Trp His Gln Gln Gln Pro Glu Lys Gly Pro Arg Tyr Leu Met
        35                  40                  45

Glu Val Lys Lys Asp Gly Ser His Ser Lys Gly Asp Gly Ile Pro Asp
    50                  55                  60

Arg Phe Ser Gly Ser Ser Ser Gly Ala Glu Arg Tyr Leu Thr Ile Ser
65                  70                  75                  80

Ser Leu Gln Ser Glu Asp Glu Ala Asp Tyr Tyr Cys Gly Val Gly Asp
                85                  90                  95

Ala Ile Lys Gly Gln Ser Val Phe Val Phe Gly Gly Gly Thr Lys Val
            100                 105                 110

Glu Ile Lys
        115
```

<210> SEQ ID NO 96
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Ahx

<400> SEQUENCE: 96

```
Cys Xaa Xaa Gln Gly Pro Trp Leu Glu Glu Glu Glu Ala Tyr Gly
1               5                   10                  15

Trp Met Asp Phe Gly Arg Arg Ser Ala Glu Asp Glu Asn
            20                  25
```

<210> SEQ ID NO 97
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Ahx

<400> SEQUENCE: 97

```
Cys Xaa Xaa Phe Gly Arg Arg Ser Ala Glu Asp Glu Asn
1               5                   10
```

<210> SEQ ID NO 98
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(12)
<223> OTHER INFORMATION: Ahx

<400> SEQUENCE: 98

```
Phe Gly Arg Arg Ser Ala Glu Asp Glu Asn Xaa Xaa Cys
1               5                   10
```

```
<210> SEQ ID NO 99
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Gly Gly Gly Gly Ser Gly Gly Gly Gly Ser Gly Gly Gly Gly Ser
1               5                   10                  15

<210> SEQ ID NO 100
<211> LENGTH: 101
<212> TYPE: PRT
<213> ORGANISM: Homo sapiens

<400> SEQUENCE: 100

Met Gln Arg Leu Cys Val Tyr Val Leu Ile Phe Ala Leu Ala Leu Ala
1               5                   10                  15

Ala Phe Ser Glu Ala Ser Trp Lys Pro Arg Ser Gln Gln Pro Asp Ala
            20                  25                  30

Pro Leu Gly Thr Gly Ala Asn Arg Asp Leu Glu Leu Pro Trp Leu Glu
        35                  40                  45

Gln Gln Gly Pro Ala Ser His His Arg Arg Gln Leu Gly Pro Gln Gly
    50                  55                  60

Pro Pro His Leu Val Ala Asp Pro Ser Lys Lys Gln Gly Pro Trp Leu
65                  70                  75                  80

Glu Glu Glu Glu Glu Ala Tyr Gly Trp Met Asp Phe Gly Arg Arg Ser
                85                  90                  95

Ala Glu Asp Glu Asn
            100

<210> SEQ ID NO 101
<211> LENGTH: 80
<212> TYPE: PRT
<213> ORGANISM: Homo sapiens

<400> SEQUENCE: 101

Ser Trp Lys Pro Arg Ser Gln Gln Pro Asp Ala Pro Leu Gly Thr Gly
1               5                   10                  15

Ala Asn Arg Asp Leu Glu Leu Pro Trp Leu Glu Gln Gln Gly Pro Ala
            20                  25                  30

Ser His His Arg Arg Gln Leu Gly Pro Gln Gly Pro Pro His Leu Val
        35                  40                  45

Ala Asp Pro Ser Lys Lys Gln Gly Pro Trp Leu Glu Glu Glu Glu Glu
    50                  55                  60

Ala Tyr Gly Trp Met Asp Phe Gly Arg Arg Ser Ala Glu Asp Glu Asn
65                  70                  75                  80

<210> SEQ ID NO 102
<211> LENGTH: 34
<212> TYPE: PRT
<213> ORGANISM: Homo sapiens

<400> SEQUENCE: 102

Gln Leu Gly Pro Gln Gly Pro Pro His Leu Val Ala Asp Pro Ser Lys
1               5                   10                  15

Lys Gln Gly Pro Trp Leu Glu Glu Glu Glu Glu Ala Tyr Gly Trp Met
            20                  25                  30
```

```
<210> SEQ ID NO 103
<211> LENGTH: 35
<212> TYPE: PRT
<213> ORGANISM: Homo Sapiens

<400> SEQUENCE: 103

Gln Leu Gly Pro Gln Gly Pro Pro His Leu Val Ala Asp Pro Ser Lys
1               5                   10                  15

Lys Gln Gly Pro Trp Leu Glu Glu Glu Glu Ala Tyr Gly Trp Met
            20                  25                  30

Asp Phe Gly
        35

<210> SEQ ID NO 104
<211> LENGTH: 17
<212> TYPE: PRT
<213> ORGANISM: Homo sapiens

<400> SEQUENCE: 104

Gln Gly Pro Trp Leu Glu Glu Glu Glu Ala Tyr Gly Trp Met Asp
1               5                   10                  15

Phe

<210> SEQ ID NO 105
<211> LENGTH: 18
<212> TYPE: PRT
<213> ORGANISM: Homo sapiens

<400> SEQUENCE: 105

Gln Gly Pro Trp Leu Glu Glu Glu Glu Ala Tyr Gly Trp Met Asp
1               5                   10                  15

Phe Gly

<210> SEQ ID NO 106
<211> LENGTH: 6
<212> TYPE: PRT
<213> ORGANISM: Homo sapiens

<400> SEQUENCE: 106

Ser Ala Glu Asp Glu Asn
1               5
```